(12) United States Patent
Stewart et al.

(10) Patent No.: US 8,257,351 B2
(45) Date of Patent: Sep. 4, 2012

(54) ABLATION CATHETER ASSEMBLY WITH RADIALLY DECREASING HELIX AND METHOD OF USE

(75) Inventors: Mark T. Stewart, Lino Lakes, MN (US); James R. Skarda, Lake Elmo, MN (US)

(73) Assignee: Medtronic, Inc., Minneapolis, MN (US)

( * ) Notice: Subject to any disclaimer, the term of this patent is extended or adjusted under 35 U.S.C. 154(b) by 321 days.

(21) Appl. No.: 12/760,807

(22) Filed: Apr. 15, 2010

(65) Prior Publication Data
US 2010/0204692 A1 Aug. 12, 2010

Related U.S. Application Data

(60) Division of application No. 10/655,197, filed on Sep. 4, 2003, now Pat. No. 7,771,421, which is a continuation-in-part of application No. 09/848,555, filed on May 3, 2001, now Pat. No. 6,702,811, which is a continuation-in-part of application No. 09/733,356, filed on Dec. 8, 2000, now abandoned, which is a continuation-in-part of application No. 09/286,048, filed on Apr. 5, 1999, now Pat. No. 6,325,797.

(51) Int. Cl.
*A61B 18/04* (2006.01)
(52) U.S. Cl. ........................................ 606/41
(58) Field of Classification Search ............ 606/41; 128/898; 607/96, 98, 101, 102, 104–106
See application file for complete search history.

(56) References Cited

U.S. PATENT DOCUMENTS

| | | |
|---|---|---|
| 3,935,348 A | 1/1976 | Smith |
| 4,961,377 A | 10/1990 | Bando et al. |
| 5,239,999 A | 8/1993 | Imran |
| 5,263,492 A | 11/1993 | Voyce |
| 5,296,510 A | 3/1994 | Yamada et al. |
| 5,318,525 A | 6/1994 | West et al. |
| 5,354,297 A | 10/1994 | Avitall |
| 5,397,304 A | 3/1995 | Truckai |
| 5,462,545 A | 10/1995 | Wang et al. |
| 5,487,385 A | 1/1996 | Avitall |
| 5,487,757 A | 1/1996 | Truckai et al. |
| 5,497,774 A | 3/1996 | Swartz et al. |
| 5,529,820 A | 6/1996 | Nomi et al. |
| 5,545,193 A | 8/1996 | Fleischman et al. |
| 5,545,200 A | 8/1996 | West et al. |

(Continued)

FOREIGN PATENT DOCUMENTS
EP  1042990  10/2000
(Continued)

*Primary Examiner* — Roy Gibson

(57) ABSTRACT

A catheter assembly for treatment of cardiac arrhythmia. The catheter assembly includes a catheter body and an ablative energy source. The catheter body includes a proximal portion, an intermediate portion, and a distal portion. The intermediate portion extends from the proximal portion and defines a longitudinal axis. The distal portion extends from the intermediate portion and includes an ablation section and a tip. The ablation section forms a loop defining a diameter greater than an outer dimension of a pulmonary vein ostium. The tip extends distally from the ablation section and is configured to locate a pulmonary vein. Finally, the ablative energy source is associated with the ablation section. With this configuration, upon activation of the energy source, the ablation section ablates a desired lesion pattern. In one preferred embodiment, the ablation section forms a distally decreasing radius helix, whereas the tip includes a relatively linear leader section. With this one preferred configuration, the tip readily locates a pulmonary vein and guides the ablation section to a seated relationship about a pulmonary vein ostium (or extra-ostial).

12 Claims, 32 Drawing Sheets

U.S. PATENT DOCUMENTS

| | | | |
|---|---|---|---|
| 5,545,475 A | 8/1996 | Korleski |
| 5,549,661 A | 8/1996 | Kordis et al. |
| 5,564,440 A | 10/1996 | Swartz et al. |
| 5,575,766 A | 11/1996 | Swartz et al. |
| 5,575,810 A | 11/1996 | Swanson et al. |
| 5,582,609 A | 12/1996 | Swanson et al. |
| 5,617,854 A | 4/1997 | Munsif |
| 5,637,090 A | 6/1997 | McGee et al. |
| 5,680,860 A | 10/1997 | Imran |
| 5,687,723 A | 11/1997 | Avitall |
| 5,690,611 A | 11/1997 | Swartz et al. |
| 5,715,818 A | 2/1998 | Swartz et al. |
| 5,725,512 A | 3/1998 | Swartz et al. |
| 5,730,127 A | 3/1998 | Avitall |
| 5,755,760 A | 5/1998 | Maguire et al. |
| 5,814,028 A | 9/1998 | Swartz et al. |
| 5,823,955 A | 10/1998 | Kuck et al. |
| 5,842,984 A | 12/1998 | Avitall |
| 5,846,355 A | 12/1998 | Spencer et al. |
| 5,860,920 A | 1/1999 | McGee et al. |
| 5,871,523 A | 2/1999 | Fleischman et al. |
| 5,882,346 A | 3/1999 | Pomeranz et al. |
| 5,910,129 A | 6/1999 | Koblish et al. |
| 5,938,694 A | 8/1999 | Jaraczewski et al. |
| 5,957,961 A | 9/1999 | Maguire et al. |
| 5,993,462 A | 11/1999 | Pomeranz et al. |
| 6,004,348 A | 12/1999 | Banas et al. |
| 6,012,457 A | 1/2000 | Lesh |
| 6,032,077 A | 2/2000 | Pomeranz |
| 6,042,578 A | 3/2000 | Dinh et al. |
| 6,064,902 A | 5/2000 | Haissaguerre et al. |
| 6,076,012 A | 6/2000 | Swanson et al. |
| 6,096,036 A | 8/2000 | Bowe et al. |
| 6,106,522 A | 8/2000 | Fleischman et al. |
| 6,164,283 A | 12/2000 | Lesh |
| 6,325,797 B1 | 12/2001 | Stewart et al. |
| 6,364,904 B1 | 4/2002 | Smith |
| 6,500,174 B1 | 12/2002 | Maguire et al. |
| 6,602,242 B1 | 8/2003 | Fung et al. |
| 6,607,520 B2 | 8/2003 | Keane |
| 6,652,517 B1 | 11/2003 | Hall et al. |
| 6,702,811 B2 | 3/2004 | Stewart et al. |
| 6,923,808 B2 | 8/2005 | Taimisto |
| 6,960,207 B2 | 11/2005 | Vanney et al. |
| 7,013,169 B2 | 3/2006 | Bowe |
| 2001/0007070 A1 | 7/2001 | Stewart et al. |
| 2001/0020174 A1 | 9/2001 | Koblish |
| 2002/0004631 A1 | 1/2002 | Jenkins et al. |
| 2002/0062124 A1 | 5/2002 | Keane |
| 2002/0087208 A1 | 7/2002 | Koblish et al. |
| 2002/0165532 A1 | 11/2002 | Hill, III et al. |
| 2006/0241366 A1 | 10/2006 | Falwell et al. |

FOREIGN PATENT DOCUMENTS

| | | |
|---|---|---|
| JP | 355137141 | 10/2008 |
| WO | 0056237 | 9/2000 |
| WO | 0067832 | 11/2000 |
| WO | 0137723 | 5/2001 |
| WO | 0137746 | 5/2001 |
| WO | 0180758 | 11/2001 |
| WO | 0245608 | 6/2002 |

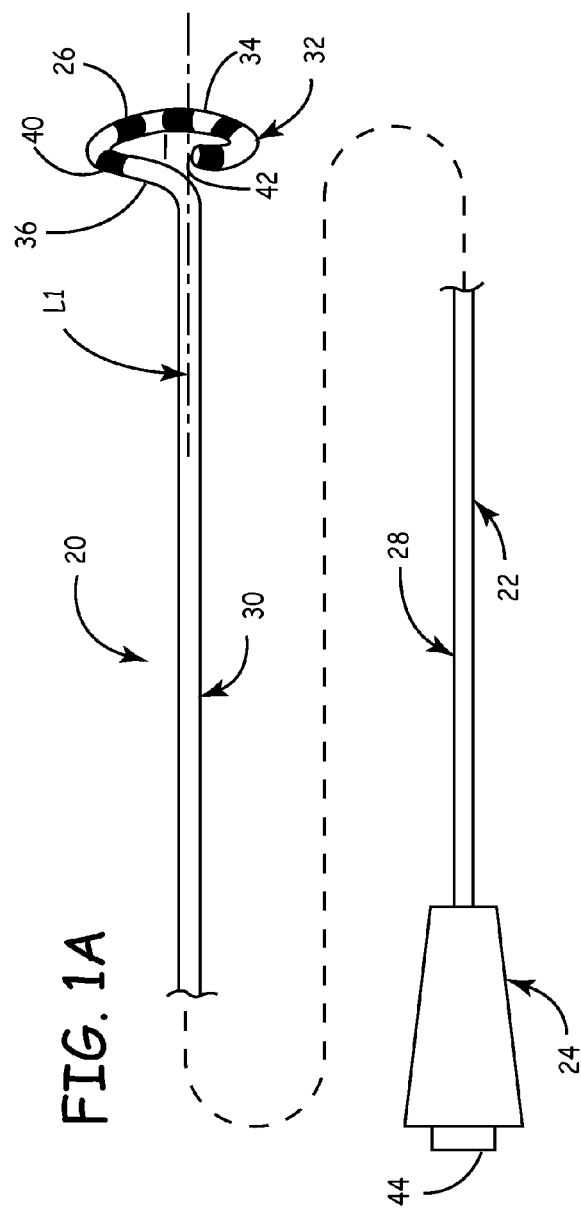
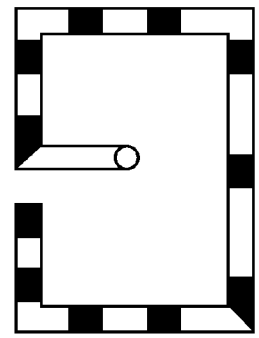
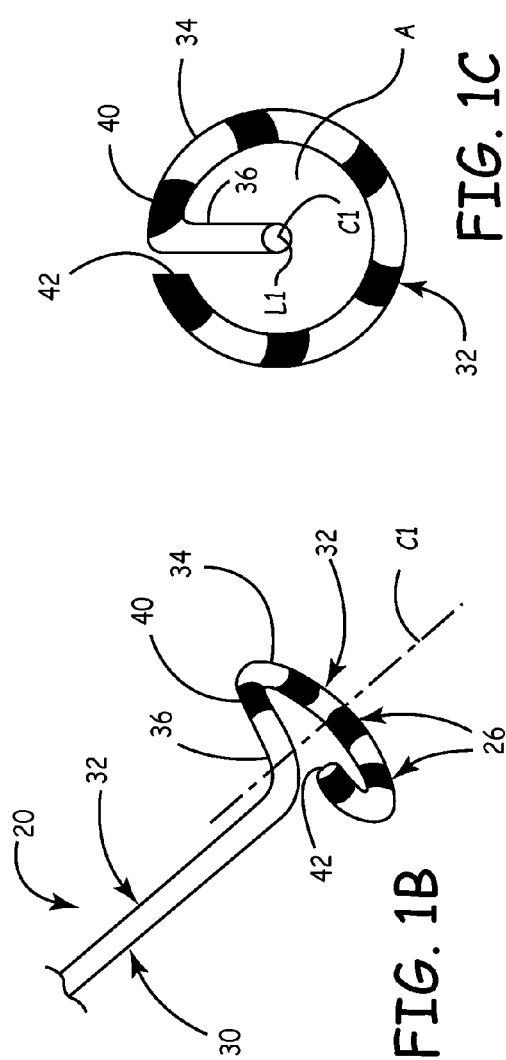

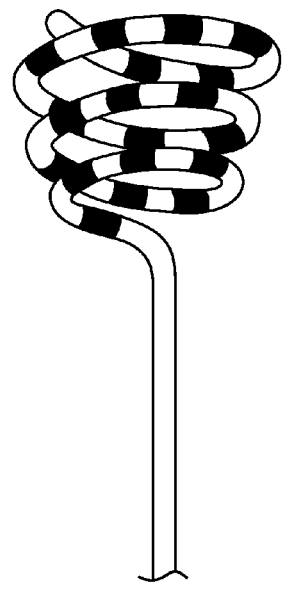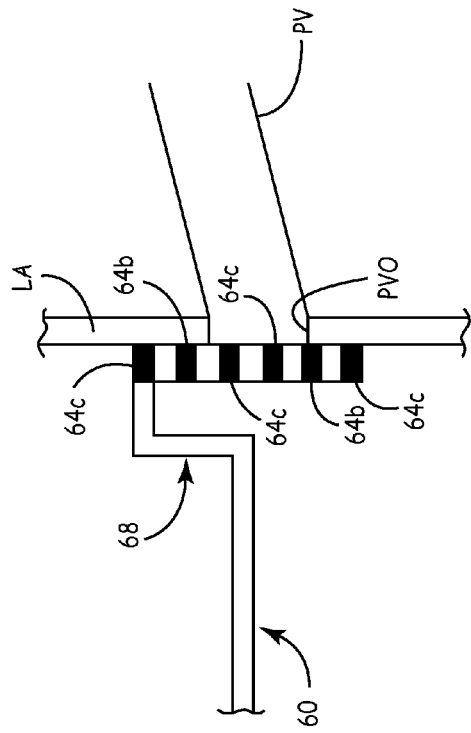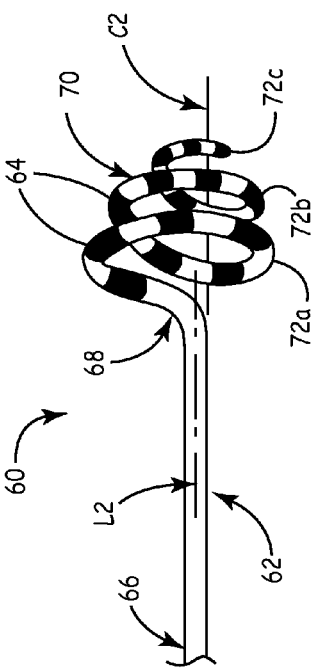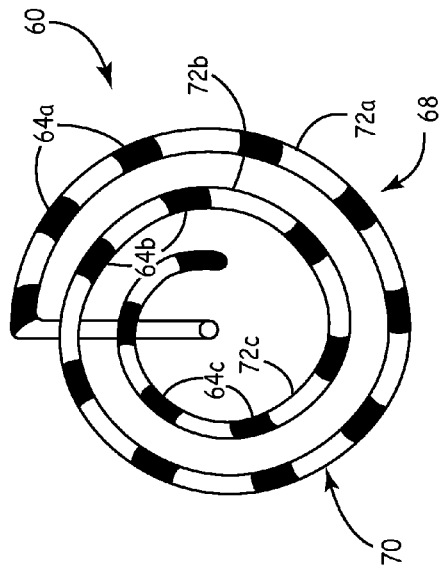

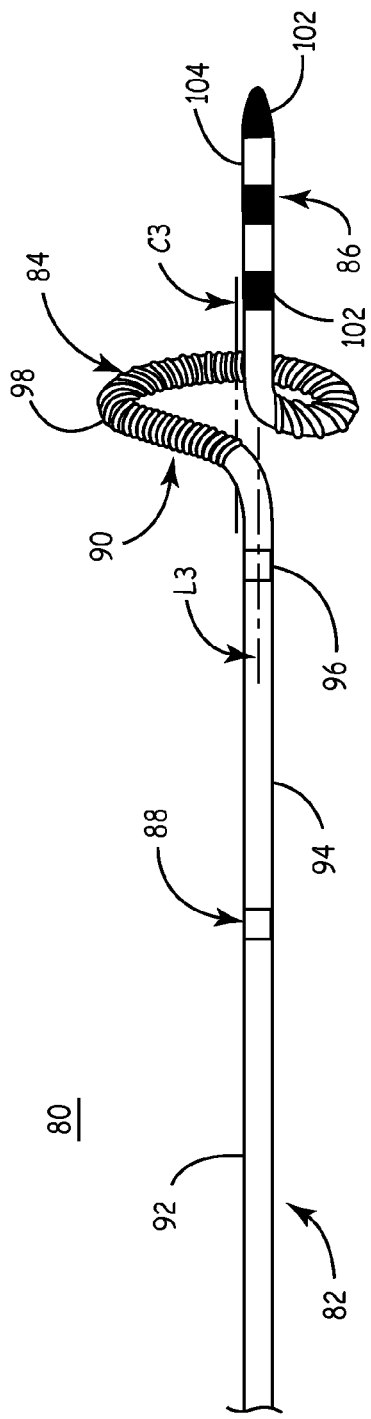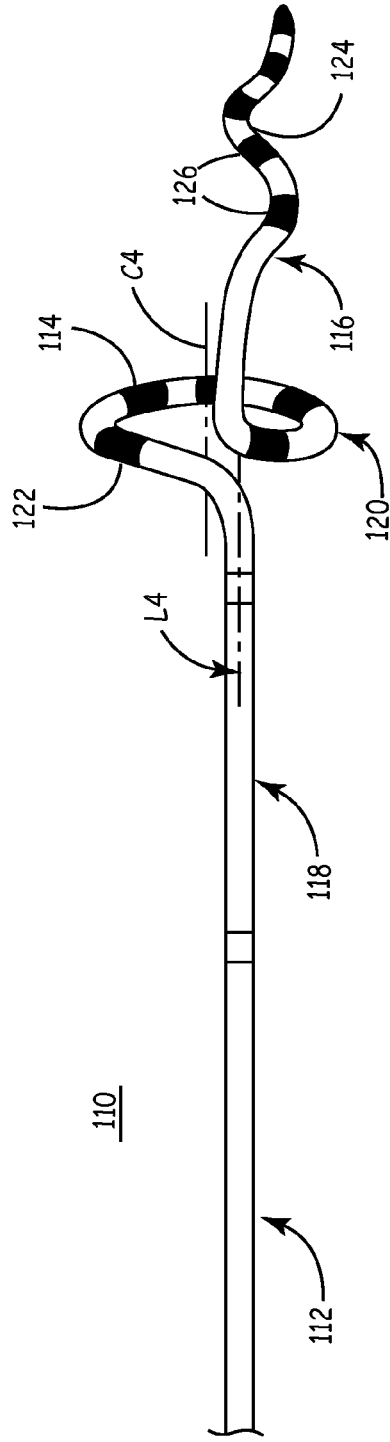

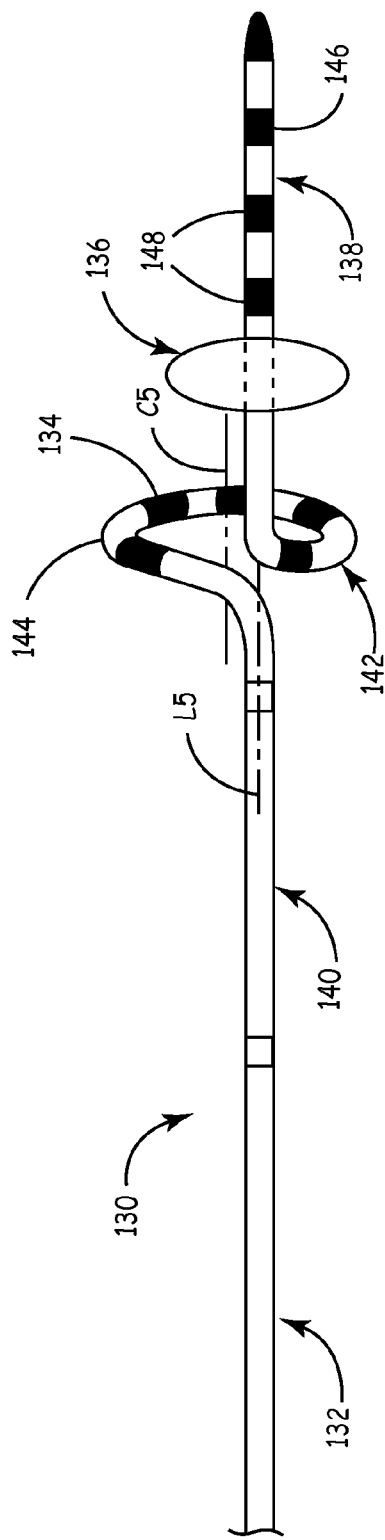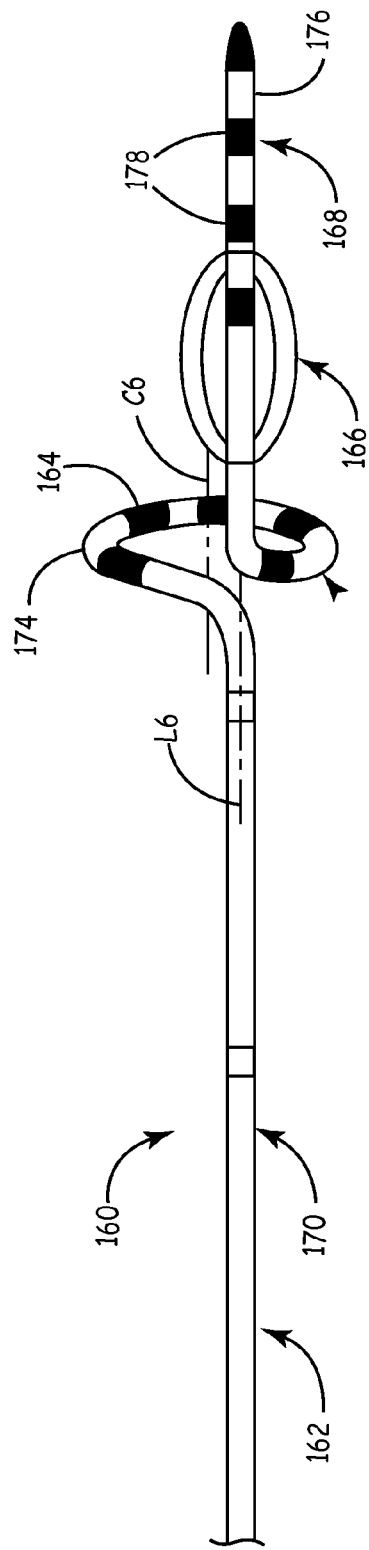

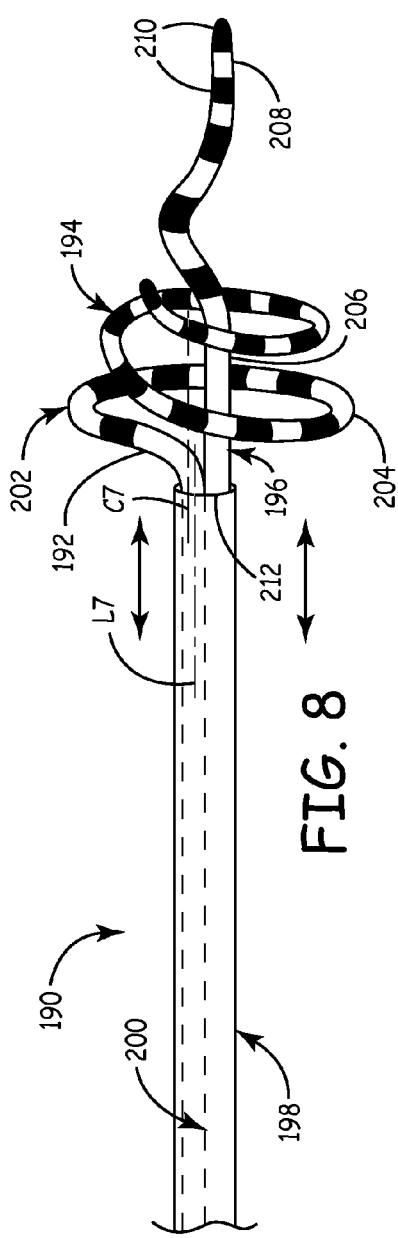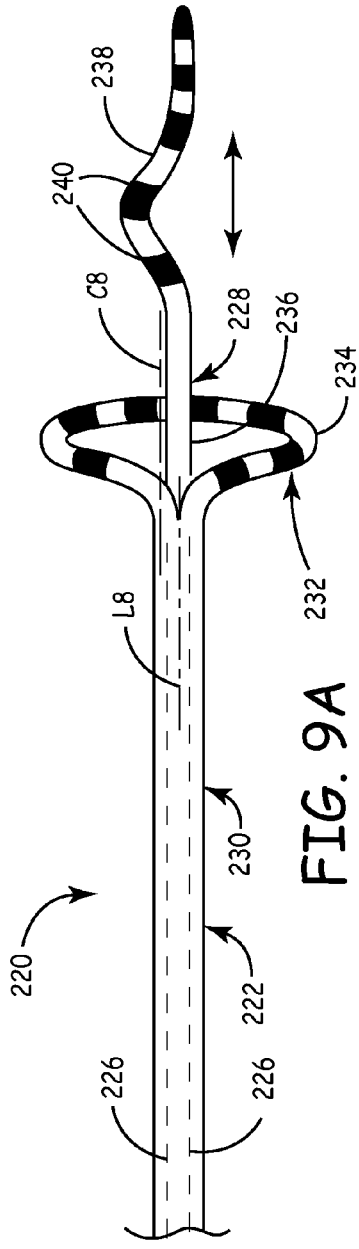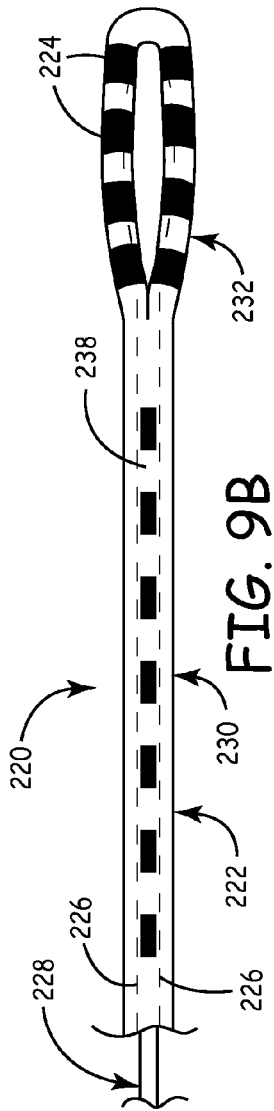

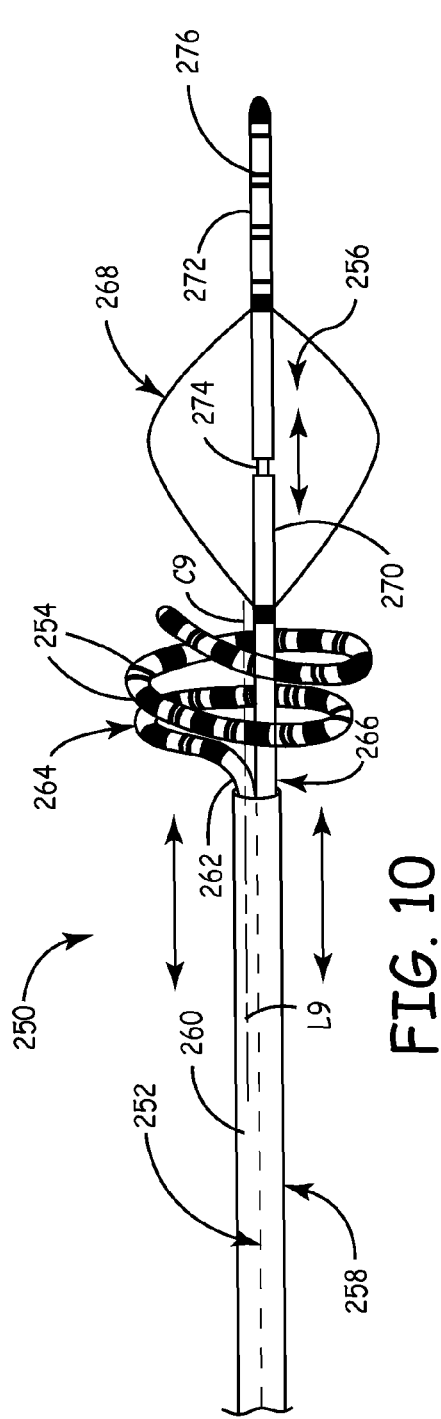
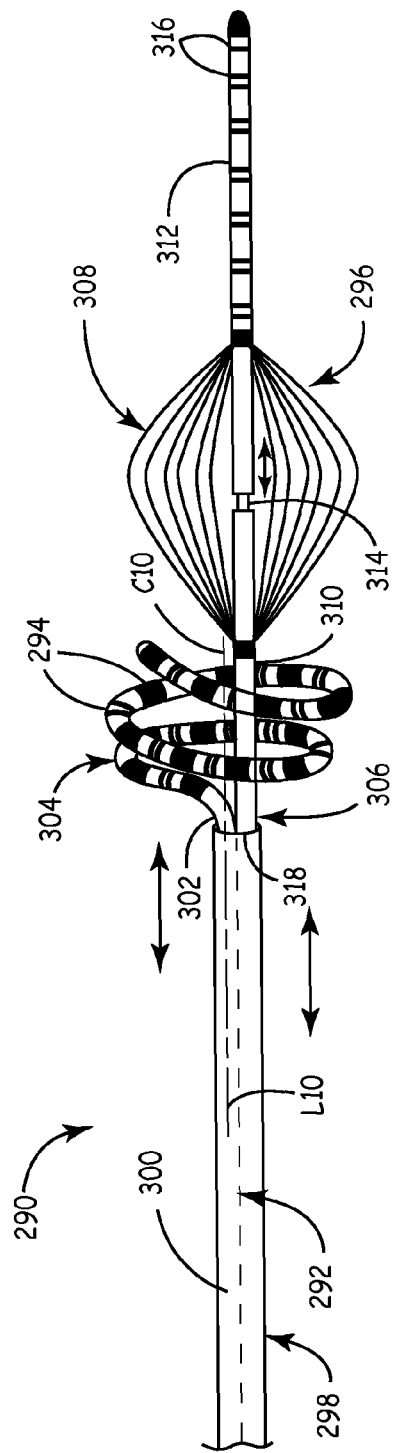
FIG. 10
FIG. 11

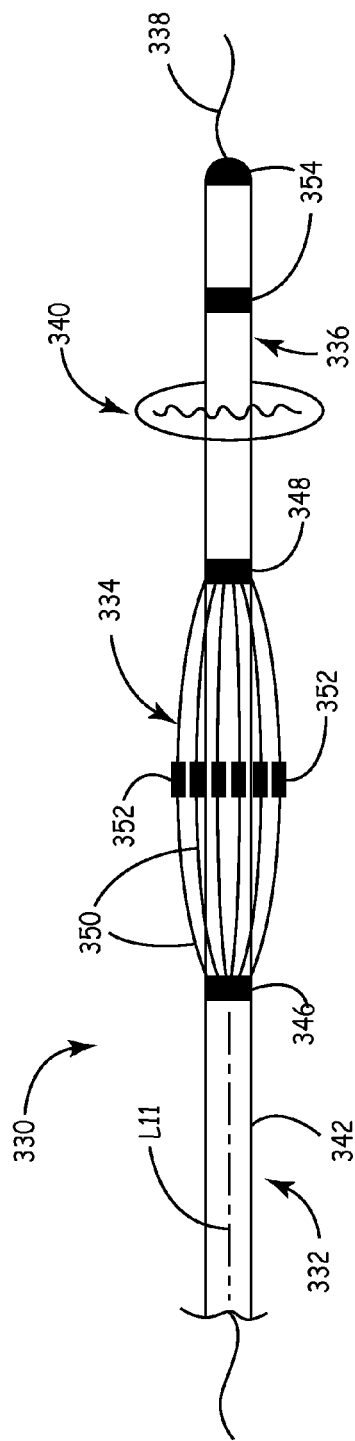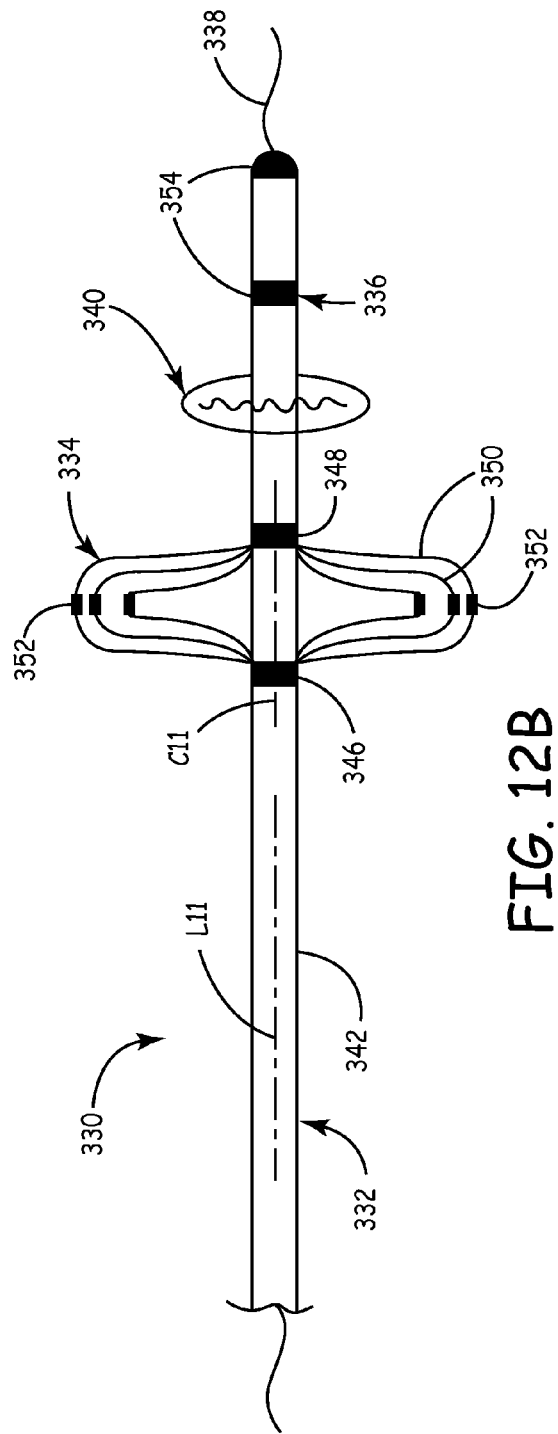

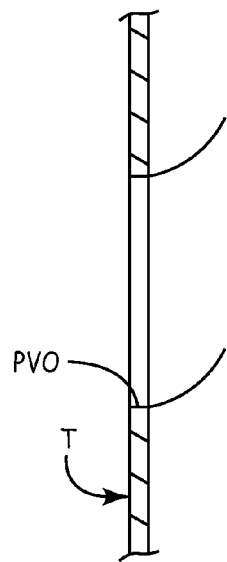 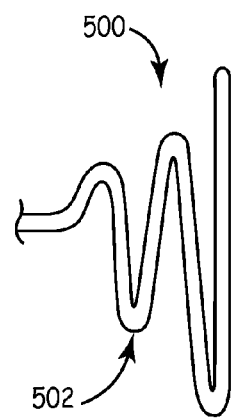 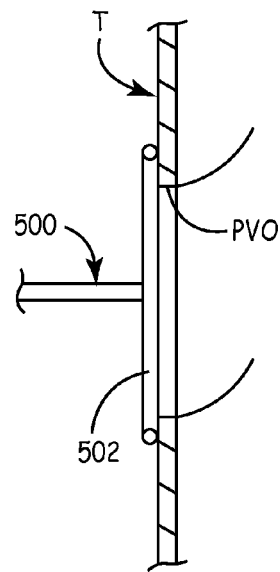
FIG. 20A　　　FIG. 20B　　　FIG. 20C
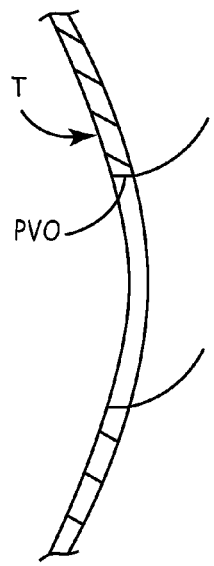 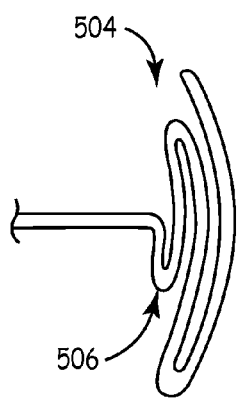 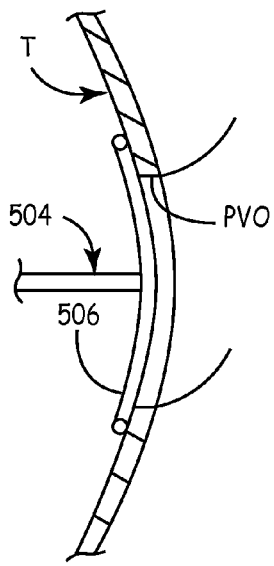
FIG. 21A　　　FIG. 21B　　　FIG. 21C

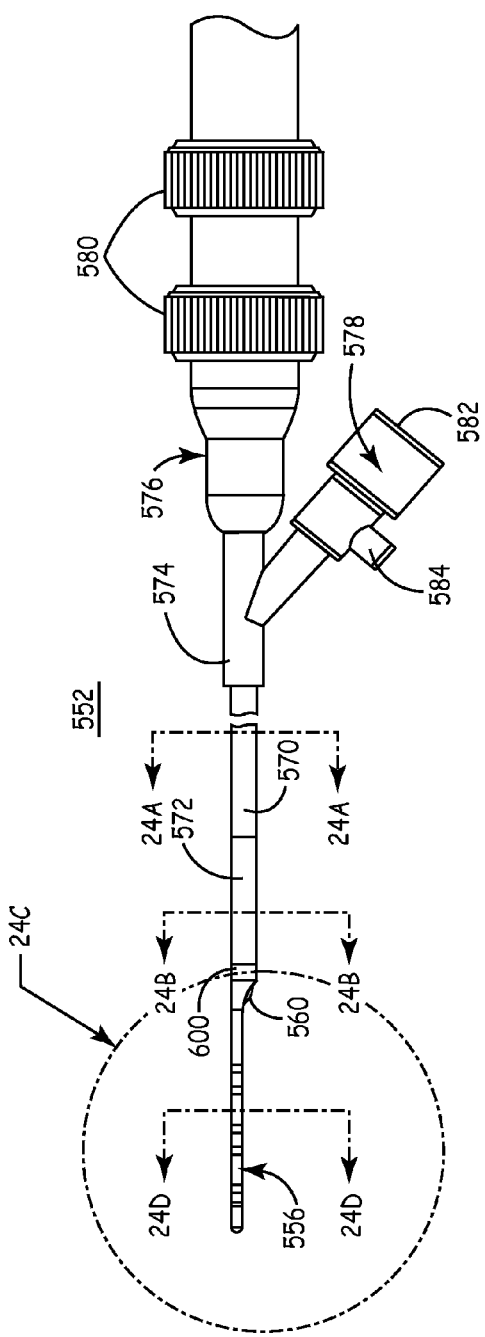
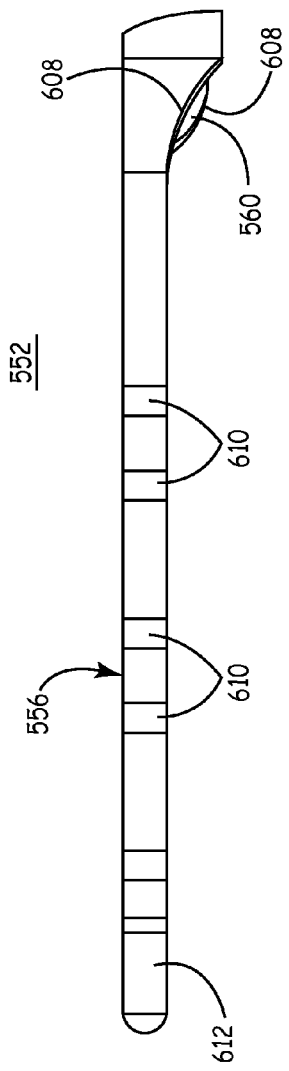
FIG. 23
FIG. 24C

ABLATION CATHETER ASSEMBLY WITH RADIALLY DECREASING HELIX AND METHOD OF USE

CROSS-REFERENCE TO RELATED APPLICATIONS

This application is a divisional of U.S. patent application Ser. No. 10/655,197, entitled "Ablation Catheter Assembly with Radially Decreased Helix and Method of Use", filed Sep. 4, 2003, now U.S. Pat. No. 7,771,421 now allowed, which is a continuation-in-part of U.S. patent Ser. No. 09/848,555, entitled "Ablation Catheter Assembly and Method for Isolating a Pulmonary Vein, filed on May 3, 2001, now U.S. Pat. No. 6,702,811 which is a continuation-in-part of U.S. patent application Ser. No. 09/733,356, entitled "Ablation Catheter Assembly and Method for Isolating a Pulmonary Vein", filed Dec. 8, 2000, now abandoned, which is a continuation in part of U.S. patent Ser. No. 09/286,048, entitled "Ablation Catheter and Method for Isolating a Pulmonary Vein", filed Apr. 5, 1999, now U.S. Pat. No. 6,325,797 the contents of which are incorporated by reference herein it its entirety.

BACKGROUND OF THE INVENTION

The present invention relates to an ablation catheter for treatment of cardiac arrhythmia, for example atrial fibrillation. More particularly, it relates to an ablation catheter configured to electrically isolate portions or an entirety of a vessel, such as a pulmonary vein, from a chamber, such as the left atrium, with a lesion pattern and a method for forming such a lesion pattern.

The heart includes a number of pathways that are responsible for the propagation of signals necessary to produce continuous, synchronized contractions. Each contraction cycle begins in the right atrium where a sinoatral node initiates an electrical impulse. This impulse then spreads across the right atrium to the left atrium, stimulating the atria to contract. The chain reaction continues from the atria to the ventricles by passing through a pathway known as the atrioventricular (AV) node or junction, which acts as an electrical gateway to the ventricles. The AV junction delivers the signal to the ventricles while also slowing it, so the atria can relax before the ventricles contract.

Disturbances in the heart's electrical system may lead to various rhythmic problems that can cause the heart to beat irregularly, too fast or too slow. Irregular heart beats, or arrhythmia, are caused by physiological or pathological disturbances in the discharge of electrical impulses from the sinoatrial node, in the transmission of the signal through the heart tissue, or spontaneous, unexpected electrical signals generated within the heart. One type of arrhythmia is tachycardia, which is an abnormal rapidity of heart action. There are several different forms of atrial tachycardia, including atrial fibrillation and atrial flutter. With atrial fibrillation, instead of a single beat, numerous electrical impulses are generated by depolarizing tissue at one or more locations in the atria (or possibly other locations). These unexpected electrical impulses produce irregular, often rapid heartbeats in the atrial muscles and ventricles. Patients experiencing atrial fibrillation may suffer from fatigue, activity intolerance, dizziness and even strokes.

The precise cause of atrial fibrillation, and in particular the depolarizing tissue causing "extra" electrical signals, is currently unknown. As to the location of the depolarizing tissue, it is generally agreed that the undesired electrical impulses often originate in the left atrial region of the heart. Recent studies have expanded upon this general understanding, suggesting that nearly 90% of these "focal triggers" or electrical impulses are generated in one (or more) of the four pulmonary veins (PV) extending from the left atrium. In this regard, as the heart develops from an embryotic stage, left atrium tissue may grow or extend a short distance into one or more of the PVs. It has been postulated that this tissue may spontaneously depolarize, resulting in an unexpected electrical impulse(s) propagating into the left atrium and along the various electrical pathways of the heart.

A variety of different atrial fibrillation treatment techniques are available, including drugs, surgery, implants, and catheter ablation. While drugs may be the treatment of choice for some patients, drugs typically only mask the symptoms and do not cure the underlying cause. Implantable devices, on the other hand, usually correct an arrhythmia only after it occurs. Surgical and catheter-based treatments, in contrast, will actually cure the problem by ablating the abnormal tissue or accessory pathway responsible for the atrial fibrillation. The catheter-based treatments rely on the application of various destructive energy sources to the target tissue, including direct current electrical energy, radiofrequency electrical energy, laser energy, and the like. The energy source, such as an ablating electrode, is normally disposed along a distal portion of a catheter.

Most ablation catheter techniques employed to treat atrial fibrillation focus upon locating the ablating electrode, or a series of ablating electrodes, along extended target sections of the left atrium wall. Because the atrium wall, and thus the targeted site(s), is relatively tortuous, the resulting catheter design includes multiple curves, bends, extensions, etc. In response to recent studies indicating that the unexpected electrical impulses are generated within a PV, efforts have been made to ablate tissue within the PV itself. Obviously, the prior catheter designs incorporating convoluted, multiple bends are not conducive to placement within a PV. Instead, a conventional "straight ended" ablation catheter has been employed. While this technique of tissue ablation directly within a PV has been performed with relatively high success, other concerns may arise.

More particularly, due to the relatively small thickness of atrial tissue formed within a PV, it is likely that ablation of this tissue may in fact cause the PV to shrink or constrict. Because PV's have a relatively small diameter, a stenosis may result. Even further, other vital bodily structures are directly adjacent each PV. These structures may be undesirably damaged when ablating within a PV.

In light of the above, an alternative technique has been suggested whereby a continuous ablation lesion pattern is formed in the left atrium wall about the ostium associated with the PV in question. In other words, the PV is electrically isolated from the left atrium by forming an ablation lesion pattern that surrounds the PV ostium. As a result, any undesired electrical impulse generated within the PV could not propagate into the left atrium, thereby eliminating unexpected atria contraction.

Unfortunately, while PV isolation via a continuous ablation lesion pattern about the PV ostium appears highly viable, no acceptable ablation catheter configuration exists. Most atrial fibrillation ablation catheters have linear distal ends, designed for manipulation in a sliding fashion along the atrial wall. That is to say, the distal, electrode-carrying end of the catheter is typically slid along (or parallel to) the atrial wall. With this generally accepted configuration in mind, it may be possible to shape the distal, electrode-carrying end into a small ring sized in accordance with the PV ostium. For example, U.S. Pat. No. 5,617,854 discloses one such possibility. More particularly, the described ablation catheter includes a substantially ring-shaped portion sized to contact the ostium of the coronary sinus. Pursuant to conventional designs, the ring extends linearly from the catheter body. In theory, the ring-shaped portion may be placed about a PV ostium. However, proper positioning would be extremely difficult and time consuming More particularly, it would be virtually impossible to locate and then align the ring about a PV ostium when sliding the catheter along the atrium wall. The ring must be directed toward the ostium in a radial direction (relative to a central axis of the ostium). Even if the electrophysiologist were able to direct the ring to the ostium, the periodic blood flow through the PV would likely force the ring away from the atrium wall, as the catheter body would not provide any support.

A related concern entails mapping of a PV prior to ablation. In cases of atrial fibrillation, it is necessary to identify the origination point of the undesired electrical impulses prior to ablation. Thus, it must first be determined if the electrical impulse originates within one or more PVs. Once the depolarizing tissue has been identified, necessary ablation steps can be taken. Mapping is normally accomplished by placing one or more mapping electrodes into contact with the tissue in question. In order to map tissue within a PV, therefore, a relatively straight catheter section maintaining two or more mapping electrodes must be extended axially within the PV. Ablation catheters configured to slide along the atrial wall cannot include a separate, distal extension for placement within the PV. Instead, an entirely separate mapping catheter must be provided and then removed for subsequent replacement with the ablation catheter. Obviously, these additional steps greatly increase the overall time required to complete the procedure.

Electrical isolation of a pulmonary vein via an ablation lesion pattern surrounding the pulmonary vein ostium presents a potentially revolutionary technique for treatment of atrial fibrillation. However, the unique anatomical characteristics of a pulmonary vein and left atrium render currently available ablation catheters minimally useful. Therefore, a substantial need exists for an ablation catheter designed for consistent positioning of one or more ablation electrodes about a pulmonary vein ostium, as well as for providing pulmonary vein mapping information.

SUMMARY OF THE INVENTION

One aspect of the present invention provides a catheter assembly for treatment of cardiac arrhythmia. The catheter assembly includes a catheter body and an ablative energy source. The catheter body includes a proximal portion, an intermediate portion, and a distal portion. The intermediate portion extends from the proximal portion and defines a longitudinal axis. The distal portion extends from the intermediate portion and includes an ablation section and a tip. The ablation section forms a loop defining a diameter greater than an outer dimension of a pulmonary vein ostium. The tip extends distally from the ablation section and is configured to locate a pulmonary vein. Finally, the ablative energy source is associated with the ablation section. With this configuration, upon activation of the energy source, the ablation section ablates a desired lesion pattern. In one preferred embodiment, the ablation section forms a distally decreasing radius helix, whereas the tip includes a relatively linear leader section. With this one preferred configuration, the tip readily locates a pulmonary vein and guides the ablation section to a seated relationship about a pulmonary vein ostium.

Another aspect of the present invention relates to a catheter assembly for electrically isolating a vessel from a chamber for treatment of cardiac arrhythmia. The catheter assembly includes a catheter body and an ablative energy source. The catheter body includes a proximal portion, an intermediate portion, and a distal portion. The intermediate portion extends from the proximal portion and defines a longitudinal axis. The distal portion extends from the intermediate portion and includes an ablation section and a tip. The ablation section forms a loop. The tip extends distally from the ablation section and is configured to locate a vessel. Further, the tip is characterized has having a feature different from that of the ablation section. In particular, the tip has either a different shape, material, durometer, or porosity as compared to the ablation section. Finally, the ablative energy source is associated with the ablation section. With this configuration, upon activation of the energy source, the ablation section ablates a desired lesion pattern. By forming the tip to have a feature different from that of the ablation section, the catheter assembly more readily locates a vessel, such as a pulmonary vein, and seats the ablation section about the vessel ostium, thereby promoting a properly located and uniform ablation pattern. In one preferred embodiment, the ablation section is formed of a microporous polymer, whereas the tip is impervious to fluid flow. With this configuration, fluid is irrigated to an exterior of the ablation section and then energized to ablate the tissue.

Yet another aspect of the present invention relates to a catheter assembly for electrically isolating a vessel from a chamber for treatment of cardiac arrhythmia. The catheter assembly includes a catheter body and an ablative energy source. The catheter body includes a proximal portion, an intermediate portion, and a distal portion. The intermediate portion extends from the proximal portion and defines a longitudinal axis. The distal portion extends from the intermediate portion and includes an ablation section and a tip. The ablation section forms a loop transverse to the longitudinal axis. The tip extends distally from the ablation section and defines a shape different from a shape defined by the ablation section. Finally, the ablative energy source is associated with the ablation section. With this configuration, upon activation of the energy source, the ablation section ablates a desired lesion pattern. In one preferred embodiment, the ablation section and the tip define different distally decreasing radius helixes.

Yet another aspect of the present invention relates to a method of electrically isolating a vessel from a chamber for treatment of cardiac arrhythmia In this regard, the vessel forms an ostium at a wall of the chamber. With this in mind, the method includes selecting a catheter assembly including a catheter body and an ablative energy source. The catheter body includes a proximal portion and a distal portion, with the distal portion including an ablation section and a tip. The ablation section forms a loop and the tip extends distally from the ablation section. Further, the ablative energy source is associated with the ablation section. The distal portion of the catheter body is then guided into the chamber. The vessel is located with the tip. The distal portion is then advanced such that the ablation section contacts the chamber wall about the vessel ostium. In this regard, interaction between the tip and the vessel properly positions the ablation section relative to the vessel ostium as the distal portion is advanced. Finally, the ablative energy source is activated to ablate a desired lesion pattern about at a portion of at least a portion of the ostium to electrically isolate the vessel from the chamber. In one preferred embodiment, the tip is prevented from ablating the vessel during activation of the ablative energy source.

BRIEF DESCRIPTION OF THE DRAWINGS

FIG. 1A is a side-elevational view of a catheter assembly in accordance with the present invention;

FIG. 1B is a perspective view of a portion of the catheter assembly of FIG. 1A;

FIG. 1C is an end view of a portion of the catheter assembly of FIG. 1A;

FIG. 1D is an end view of a portion of an alternative catheter assembly in accordance with the present invention;

FIG. 3A is a side view of a portion of an alternative catheter assembly in accordance with the present invention;

FIG. 3B is an end view of the catheter assembly of FIG. 3A;

FIG. 3C is a side view of a portion of an alternative catheter assembly in accordance with the present invention;

FIG. 3D is a simplified cross-sectional view of a portion of the heart and a portion of the catheter assembly of FIGS. 3A and 3B;

FIG. 4A is a side view of a portion of an alternative catheter assembly in accordance with the present invention;

FIG. 5 is a side view of a portion of an alternative catheter assembly in accordance with the present invention;

FIG. 6 is a side view of a portion of an alternative catheter assembly in accordance with the present invention;

FIG. 7 is a side view of a portion of an alternative catheter assembly in accordance with the present invention;

FIG. 8 is a side view of a portion of an alternative catheter assembly in accordance with the present invention;

FIG. 9A is a side view of a portion of an alternative catheter assembly in accordance with the present invention, in a deployed position;

FIG. 9B is a side view of the catheter assembly of FIG. 9A in a retracted position;

FIG. 10 is a side view of a portion of an alternative catheter assembly in accordance with the present invention;

FIG. 11 is a side view of a portion of an alternative catheter assembly in accordance with the present invention;

FIGS. 12A and 12B are side views of a portion of an alternative catheter assembly in accordance with the present invention;

FIG. 20A is a simplified, side-sectional view of a pulmonary vein and associated ostium;

FIG. 20B is a simplified, side-view of a shaping wire in accordance with the present invention in an axially compressed position;

FIG. 20C is a simplified, side view of the shaping wire of FIG. 20B applied to the pulmonary vein of FIG. 20A;

FIG. 21A is a simplified, side-sectional view of a pulmonary vein and associated ostium;

FIG. 21B is a simplified, side view of an alternative shaping wire in an axially compressed position;

FIG. 21C is a simplified, side view of the shaping wire of FIG. 21B applied to the pulmonary vein of FIG. 21A;

FIG. 23 is a side view of a delivery catheter portion of the catheter assembly of FIG. 22;

FIG. 24C is an enlarged, side view of a portion of the delivery catheter of FIG. 23;

DESCRIPTION OF THE PREFERRED EMBODIMENTS

Figure 2A:
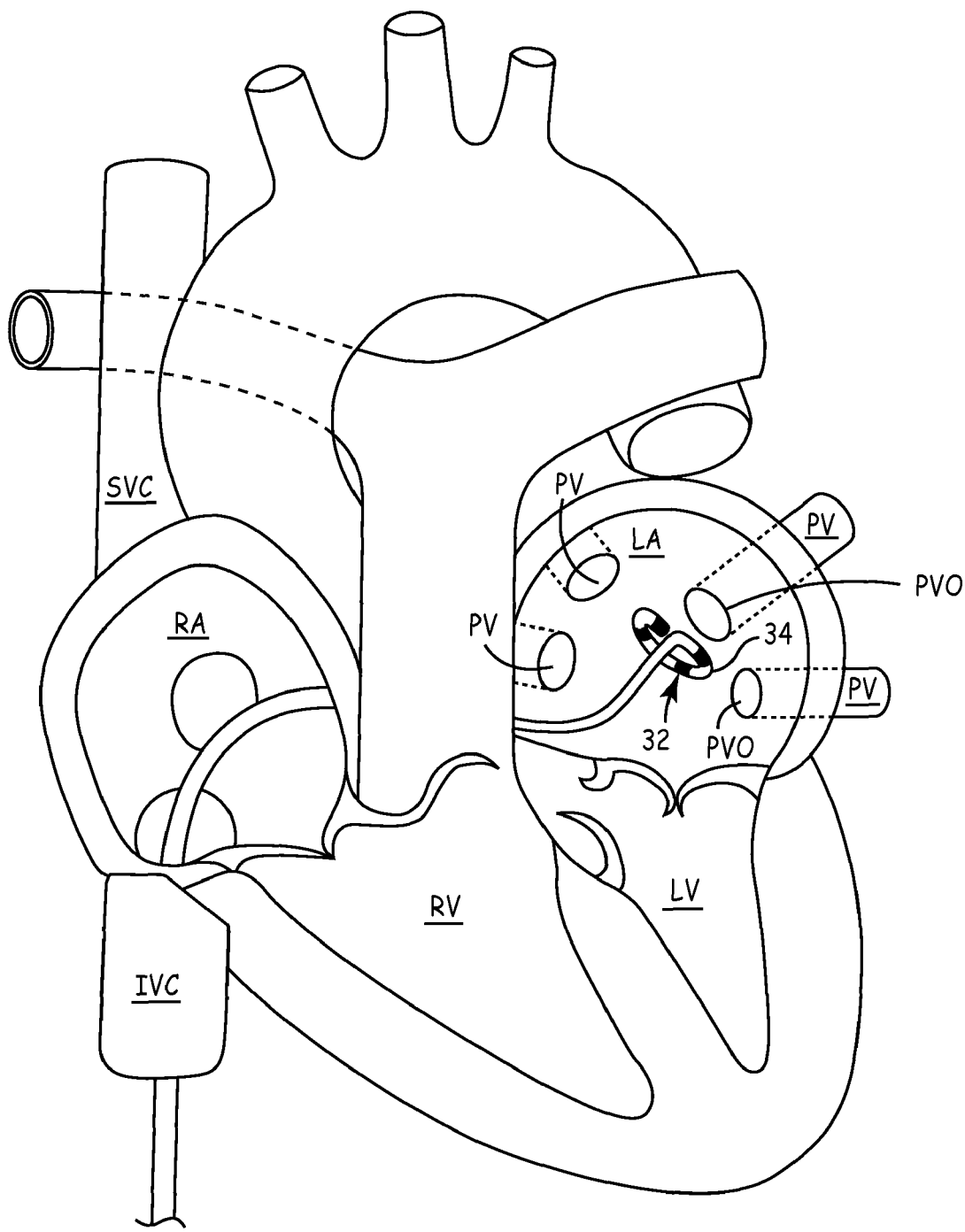
FIGS. 2A-2D illustrates use of the catheter assembly of FIG. 1A within a heart.

One preferred embodiment of a catheter assembly 20 in accordance with the present invention is shown in FIGS. 1A-1C. The catheter assembly 20 is comprised of a catheter body 22, a handle 24 and electrodes 26. As described in greater detail below, the catheter body 22 extends from the handle 24, and the electrodes 26 are disposed along a portion of the catheter body 22.

The catheter body 22 is defined by a proximal portion 28, an intermediate portion 30 and a distal portion 32, and includes a central lumen (not shown). Although not specifically shown, the catheter body may be configured for over-the-wire or rapid exchange applications. In one preferred embodiment, the proximal portion 28, the intermediate 30 and the distal portion 32 are integrally formed from a biocompatible material having requisite strength and flexibility for deployment within a heart. Appropriate materials are well known in the art and include polyamide.

The intermediate portion 30 extends from the proximal portion 28. The proximal portion 28 and the intermediate portion 30 are preferably flexible, so as to facilitate desired articulation during use. In general terms, however, the intermediate portion 30 defines a longitudinal axis L1. It should be recognized that in one position (shown in FIG. 1A), the longitudinal axis L1 extends linearly through the intermediate portion 30 and the proximal portion 28. Upon deployment, it may be that the proximal portion 28 and/or the intermediate portion 30 is forced to a curved or curvilinear orientation. With this in mind, the longitudinal axis L1 is more specifically defined as a center of the intermediate portion 30 adjacent a point of intersection between the distal portion 32 and the intermediate portion 30, as best shown in FIG. 1C.

The distal portion 32 extends from the intermediate portion 30 and forms a loop 34. In one preferred embodiment, the loop 34 is circular, formed in a plane transverse to the longitudinal axis L1. To this end, the distal portion 32 preferably includes a lateral segment 36. The lateral segment 36 extends in a generally lateral fashion from the intermediate portion 30. The loop 34 extends from the lateral segment 36 in an arcuate fashion, turning or revolving about a central loop axis C1 (shown best in FIG. 1B). While the loop 34 is shown in FIG. 1A as forming a single revolution about the central loop axis C1, the loop 34 may instead include a plurality of revolutions to define a spiral or coil. In the one preferred embodiment depicted in FIGS. 1A-1C, the central loop axis C1 is aligned with the longitudinal axis L1. Alternatively, however, the lateral segment 36 may be eliminated such that the loop 34 extends directly from the intermediate portion 30. Even further, the lateral segment 36 may be configured such that the central loop axis C1 is offset from the longitudinal axis L1. Regardless of the exact construction, however, the central loop axis C1 is preferably substantially parallel to the longitudinal axis L1.

As best shown in FIG. 1C, the loop 34 preferably extends to form a circle in a frontal plane. Alternatively, a variety of other shapes may also be useful. For example, as shown in FIG. 1D, a square-shaped loop is depicted. The loop 34 may further assume a triangular, rectangular, octagonal, or other closed shape. Returning to FIGS. 1A-1C, regardless of the exact shape, the loop 34 is preferably substantially closed and can be defined by a proximal end 40 and a distal end 42. To effectuate the preferred "closed" configuration of the loop 34, the distal end 42 is preferably adjacent the proximal end 40. In fact, the distal end 42 may contact the proximal end 40, although this relationship is not required. Alternatively, the distal end 42 may be longitudinally spaced from the proximal end 40. With this configuration, the distal portion 32 is preferably sufficiently flexible such that upon contact with a tissue wall, the distal end 42 will deflect proximally to a position adjacent the proximal end 40.

Regardless of the exact shape, the loop 34 preferably defines an enclosed area A greater than a size of an ostium (not shown) associated with a particular vessel to be isolated, as described in greater detail below. In one preferred embodiment, the catheter assembly 20 is configured to electrically isolate a pulmonary vein from the left atrium. With this one preferred application, where the loop 34 is circular, the loop 34 has a diameter in the range of approximately 10-20 mm, more preferably 15 mm, although other sizes, either greater or smaller, are acceptable.

The loop 34 may be formed in a variety of ways, such as by incorporating a preformed section of super elastic, shape memory material, such as Nitinol, with a loop configuration. To facilitate guiding of the distal portion 32 into a heart (not shown), the catheter assembly 20 may include a stylet (not shown) internally disposed within the catheter body 22. In an extended position, the stylet would extend through the distal portion 32, so as to render the loop 34 straight. Upon retraction of the stylet, the distal portion 32 would form the loop 34. Alternatively, the catheter assembly 20 may include a sheath (not shown) slidably receiving the catheter body 22. Prior to deployment, the distal portion 32 would be retracted within the sheath, rendering the loop 34 straight. Upon deployment from the sheath, the distal portion 32 would form the loop 34. Other similar approaches for providing the loop 34 are similarly acceptable.

The handle 24 is preferably sized to be grasped by a user and includes an electrical connector 44. The electrical connector provides electrical connections to the electrodes 26 carried by the distal portion 32. To this end, wire(s) (not shown) may extend within the central lumen (not shown) from the distal portion 32 to the handle 24.

The electrodes 26 are preferably of a type known in the art and are preferably a series of separate band electrodes spaced along the loop 34. Instead of, or in addition to, separate band electrodes, the electrodes 26 may include one or more spiral or coil electrodes, or one or more counter-electrodes. Additionally, the electrodes 26 are preferably non-thrombogenic, non-coagulum or char forming The electrodes 26 may be cooled by a separate source (not shown), such as a saline source. The electrodes 26 may be electrically isolated from one another, or some or all of the electrodes 26 may be electrically connected to one another. Preferably, however, at least one electrode 26 is provided. The electrodes 26 are preferably shaped and positioned such that during an ablation procedure, a continuous, closed therapeutically-effective lesion pattern is created. Preferably, the length of each of the electrodes 26 is about 4-12 mm, more preferably about 7 mm. The spacing between each of the electrodes 26 is preferably about 1-3 mm, and more preferably about 2 mm. Finally, to effectuate a continuous, closed lesion pattern, preferably one of the electrodes 26 is disposed at the proximal end 40 of the loop 34, and another of the electrodes 26 is disposed at the distal end 42. As previously described, it is not necessary that the loop segment 38 be formed such that the proximal end 40 and the distal end 42 are integral. Instead, a slight spacing may exist. With this in mind, the spacing or gap between the electrode 26 at the proximal 40 and the electrode 26 at the distal end 42 is preferably less than about 5 mm.

Figure 2B:
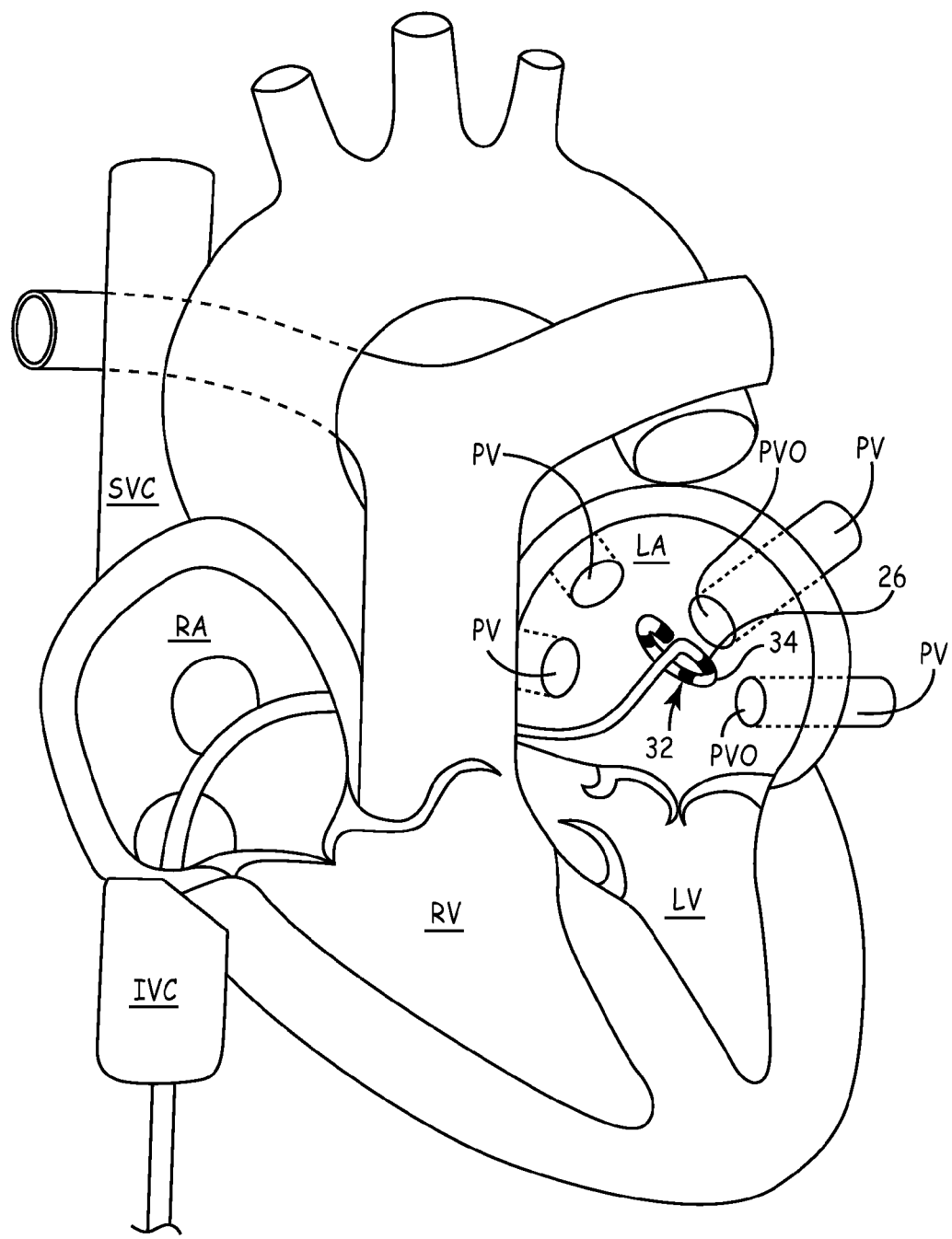

FIGS. 2A and 2B illustrate use of the catheter assembly 20 shown in FIGS. 1A-1C within a heart 50. As a point of reference, the heart 50 includes a right atrium RA, a left atrium LA, a right ventricle RV and a left ventricle LV. An inferior vena cava IVC and a superior vena cava SVC lead into the right atrium RA. The right atrium RA is separated from the left atrium LA by an interarterial septum (not shown). Finally, four pulmonary veins PV extend from the left atrium LA. Each of the pulmonary veins PV forms an ostium PVO in the left atrium LA wall. As previously described, during formation of the heart 50, it is possible that tissue of the left atrium LA may grow upwardly into one or more of the pulmonary veins PV. This left atrium LA tissue may spontaneously depolarize, resulting in atrial fibrillation. Notably, the heart 50 may be formed such that a separate ostium PVO is not formed for each individual pulmonary vein PV. In other words, a single pulmonary vein ostium PVO may be formed for two pulmonary veins PV. For example, a single pulmonary vein ostium PVO may be formed for both the left inferior pulmonary vein PV and the left superior pulmonary vein PV, with the two pulmonary veins PV bifurcating from the single ostium PVO.

As shown in FIG. 2A, electrical isolation of a pulmonary vein PV begins by directing the distal portion 32 of the catheter body 22 through the inferior vena cava IVC, into the right atrium RA through a puncture in the interarterial septum (not shown) and into the left atrium LA. Alternatively, the introduction of the distal portion 32 of the catheter body 22 into the right atrium RA is also suggested by passage of the distal portion 32 into the right atrium RA through the superior vena cava SVC. The loop 34 is positioned slightly spaced from the ostium PVO associated with the pulmonary vein PV to be treated. More particularly, the loop 34 is positioned such that the central loop axis C1 (FIG. 1B) is approximately aligned with a center of the pulmonary vein ostium PVO. The catheter body 22 is then advanced distally such that the loop 34 contacts the left atrium LA wall about the pulmonary vein ostium PVO in question, as shown in FIG. 2B. In other words, the catheter body 22 is advanced in a direction parallel with the central loop axis C1 such that the loop 34 contacts the left atrium LA wall, surrounding the pulmonary vein ostium PVO. Importantly, because the central loop axis C1 is parallel to the longitudinal axis L1, the catheter body 22 longitudinally supports advancement of the loop 34. In other words, the longitudinal axis L1 is effectively aligned with the pulmonary vein ostium PVO such that blood flow from the pulmonary vein PV acts along the longitudinal axis L1. Thus, the catheter body 22 limits deflection of the loop 34 otherwise caused by blood flow from the pulmonary vein PV.

Figure 2C:
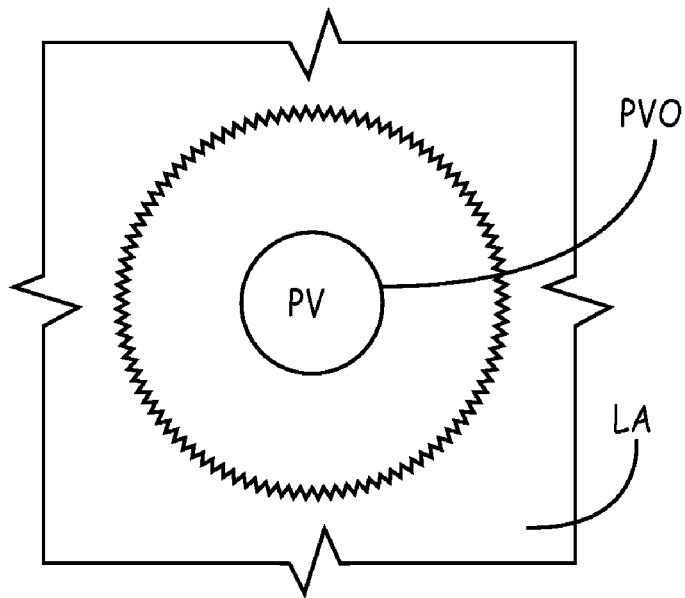
Figure 2D:
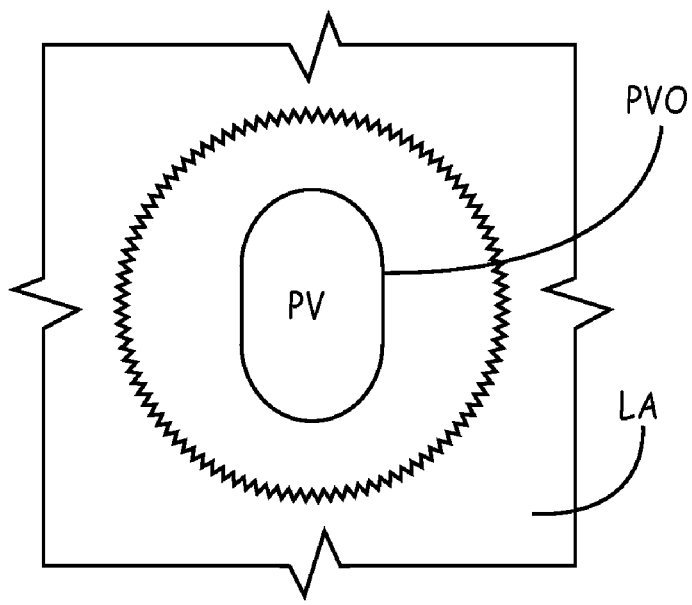

The electrodes 26 (shown best in FIGS. 1A-1C) are then energized to a sufficient level to ablate the contacted tissue, for example with an r.f. source. In one preferred embodiment, the electrodes 26 ablate the left atrium LA tissue for 30-120 seconds at a temperature in the range of approximately 60-70 degree C. As a result, a continuous, closed lesion pattern is formed around the pulmonary vein ostium PVO as shown in FIG. 2C. Pursuant to the above described catheter assembly 20 configuration, the lesion pattern is formed in a plane substantially perpendicular to the longitudinal axis L1. Notably, while the lesion pattern is shown as being only slightly larger than the pulmonary vein ostium PVO, the loop 34 (FIG. 1A) may be sized to produce an even larger ablation lesion pattern. To this end, where a single pulmonary vein ostium PVO is formed for two pulmonary veins PV, the resulting pulmonary vein ostium PVO may be elongated. As shown in FIG. 2D, then, the loop 34 (FIG. 1A) is configured to form a continuous, closed lesion pattern about the elongated-shaped pulmonary vein ostium PVO.

The continuous, closed lesion pattern electrically isolates the pulmonary vein PV from the left atrium LA. Any undesired electrical impulses generated in the pulmonary vein are effectively "stopped" at the lesion pattern, and will not propagate into the left atrium LA.

An alternative catheter assembly 60 is shown in FIGS. 3A and 3B. The catheter assembly 60 includes a catheter body 62, a handle (not shown) and electrodes 64. The catheter body 62 includes a proximal portion (not shown), an intermediate portion 66 and a distal portion 68. For ease of illustration, the handle and the proximal portion of the catheter body 22 are not shown in FIGS. 3A and 3B, it being understood that these components are similar to the handle 24 and the proximal portion 28 shown in FIG. 1A. Similar to the catheter body 22, the intermediate portion 66 extends from the proximal portion and defines a longitudinal axis L2. The distal portion 68 extends from the intermediate portion 66 and forms a loop or coil 70 substantially transverse to the longitudinal axis L2 and includes a plurality of loop segments 72A-72C. The coil 70 is formed such that each of the loop segments 72A-72C revolves about a central loop axis C2. In one preferred embodiment, the central loop axis C2 is aligned with the longitudinal axis L2 defined by the intermediate portion 66. Alternatively, the central loop axis C2 may be offset from the longitudinal axis L2. Regardless, the central loop axis C2 is preferably substantially parallel with the longitudinal axis L2.

Each of the loop segments 72A-72C preferably defines a different diameter. For example, the first loop segment 72A defines a diameter slightly larger than that of the second loop segment 72B; whereas the second loop segment 72B defines a diameter slightly greater than that of the third loop segment 72C. In this regard, while each of the loop segments 72A-72C are depicted as being longitudinally spaced (such that the loop 70 forms a multi-lane spiral or coil), the loop segments 72A-72C may instead be formed in a single plane (such that the loop 70 forms a unitary plane spiral or coil). While the loop segments 72A-72C extend distal the intermediate portion 66 so as to define a descending or decreasing diameter, an opposite configuration may also be employed. For example, FIG. 3C depicts a coil 70' having loop segments distally increasing in diameter.

Returning to FIGS. 3A and 3B, the electrodes 64 are similar to the electrodes 26 (FIG. 1A) previously described, and preferably are band electrodes disposed along the loop segments 72A-72C. In this regard, each of the loop segments 72A-72C includes electrodes 64A-64C, respectively. In one preferred embodiment, a power source (not shown) associated with the electrodes 64 is configured to individually energize the electrodes 64 to varying levels. Further, the electrodes 64 are preferably configured to provide feedback information indicative of tissue contact, such as by including a thermocouple.

The catheter assembly 60 is used in a fashion highly similar to the method previously described for the catheter assembly 20 (as shown, for example, in FIGS. 2A-2C). Thus, for example, the distal portion 68 of the catheter body 62 is directed within the left atrium LA (FIG. 2A) such that the loop 70 is disposed about a pulmonary vein ostium PVO. It should be understood that one or more of the loop segments 72A-72C may define a diameter (or area) that is less than a diameter (or area) of the pulmonary vein ostium PVO in question. For example, in the simplified cross-sectional view of FIG. 3D, the electrodes 64C associated with the third loop segment 72C (FIG. 3A) are not in contact with the left atrium LA wall, but instead are within the area defined by the pulmonary vein ostium PVO. Conversely, the electrodes 64B associated with the second loop segment 72B (FIG. 3A) and the electrodes 64A associated with the first loop segment (FIG. 3A) are in contact with the left atrium LA wall. To avoid potential collateral damage caused by full energization of the electrodes 64C not in contact with the left atrium LA wall, each of the electrodes 64A-64C are selectively energized with a low energy supply. The energy level is not sufficient to ablate contacted tissue, but provides a low energy measurement, such as through a thermocouple or other sensing device associated with each of the electrodes 64A-64C. If the sensing device detects a temperature rise, an indication is given that the particular energized electrode 64A, 64B or 64C is in contact with tissue of the left atrium LA. Following the low energy measurement procedure, only those electrodes determined to be in contact with the left atrium LA (for example, electrodes 64A and 64B) are powered to ablate a continuous, closed lesion pattern about the pulmonary vein ostium PVO, as previously described.

Another alternative embodiment of a catheter assembly 80 is shown in FIG. 4A. The catheter assembly 80 includes a catheter body 82, an electrode 84 and a locating device 86. For ease of illustration, only a portion of the catheter assembly 80 is shown, and catheter assembly 80 may further include a handle similar to the handle 24 associated with the catheter assembly 20 (FIG. 1A) previously described.

Catheter body 82 is defined by a proximal portion (not shown), an intermediate portion 88 and a distal portion 90. The intermediate portion 88 extends from the proximal portion and is defined by a proximal segment 92 and a distal segment 94. In a preferred embodiment, the distal segment 94 is preferably more flexible than the proximal segment 92. With this configuration, the distal segment 94 can more easily deflect relative to the proximal segment 92, thereby facilitating desired positioning of the distal portion 90 during deployment. In this regard, an internal pull wire (not shown) may be provided to effectuate desired deflection of the distal segment 94. Even further, an anchor 96 is preferably included for facilitating a more radical displacement of the distal portion 90 relative to the intermediate portion 88.

As with previous embodiments, the intermediate portion 88 defines a longitudinal axis L3. Once again, where the intermediate portion 88 is axially aligned with the proximal portion (not shown), the longitudinal axis L3 is linear along the intermediate portion 88 and the proximal portion. However, because the intermediate portion 88 is preferably bendable relative to the proximal portion, and further because the distal segment 94 may bend relative to the proximal segment 92, the longitudinal axis L3 is more succinctly defined by the intermediate portion 88 at the point of intersection between the intermediate portion 88 and the distal portion 90.

Similar to the catheter assembly 20 (FIG. 1A) previously described, the distal portion 90 preferably forms a loop 98. The loop 98 may include one or more loop segments (one is shown in FIG. 4A), with each loop segment revolving around a central loop axis C3. The loop 98 is formed substantially transverse to the longitudinal axis L3, with the central loop axis C3 preferably aligned with the longitudinal axis L3. Alternatively, the central loop axis C3 may be slightly offset from the longitudinal axis L3. Regardless, the central loop axis C3 is preferably parallel with the longitudinal axis L3.

The electrode 84 is shown in FIG. 4 as being a continuous coil electrode. Alternatively, a plurality of spaced, band electrodes or counter-electrodes may be used.

Finally, the locating device 86 includes a tip 100 configured to extend distal the loop 98. In one preferred embodiment, the locating device 86 is integrally formed with the catheter body 82, extending from the distal portion 90. Alternatively, the locating device 86 may be a separate body. Regardless, the tip 100 extends distal the distal portion 90, and is aligned with the central loop axis C3 defined by the loop 98. The tip 100 preferably has a diameter less than a diameter of a pulmonary vein, and a length in the range of approximately 1-15 mm. Further, as shown in FIG. 4, the tip 100 may include a series of mapping electrodes 102. The mapping electrodes 102 are electrically connected to an external recording system (not shown) for providing information indicative of tissue polarization.

Figure 4B:
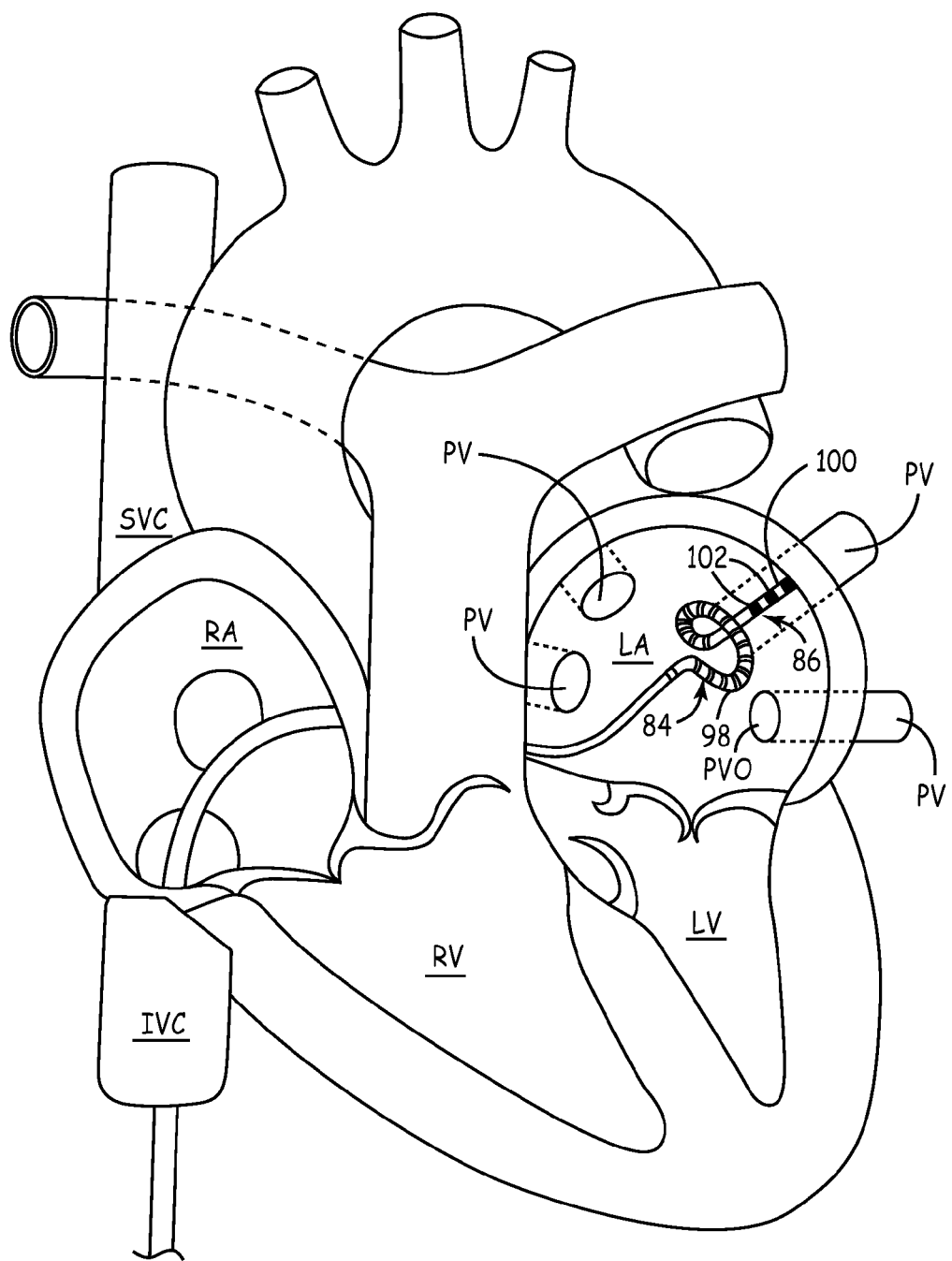
FIG. 4B illustrates placement of the catheter assembly of FIG. 4A within the left atrium of a heart.

As shown in FIG. 4B, during use, the catheter assembly 80 is directed into the left atrium LA as previously described. The locating device 86, and in particular the tip 100, is then used to locate the pulmonary vein ostium PVO. Once located, the tip 100 is inserted into the pulmonary vein PV, effectively centering the loop 98 around the pulmonary vein ostium PVO. Where the tip 100 includes the mapping electrodes 102, a mapping procedure can be performed, whereby information indicative of tissue activity nearby the mapping electrodes 102 is provided. During this mapping procedure, a determination can be made as to whether the particular pulmonary vein PV is generating undesired electrical impulses. Where it is determined that, in fact, tissue in the pulmonary vein PV is spontaneously depolarizing, the electrode 84 is energized to form the continuous, closed lesion pattern about the pulmonary vein ostium PVO as previously described.

Yet another alternative embodiment of a catheter assembly 110 in accordance with the present invention is shown in FIG. 5. The catheter assembly 110 is highly similar to the catheter assembly 80 (FIG. 4A) and includes a catheter body 112, electrodes 114 and a locating device 116. The catheter body 112 includes a proximal portion (not shown) an intermediate portion 88 defining a longitudinal axis L4 and a distal portion 120. The distal portion 120 extends from the intermediate portion 118 and forms a loop 122 substantially transverse to the longitudinal axis L4. In this regard, the loop 122 revolves about a central loop axis C4. In one preferred embodiment, the central loop axis C4 is aligned with the longitudinal axis L4. Alternatively, the central loop axis C4 is offset from, but substantially parallel with, the longitudinal axis L4. The electrodes 114 (shown as spaced band electrodes) are disposed along the loop 122 for forming a continuos, closed lesion pattern.

The locating device 116 includes a tip 124 that extends distal the loop 122. In one preferred embodiment, the locating device 116 is integrally formed with the catheter body 112 and includes mapping electrodes 126 connected to an external recording device (not shown). Alternatively, the locating device 116 may be a separate body. As shown in FIG. 5, the tip 124 forms a descending diameter coil, generally aligned with the central loop axis C4. By providing a coil configuration for the tip 124, the tip 124 facilitates a more positive centering of the loop 122 about a pulmonary vein ostium PVO (FIG. 4B). In one preferred embodiment, the tip 124 defines a maximum diameter approximating a diameter of a pulmonary vein. When inserted within a pulmonary vein, then, the tip 124 effectively lodges along the pulmonary vein wall. This, in turn, positions the loop 122 in a more central fashion about the associated ostium. Further, by providing the mapping electrodes 126, the locating device 116 additionally serves as a mapping device for evaluating a particular pulmonary vein.

It should be recognized that other devices can be provided to assist in centering the ablation loop about the pulmonary vein ostium. For example, yet another alternative embodiment of a catheter assembly 130 is depicted in FIG. 6. The catheter assembly includes a catheter body 132, electrodes 134, a balloon 136 and a locating device 138. The catheter body 132 is similar to those previously described, and includes a proximal portion (not shown) an intermediate portion 140 defining a longitudinal axis L5 and a distal portion 142. The distal portion 142 extends from the intermediate portion 140 and forms a loop 144 substantially transverse to the longitudinal axis L5. The loop 144 revolves about a central loop axis C5, that, in one preferred embodiment, is aligned with the longitudinal axis L5. The balloon 136 is disposed along the distal portion 142 distal the loop 144. In one preferred embodiment, the balloon 136 is fluidly connected to a fluid source (not shown), such as a pressurized reservoir of saline, by a lumen (not shown) formed within the catheter body 132. Finally, the locating device 138 includes a tip 146 extending distal the loop 144. In one preferred embodiment, as shown in FIG. 6, the locating device 138 is integrally formed with the catheter body 132, with the tip 146 extending distal the balloon 136. Alternatively, the locating device 138 may be a separate body, and the tip 146 may be positioned between the loop 144 and the balloon 136. Regardless, the tip 146 preferably includes mapping electrodes 148.

During use, the locating device 138 is used to locate a pulmonary vein PV (FIG. 4B) via the tip 146. The tip 146 axially inserted into the pulmonary vein PV. The mapping electrodes 148 may then be used to ascertain whether tissue in the pulmonary vein PV is spontaneously generating unexpected electrical impulses. Upon determining that the pulmonary vein PV requires electrical isolation, the catheter body 132 is deployed such that the loop 144 contacts the left atrium LA (FIG. 4B) wall (as previously described). The balloon 136 is inflated such that it engages the pulmonary vein PV wall. Once inflated, the balloon 136 positively centers the loop 144 about the pulmonary vein ostium PVO (FIG. 4B).

Yet another alternative embodiment of a catheter assembly 160 is shown in FIG. 7. The catheter assembly 160 includes a catheter body 162, electrodes 164, a wire basket 166 and a locating device 168. As with previous embodiments, the catheter body 162 includes a proximal portion (not shown), an intermediate portion 170 defining a longitudinal axis L6 and a distal portion 172. The distal portion 172 extends from the intermediate portion 170 and forms a loop 174 transverse to the longitudinal axis L6. In this regard, the loop 174 revolves around a central loop axis C6 that, in one preferred embodiment, is aligned with the longitudinal axis L6.

The wire basket 166 is maintained by the distal portion 172 distal the loop 174. The wire basket 166 may be radially extended and retracted via a pull wire or similar activation device extending through a lumen (not shown) formed within the catheter body 162.

Finally, the locating device 168 includes a tip 176 positioned distal the loop 174. In one preferred embodiment, the locating device 168 is integrally formed with the catheter body 162 and includes mapping electrodes 178. Alternatively, the locating device 168 may be a separate body, and the tip 176 may be disposed between the wire basket 166 and the loop 174.

During use, the catheter assembly 160 functions in a fashion highly similar to the catheter assembly 130 (FIG. 6) previously described. The locating device 168, and in particular the tip 176, is used to locate and map a pulmonary vein PV (FIG. 4B). The loop 174 is maneuvered into contact with the left atrium LA (FIG. 4B) wall. The wire basket 166 is then radially deployed so as to engage the pulmonary vein PV wall. In this deployed position, the wire basket 166 serves to positively center the loop 174 about the pulmonary vein ostium PVO (FIG. 4B).

Yet another alternative embodiment of a catheter assembly 190 is shown in FIG. 8. The catheter assembly 190 includes a catheter body 192 (shown partially in FIG. 8), electrodes 194, a locating device 196 and a guide catheter or sheath 198. As described in greater detail below, the sheath 198 coaxially maintains the catheter body 192 and the locating device 196 such that each of the catheter body 192 and the locating device 196 are slidable between a retracted position and a deployed position (shown in FIG. 8).

The catheter body 192 is virtually identical to the catheter body 62 (FIG. 3A) previously described and includes a proximal portion (not shown), an intermediate portion 200 defining a longitudinal axis L7 and a distal portion 202. The distal portion 202 extends from the intermediate portion 200 and forms a coil or plurality of loops 204 substantially transverse to the longitudinal axis L7. Alternatively, the coil 204 may form a single loop. The coil 204 revolves around a central loop axis C7 that, in one preferred embodiment, is aligned with the longitudinal axis L7. The distal portion 202, and in particular the coil 204, is preferably sufficiently flexible so as to assume a relatively straight configuration when retracted within the sheath 198. Further, the distal portion 202 includes a shape memory characteristic such that when deployed from the sheath 198, the distal portion 202 forms the coil 204 as shown in FIG. 8.

The electrodes 194 are identical to those previously described and preferably comprise band electrodes disposed along the coil 204. Alternatively, a continuous coil electrode or counter-electrode may be provided.

The locating device 196 is relatively rigid and includes a shaft 206 defining a tip 208 that preferably maintains mapping electrodes 210. The shaft 206 is sized to be slidably received within a lumen (not shown) in the sheath 198. As shown in FIG. 8, the tip 208 preferably assumes a coil shape with decreasing diameter. Alternatively, the tip 208 may be substantially straight. Preferably, however, the tip 208 is sufficiently flexible such that upon retraction into the sheath 198, the tip 208 assumes a relatively straight form. Additionally, the tip 208 has a shape memory characteristic such that upon deployment from the sheath 198, the tip 208 assumes the coiled shape shown in FIG. 8. For example, the tip 208 may include stainless steel or Nitinol core wires. Further, the tip 208 may be formed from a shape memory alloy of Nitinol that forms the coil shape when heated above a certain temperature. The heat may be achieved through resistive heating of the wire directly, or by surrounding the wire with a tubular heater.

The sheath 198 includes a proximal end (not shown) and a distal end 212, and forms at least one central lumen (not shown) sized to maintain the catheter body 192 and the locating device 196. Alternatively, a separate lumen may be provided for each of the catheter body 192 and the locating device 196. Regardless, the sheath 198 is configured to slidably maintain each of the catheter body 192 and the locating device 196 in a relatively close relationship. In one preferred embodiment, the sheath 198 is formed of a relatively soft material such as 35D or 40D Pebex.

As described above, each of the catheter body 192 and the locating device 196 are slidable relative to the sheath 198. In a deployed position (depicted in FIG. 8), the distal portion 202 of the catheter body 192 and the tip 208 of the locating device 196 extend distally from the sheath 198. More particularly, the locating device 196 is positioned such that the tip 208 is distal the coil 204. In this extended position, the tip 208 is essentially aligned with the central loop axis L7.

During use, the catheter body 192 and the locating device 196 are retracted within the sheath 198. The sheath 198 is then guided to the left atrium LA (FIG. 4B). The catheter body 192 and the locating device 196 are deployed from the sheath 198. More particularly, the distal portion 202 of the catheter body 192 and the tip 208 of the locating device 196 are extended from the distal end 212 of the sheath 198 (as shown in FIG. 8). A locking device (not shown) is preferably provided to secure the catheter assembly 190 in the deployed position. As previously described, upon deployment, the distal portion 202 forms the coil 204, whereas the tip 208 preferably assumes a coil shape. The tip 208 locates and is directed axially into a pulmonary vein PV as previously described. The mapping electrodes 210 sample electrical activity of the pulmonary vein tissue. If the mapping procedure determines that the pulmonary vein PV requires electrical isolation, the sheath 198 is guided in a direction along the central loop axis C7 until the coil 204 contacts the left atrium LA (FIG. 4B) wall about the pulmonary vein ostium PVO (FIG. 4B). Because the catheter body 192 and the locating device 196 are directly connected by the sheath 198, the tip 208 effectively positively centers the loop 204 about the pulmonary vein ostium PVO. The electrodes 194 may be selectively energized with a low energy supply to determine which of the electrodes 194 are in contact with tissue of the left atrium LA. Some or all of the electrodes 194 are then energized to ablate a continuous, closed lesion pattern about the pulmonary vein ostium PVO, thereby electrically isolating the pulmonary vein PV from the left atrium LA.

While the catheter assembly 190 has been described as including the sheath 198 to maintain the catheter body 192 and the locating device 196, the sheath 198 may be eliminated for example, the catheter body 192 may alternatively be configured to include lumen (not shown) sized to slidably receive the locating device 192. In this regard, the locating device 192 may serve as a guide wire, with the catheter body 192 riding over the locating device 192 much like an over-the-wire catheter configuration commonly known in the art. Even further, the catheter body 192 may include a rapid exchange design characteristic for quick mounting to removal from the locating device 190.

Yet another alternative embodiment of a catheter assembly 220 is shown in FIGS. 9A and 9B. The catheter assembly 220 includes a catheter body 222 (shown partially in FIGS. 9A and 9B), electrodes 224, stylets 226 and a locating device 228. The electrodes 224 are disposed along a portion of the catheter body 222. The stylets 226 are slidably maintained within the catheter body 222. Finally, the locating device 228 is slidably maintained by the catheter body 222.

The catheter body 222 is similar to those previously described and includes a proximal portion (not shown), an intermediate portion 230, defining a longitudinal axis L8, and a distal portion 232. The distal portion 232 forms a loop 234 substantially transverse to the longitudinal axis L8. The loop 234 revolves around a central loop axis C8 which, in one preferred embodiment, is aligned with the longitudinal axis L8. The distal portion 232 is preferably sufficiently flexible so as to be relatively straight in a retracted position (FIG. 9B). Further, the distal portion 232 has a shape memory characteristic such that the distal portion 232 forms the loop 234 in a deployed position (FIG. 9A). For example, the catheter body 222 may be formed of a super elastic, shape memory Nitinol alloy.

Each of the stylets 226 are relatively rigid shafts sized to be slidably received within lumens (not shown) formed by the catheter body 222. To this end, as shown in FIG. 9A, in a deployed position, the stylets 226 are proximal the distal portion 232 such that the distal portion 232 is allowed to form the loop 234. Conversely, in a retracted position (FIG. 9B) the stylets 226 extend into the distal portion 232, thereby rendering the distal portion 232 substantially straight.

The electrodes 224 are identical to those previously described and preferably comprise band electrodes disposed along the loop 234. Alternatively, a continuous coil electrode or counter electrode may be provided.

The locating device 228 includes a shaft 236 having a tip 238. Similar to previous embodiments, the tip 238 is preferably coil shaped, and includes mapping electrodes 240. In this regard, the tip 238 is preferably sufficiently flexible such that in the retracted position (FIG. 9B), the tip 238 is rendered relatively straight by the catheter body 222. Conversely, in the deployed position (FIG. 9A), the tip 238 assumes the coiled shape. Alternatively, the tip 238 may be substantially straight in the deployed position.

The catheter assembly 220 is used in a manner highly similar to that previously described. The catheter assembly 220 is initially placed in the retracted position (FIG. 9B), whereby the stylets 226 are maneuvered distally to straighten the distal portion 232. Further, the locating device 228 is retracted within the catheter body 222 such that tip 238 is proximal the distal portion 232 and is rendered relatively straight. In this retracted position, the catheter assembly 222 can more easily be directed into the left atrium LA (FIG. 4B) as previously described. Once in the left atrium LA, the catheter assembly 220 is maneuvered to the deployed position (FIG. 9A), whereby the stylets are moved proximally such that the distal portion 232 forms the loop 234. Further, the locating device 228 is maneuvered distally relative to the catheter body 222 such that the tip 238 extends distal the loop 234. In the deployed position, the locating device 228 is maneuvered in a generally axial fashion to locate and extend into a pulmonary vein PV. The mapping electrodes 240 map the pulmonary vein tissue (FIG. 4B). Where the mapping procedure indicates that the pulmonary vein PV requires electrical isolation, the catheter assembly 220 is advanced such that the loop 234 surrounds the pulmonary vein ostium PVO (FIG. 4B). More particularly, the catheter assembly 220 is advanced in the direction of the central loop axis C8. Once again, the unique configuration of the catheter assembly 220 facilitates movement in an axial direction (relative to the pulmonary vein ostium PVO) as opposed to a radial, sliding direction required by previous ablation catheter designs. Notably, because the locating device 228 is directly connected to the catheter body 222, the locating device 228 facilitates positive centering of the loop 234 about the pulmonary vein ostium PVO. The electrodes 224 are then energized to ablate a continuous, closed lesion pattern about the pulmonary vein ostium PVO, thereby electrically isolating the pulmonary vein PV.

Yet another alternative embodiment of the catheter assembly 250 in accordance with the present invention is shown in FIG. 10. The catheter assembly 250 includes a catheter body 252 (shown partially in FIG. 10), electrodes 254, a locating device 256 and a guide catheter or sheath 258. As described in greater detail below, the sheath 258 coaxially maintains the catheter body 252 and the locating device 256 such that each of the catheter body 252 and the locating device 256 are slidable between a retracted position and a deployed position (shown in FIG. 10).

The catheter body 252 is virtually identical to the catheter body 62 (FIG. 3A) previously described and includes a proximal portion (not shown), an intermediate portion 260 defining a longitudinal axis L9 and a distal portion 262. The distal portion 262 extends from the intermediate portion 260 and forms a coil or loops 264 substantially transverse to the longitudinal axis L9. Alternatively, the coil 264 may form a single loop. The coil 264 revolves around a central loop axis C9, that, in one preferred embodiment, is aligned with the longitudinal axis L9. The distal portion 262, and in particular the coil 264, is preferably sufficiently flexible so as to assume a relatively straight configuration when retracted within the sheath 258. Further, the distal portion 262 includes a shape memory characteristic such that when deployed from the sheath 258, the distal portion 262 forms the coil 264 as shown in FIG. 10.

The electrodes 254 are identical to those previously described and preferably comprise band electrodes disposed along the coil 264. Alternatively, a continuous coil electrode or counter-electrode may be provided.

The locating device 256 includes a shaft 266 and a balloon 268. The shaft 266 includes a distal portion 270 and a tip 272. The distal portion 270 preferably forms an expansion joint 274. The tip 272 is distal the expansion joint 274 and preferably maintains mapping electrodes 276. The balloon 268 is sealed to the distal portion 270 of the shaft 266 about the expansion joint 274. In this regard, the expansion joint 274 is configured to be manipulated between a contracted position (FIG. 10) and an expanded position. In the expanded position, the expansion joint 274 extends axially so as to collapse the balloon 268. When collapsed, the balloon 268 can more easily be retracted within the sheath 258.

The sheath 258 includes a proximal end (not shown) and a distal end 278, and forms at least one central lumen (not shown) sized to maintain the catheter body 252 and the locating device 256. Alternatively, a separate lumen may be provided for each of the catheter body 252 and the locating device 256. Regardless, the sheath 258 is configured to slidably maintain each of the catheter body 252 and the locating device 256 in relatively close relationship. In one preferred embodiment, the sheath 258 is formed of a relatively soft material such as 35D or 40D Pebex.

As described above, each of the catheter body 252 and the locating device 256 are slidable relative to the sheath 258. In a deployed position (depicted in FIG. 10), the distal portion 262 of the catheter body 252 and the distal portion 270 of the locating device 256 extend distally from the sheath 258. More particularly, the coil 264 is positioned distal the distal end 278 of the sheath 258. Further, the distal portion 270, including the balloon 268, of the locating device 256 is positioned distal the coil 264. In this position, the distal portion 270 is essentially aligned with the central loop axis L9.

Prior to use, the catheter body 252 and the locating device 256 are retracted within the sheath 258. The sheath 258 is then guided to the left atrium LA (FIG. 4B). The catheter body 252 and the locating device 256 are deployed from the sheath 258. More particularly, the distal portion 262 of the catheter body 252 and the distal portion 270 of the locating device 256 are extended from the distal end 278 of the sheath 258 (as shown in FIG. 10). A locking device (not shown) is preferably provided to secure the catheter assembly 250 in the deployed position. As previously described, upon deployment, the distal portion 262 of the catheter body 252 forms the coil 264. The distal portion 270 of the locating device 256, including the balloon 268, is positioned distal the coil 264. The tip 272 locates and is directed axially into a pulmonary vein PV (FIG. 4B) as previously described. The mapping electrodes 276 sample electrical activity of the pulmonary vein tissue. If the mapping procedure determines that the pulmonary vein PV requires electrical isolation, the sheath 258 is guided in a direction along the central loop axis C9 until the coil 264 contacts the left atrium LA wall about the pulmonary vein ostium PVO (FIG. 4B). The expansion joint 274 is contracted and the balloon 268 inflated. Once inflated, the balloon 268 engages the pulmonary vein PV. Because the catheter body 252 and the locating device 256 are directly connected by the sheath 258, the balloon 268 effectively positively centers the coil 264 about the pulmonary vein ostium PVO. The electrodes 254 may be selectively energized with a low-energy supply to determine which of the electrodes 254 are in contact with the tissue of the left atrium LA. Some or all of the electrodes 254 are then energized to ablate a continuous, closed lesion pattern about the pulmonary vein ostium PVO, thereby electrically isolating the pulmonary vein PV from the left atrium LA.

Yet another alternative embodiment of a catheter assembly 290 is shown in FIG. 11. The catheter assembly 290 is highly similar to the catheter assembly 250 (FIG. 10) previously described, and includes a catheter body 292, electrodes 294, a locating device 296 and a guide catheter or sheath 298. The sheath 298 coaxially maintains the catheter body 292 and the locating device 296 such that each of the catheter body 292 and the locating device 296 are slidable between a retracted position and a deployed position (shown in FIG. 11).

The catheter body 292 includes a proximal portion (not shown), an intermediate portion 300 defining a longitudinal axis L10 and a distal portion 302. The distal portion 302 extends from the intermediate portion 300 and forms a coil or plurality of loops 304 substantially transverse to the longitudinal axis L10. Alternatively, the coil 304 may form a single loop. The coil 304 revolves around a central loop axis C10, that, in one preferred embodiment, is aligned with the longitudinal axis L10. The distal portion 302, and in particular the coil 304, is preferably sufficiently flexible so as to assume a relatively straight configuration when retracted within the sheath 298. Further, the distal portion 302 includes a shape memory characteristic such that when deployed from the sheath 298, the distal portion 302 forms the coil 304 as shown in FIG. 11.

The electrodes 294 are identical to those previously described and preferably comprise band electrodes disposed along the coil 304. Alternatively, a continuous coil electrode or counter-electrode may be provided.

The locating device 296 includes a shaft 306 and a wire basket 308. The shaft 306 includes a distal portion 310 and a tip 312. The distal portion 310 forms an expansion joint 314. The tip 312 preferably maintains mapping electrodes 316. The wire basket 308 is secured to the distal portion 310 about the expansion joint 314. With this configuration, the expansion joint 314 can be manipulated between an expanded position in which the wire basket 308 is relatively flat and a contracted position (FIG. 11) in which the wire basket 308 expands radially.

The sheath 298 is highly similar to previous embodiments and includes a proximal end (not shown) and a distal end 318, and forms at least one central lumen (not shown) sized to maintain the catheter body 292 and the locating device 296. Alternatively, a separate lumen may be provided for each of the catheter body 292 and the locating device 296. Regardless, the sheath 298 is configured to slidably maintain each of the catheter body 292 and the locating device 296 in a relatively close relationship.

As described above, each of the catheter body 292 and the locating device 296 are slidable relative to the sheath 298. In a deployed position (depicted in FIG. 11), the distal portion 302 of the catheter body 292 and the distal portion 310 of the locating device 296 extend distally from the sheath 298. More particularly, the catheter body 292 is positioned such that the coil 304 is distal the distal end 318. Further, the distal portion 310 of the locating device 296 is distal the coil 304.

During use, the catheter assembly 290 functions in a manner highly similar to the catheter assembly 250 (FIG. 10) previously described. However, the wire basket 308 is used to positively center the coil 304 about a pulmonary vein ostium PVO instead of the balloon 268 (FIG. 10) previously described.

Yet another alternative embodiment of the catheter assembly 330 is shown in FIGS. 12A and 12B. The catheter assembly 330 includes a catheter body 332 (shown partially in FIGS. 12A and 12B), a wire basket 334, a locating device 336 and a stylet or guide wire 338. The wire basket 334 is secured to the catheter body 332. The locating device 336 is preferably integrally formed with the catheter body 332 and includes a balloon 340. Finally, the guide wire 338 is slidably disposed within a central lumen (not shown) in the catheter body 332 and the locating device 336.

The catheter body 332 includes a proximal portion (not shown), an intermediate 342 defining a longitudinal axis L11 and a distal portion 344. The distal portion 344 maintains a proximal collar 346 and a distal collar 348. In a preferred embodiment, the proximal collar 346 is slidable relative to the distal collar 348.

The wire basket 334 is secured to the distal portion 344 by the proximal collar 346 and the distal collar 348. Further, the wire basket 334 includes a plurality of individual wire struts 350 each maintaining an electrode 352. In a preferred embodiment, the wire struts 350 are preferably tubular and are fluidly connected to a cooling source. The electrodes 352 are preferably disposed along the wire struts 350, respectively, slightly distal of a central position. With this configuration, the wire basket 334 can be maneuvered between a retracted position (FIG. 12A) and an expanded position (FIG. 12B) with movement of the proximal collar 346 relative to the distal collar 348. Notably, in the expanded position of FIG. 12B, the wire basket 334 positions the electrodes 352 so as to form a loop transverse to the longitudinal axis L11. More particularly, the loop formed in the expanded position revolves around a central loop axis C11, that, in one preferred embodiment, is aligned with the longitudinal axis L11.

The electrodes 352 are identical to those previously described and preferably comprise band electrodes disposed along the wire basket 334.

The locating device 336 extends distal the distal collar 348, and maintains the balloon 340 and mapping electrodes 354. The balloon 340 is fluidly connected to an inflation source (not shown) by a lumen (not shown) formed within the catheter body 332. As shown in FIGS. 12A and 12B, the balloon 340 is preferably positioned distal the wire basket 334. Further, the mapping electrode 354 is positioned distal the balloon 340.

Prior to use, the catheter assembly 330 is positioned in the retracted position shown in FIG. 12A. The guide wire 338 is guided to the left atrium LA (FIG. 4B) and into a pulmonary vein PV (FIG. 4B). The catheter body 332, including the locating device 336, are guided over the guide wire 338 to a point adjacent the pulmonary vein. The catheter body 332 is then advanced such that the locating device 336 enters the pulmonary vein PV. The mapping electrodes 354 sample electrical activity of the pulmonary vein tissue. If the mapping procedure determines that the pulmonary vein PV requires electrical isolation, the catheter assembly 330 is maneuvered to the expanded position shown in FIG. 12B, whereby the wire basket 334 expands radially. The catheter body 332 is then advanced axially toward the pulmonary vein such that the wire basket 334 contacts the left atrium LA about the pulmonary vein ostium PVO (FIG. 4B). The balloon 340 is then inflated so as to engage the pulmonary vein PV. Once inflated, the balloon 340 effectively centers the wire basket 334, and thus the electrodes 352, about the pulmonary vein ostium PVO. The electrodes 352 are then energized to ablate a continuous, closed lesion pattern about the pulmonary vein ostium PVO, thereby electrically isolating the pulmonary vein PV from the left atrium LA. If necessary, the individual wire struts 350 are cooled, such as by forcing a cooling liquid through the wire struts 350. The balloon 340 is deflated and the wire basket 334 maneuvered to the contracted position (FIG. 12A). The entire catheter assembly 330 may then be removed from the patient. Alternatively, the catheter body 332 may be retracted from the patient along the guide wire 338 and replaced with a separate catheter device (not shown). To this end, the catheter body 332 may be configured to provide a rapid exchange feature, as would be apparent to one of ordinary skill.

Figure 13A:
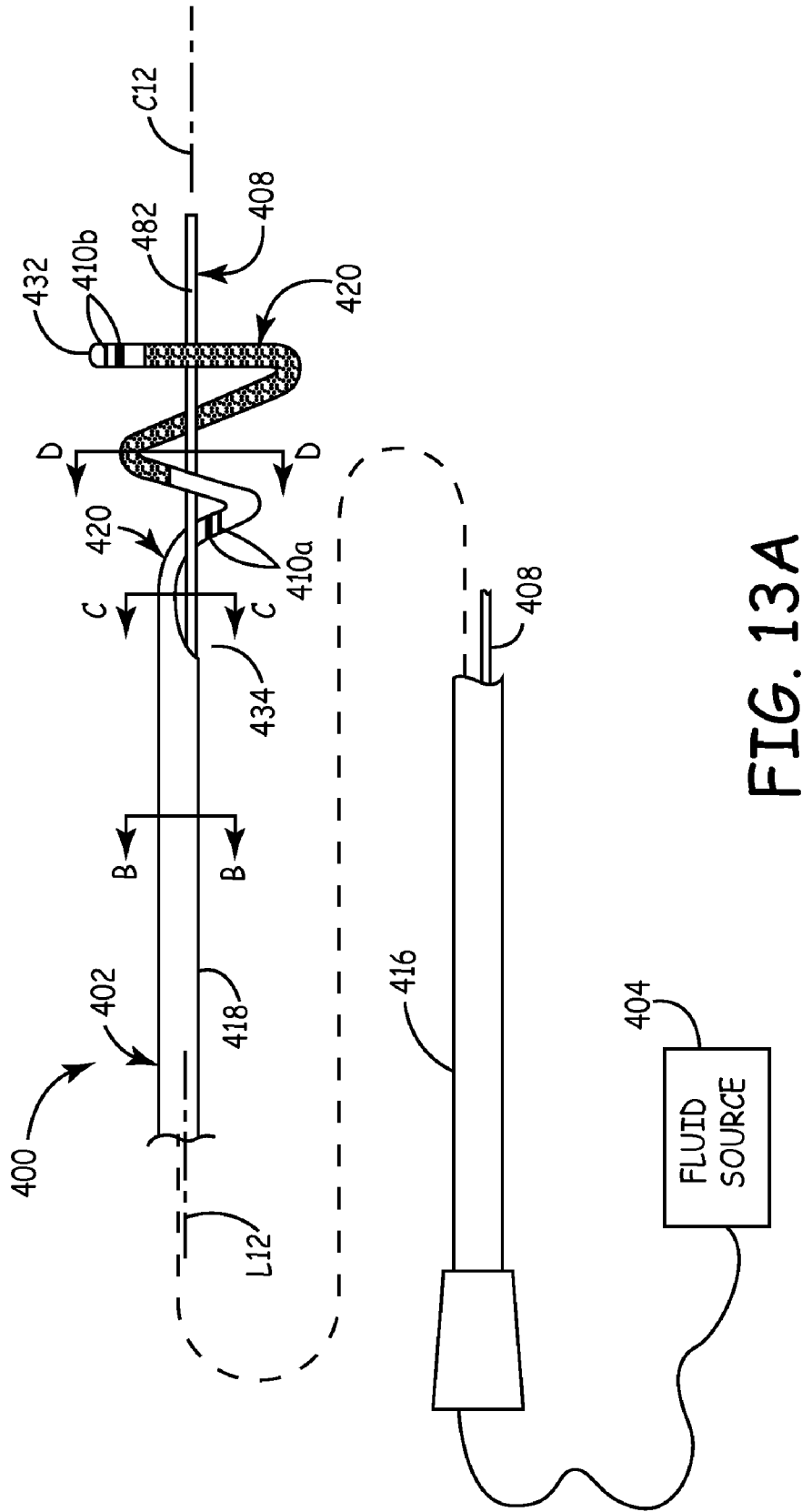
FIG. 13A is a side view of an alternative catheter assembly in accordance with the present invention.

Yet another alternative embodiment of a catheter assembly 400 is shown in FIGS. 13A-13E. With reference to FIG. 13A, the catheter assembly 400 includes a catheter body 402, a fluid source 404, a shaping wire 406 (hidden in FIG. 13A), a guide wire 408 and first and second sensing electrode pairs 410a and 410b. The fluid source 404 is fluidly connected to a lumen formed by the catheter body 402. The shaping wire 406 and the guide wire 408 are coaxially and slidably maintained by the catheter body 402 such that each of the shaping wire 406 and the guide wire 408 are slidable between a retracted position and a deployed position (shown in FIG. 13A). Finally, the sensing electrodes 410a, 410b are secured to a portion of the catheter body 402.

The fluid source 404 is shown schematically in FIG. 13A, and can assume a wide variety of forms. The fluid source 404 maintains an appropriate volume of a conductive liquid or ionic fluid, such as a hypertonic saline solution, and includes a pump (not shown). The pump is controllable to provide a desired flow rate of the liquid to the catheter body 402.

The catheter body 402 includes a proximal portion 416, an intermediate portion 418, and a distal portion 420. Construction of the catheter body 402 is described in greater detail below. In general terms, and as shown in FIG. 13A, the distal portion 420 extends from the intermediate portion 418 and forms, or is formed to, a coil or helix (e.g., conical or cylindrical). Further, the distal portion 420 defines an ablation section 422. The ablation section 422 forms, or is formed to, a loop of at least one revolution. As with previous embodiments, the loop formed at or by the ablation section 422 revolves around a central loop axis C12, that is substantially parallel with, preferably aligned with, a longitudinal axis L12 defined by the intermediate portion 418. Alternatively stated, the loop formed at or by the ablation section 422 extends transversely relative to the longitudinal axis L12.

Figure 13B:
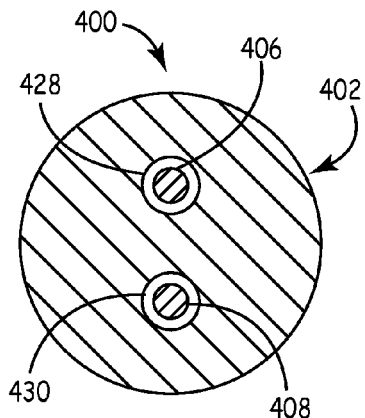
FIG. 13B is a cross section of a catheter assembly of FIG. 13A along the line B-B.

With additional reference to FIG. 13B, the catheter body 402 preferably defines a first lumen 428 and a second lumen 430. The first lumen 428 extends from the proximal portion 416 through the distal portion 420, including the ablation section 422, and is preferably closed or terminates at a distal end 432 of the catheter body 402. As described in greater detail below, the first lumen 428 is sized to slidably receive the shaping wire 406 as depicted in FIG. 13B, and preferably has a diameter slightly greater than that of the shaping wire 406 and any other elements carried by the shaping wire 406, such as a coil electrode. With this configuration, the first lumen 428 provides sufficient spacing about the shaping wire 406 to allow passage of the conductive liquid or ionic fluid (not shown) from the fluid source 404. Thus, the first lumen 428 is fluidly connected to the fluid source 404 and directs liquid from the fluid source 404 to at least the ablation section 422. By closing the first lumen 428 at the distal end 432, a back pressure can be generated within the first lumen 428 to promote fluid irrigation through the ablation section 422 as described below.

Figure 13C:
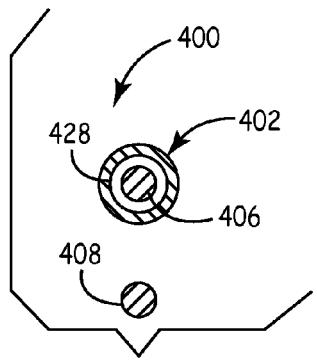
FIG. 13C is a cross-sectional view of the catheter assembly of FIG. 13A along the line C-C.

The second lumen 430 extends from the proximal portion 416 to the distal portion 420, preferably terminating at an opening 434 located proximal the ablation section 422. This relationship is illustrated in FIG. 13C. The second lumen 430 is sized to slidably maintain the guide wire 408. In this regard, the catheter body 402 is preferably configured such that in the deployed position of FIG. 13A, the guide wire 408 extends from the opening 434 in a substantially concentric fashion relative to the helix formed in or by the distal portion 420.

Figure 14A:
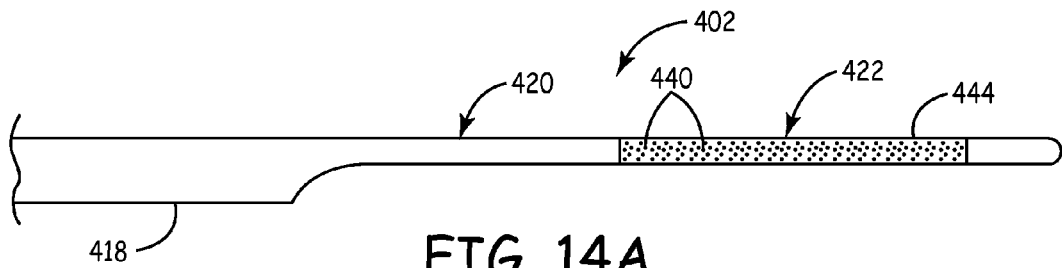
FIG. 14A is a side view of a catheter body of the catheter assembly of FIG. 13A in uncoiled position.

The catheter body 402 is described in greater detail with reference to FIG. 14A. For ease of illustration, only a portion of the catheter body 402 is provided in FIG. 14A, including the intermediate portion 418 and the distal portion 420. Further, the distal portion 420 is shown in a straightened or uncoiled state, as compared to the helical configuration of FIG. 13A. As previously described, the catheter body 402 includes the ablation section 422 formed along the distal portion 420. In one preferred embodiment, the ablation section 422 is formed of a material different from a remainder of the catheter body 402, including the distal portion 420. More particularly, the ablation section 422 is tubular, formed of a flexible, microporous, surgically-safe material, whereas a remainder of the catheter body 402, and in particular the distal portion 420, is formed of a flexible, fluid impermeable material. In one preferred embodiment, the ablation section 422 is a microporous polymer, preferably microporous, high density, expanded polytetrafluoroethylene (PTFE), whereas a remainder of the distal portion 420 is a fluid impermeable polymer, such as polyethylene, polyurethane or PEBAX™ material (polyurethane and nylon). A remainder of the catheter body 402 is similarly formed from a fluid impermeable, polymeric, electrically non-conductive material but can be more rigid than the distal portion 420. Alternatively, other known materials useful in catheter applications are equally acceptable.

Figure 13D:
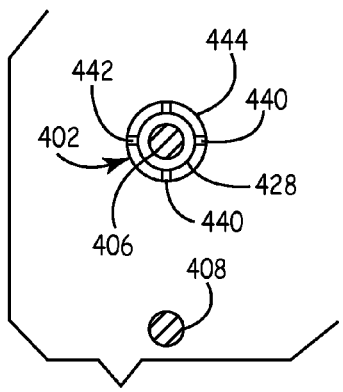
FIG. 13D is a cross-sectional view of the catheter assembly of FIG. 13A along the line D-D.
Figure 13E:
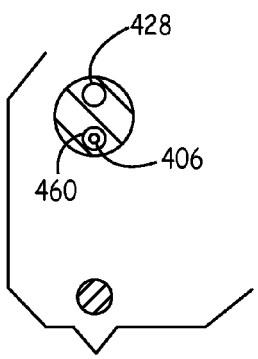
FIG. 13E is a cross-sectional view of an alternative embodiment catheter assembly.

Use of a porous material for the ablation section 422 establishes a plurality of pores 440 extending from an interior surface 442 to an exterior surface 444. As shown in FIG. 13D, the pores 440 are in fluid communication with the first lumen 428. It should be noted that a size of the pores 440 has been greatly exaggerated in FIG. 13D for purposes of illustration. Further, the pores 440 need not be continuous from the exterior surface 444 to the interior surface 442. Instead, a plurality of interconnected interstitial spaces can be formed by the ablation section 422 so as to establish fluid communication between the interior surface 442 and the exterior surface 444. As a point of reference, a porosity of the ablation section 422 is preferably in the range of approximately 5-25 microns. Regardless of the exact construction, the ablation section 422 formed with microporous material irrigates liquid (and contained ions) from the first lumen 428 to the exterior surface 444 in a uniform fashion along an entirety of the exterior surface 444, or at least along an entire length of the ablation section 422 (and thus into contact with targeted tissue (not shown)). With this construction, then, where the conductive fluid has been energized (such as by an electrode), a continuous electrode is effectively established along an entire length of the ablation section 422, in direct contrast to "compartmentalized" ablation electrodes typically employed. By way of example, use of a high density, expanded PTFE material for the ablation section 422 having a straightened length of approximately 3.2 inches (81.3 mm) and wall thickness of approximately 0.010 inch (0.25 mm) exhibited virtually uniform liquid distribution of a preferably isotonic, alternatively hypertonic, saline solution along the exterior surface 444 at flow rates as low as 1 ml/min.

Figure 14B:
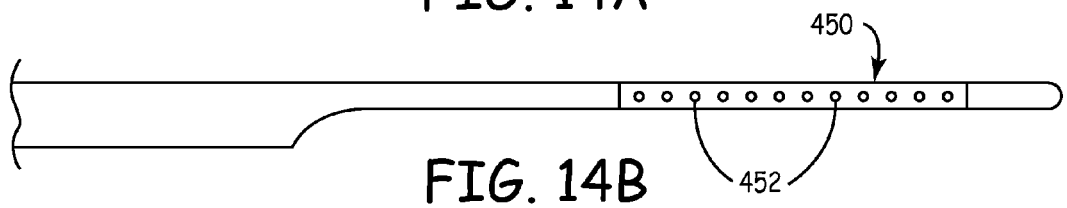
FIG. 14B is a side view of an alternative catheter body portion of the catheter assembly of FIG. 13A.

While the ablation section 422 has been preferably described as being formed of a microporous polymer, other constructions are equally acceptable. For example, as shown in FIG. 14B, an alternative ablation section 450 is initially formed as a non-porous sleeve. During manufacture, a series of small passages 452 are created in the sleeve, such as with a laser, to facilitate generally uniform irrigation of a conductive liquid for an interior to an exterior of the sleeve. Once again, the passages 452 are minute, preferably having a diameter in the range of 5-100 microns. A wide variety of materials are useful for the sleeve, including polyethylene (high or low density), nylon, polyamide block co-polymer, PTFE, polyurethane, fluoropolymers, etc.

Regardless of exact construction, in a preferred embodiment the distal portion 420, including the ablation section 422, is preferably compliant, and can readily be manipulated to a desired shape. To this end, the shaping wire 406 is preferably employed to selectively direct the distal portion 420 to the helical or coiled configuration of FIG. 13A. Thus, in one preferred embodiment, the distal portion 420, including the ablation section 422, defines the first lumen 428 for receiving the shaping wire 406 along with an electrode (not shown) for applying an ablation energy to fluid irrigated through the ablation section 422. This relationship is depicted in FIG. 13D. Alternatively, and with reference to FIG. 13E, an additional lumen, such as a third lumen 460, can be formed in the distal portion 420 (and extending to the proximal portion 418). With this configuration, the first lumen 428 is available to direct fluid to the ablation section 422, while the third lumen 460 is available to maintain the shaping wire 406 and/or an electrode for applying an ablation energy. Even further, the material selected for the distal portion 420 can have an elasticity or shape memory characteristic such that the helix configuration is independently achieved by the distal portion 420 without requiring the separate shaping wire 406.

Returning to FIG. 14A, regardless of the exact construction, the ablation section 422 is preferably sized so as to provide a relatively large ablation area when formed as a loop (as otherwise depicted in FIG. 13A). In one preferred embodiment, the ablation section 422 has a straightened length in the range of approximately 2-8 inches (51-203 mm), more preferably approximately 5 inches (127 mm). Alternatively, other dimensions are equally acceptable.

Figure 15A:
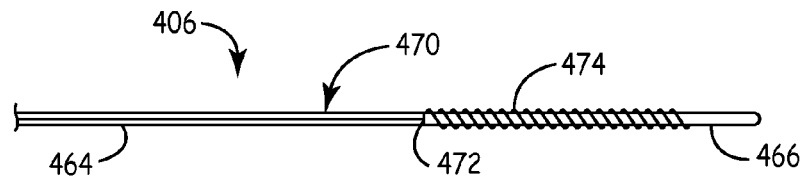
FIG. 15A is a side view of a shaping wire of the catheter assembly of FIG. 13A in a straightened position.
Figure 15B:
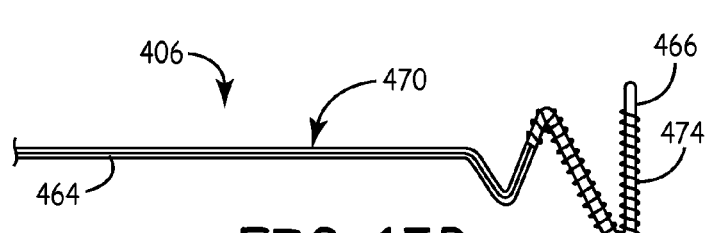
FIG. 15B is a side view of the shaping wire of FIG. 15A in a helical position.

The shaping wire 406 is shown in greater detail in FIGS. 15A and 15B. The shaping wire 406 includes a proximal segment (not shown), an intermediate segment 464 and a distal segment 466. In addition, a metal wire 470 is preferably provided and secured to the shaping wire 406 as described below. As a point of reference, the distal segment 466 is shown in a straightened or uncoiled state in FIG. 15A, whereas FIG. 15B depicts a helical (or coiled) state.

The shaping wire 406, and in particular the distal segment 466, is preferably formed of a thin material having a super elasticity or shape memory characteristic. For example, in one preferred embodiment, the shaping wire 406 is formed from spring-like material such as super elastic or pseudo-elastic nickel titanium (commercially available as Nitinol material), having a diameter in the range of approximately 0.010-0.020 inch (0.25-0.5 mm) With this or other resilient material (such as stainless steel or resilient plastic), the desired helical configuration of the distal segment 466 is imparted during formation of the shaping wire 406. As a result, the distal segment 466 has a highly resilient, spring-like attribute whereby the distal segment 466 can be "forced" to the straightened state of FIG. 15A, but will readily revert to the helical configuration of FIG. 15B (it being understood that the super elastic Nitinol or other material has a phase transition temperature well below normal human body temperature).

The metal wire 470 is wound about a portion of the distal segment 466 to form a coil electrode 474 and is secured to the shaping wire 406, such as by a weld 472. Further, the metal wire 470 extends to the proximal segment (not shown) where it is electrically connected to a power source (not shown), for example a source of radio frequency (RF) energy. The location and length of the coil electrode 474 relative to the shaping wire 406 corresponds with a location and length of the ablation section 422 (FIG. 14A) relative to the catheter body 402 (FIG. 14A). Thus, upon final assembly and activation of the power source, the coil electrode 474 serves to provide an ablation energy to the ablation section 422, and in particular, the conductive fluid (not shown) otherwise supplied to the ablation section 422. Notably, a winding density and thickness of the coil electrode 474 does not impede the ability of the distal segment 466 to revert to the helical state of FIG. 15B. In the straightened state of FIG. 15A, the coil electrode 474 preferably has a length slightly greater than a length of the ablation section 422, in the range of approximately 2.5-8.5 inches (63-216 mm) In one preferred embodiment, with the ablation section 422 length of approximately 5 inches (127 mm), the coil electrode 474 has a length of approximately 5.5 inches (140 mm). A wide variety of known, electrically conductive materials are available for use as the metal wire 470. Preferably, however, the metal wire 470 is comprised of platinum, copper, copper-silver alloy, nickel-cobalt alloy, etc.

Figure 15C:
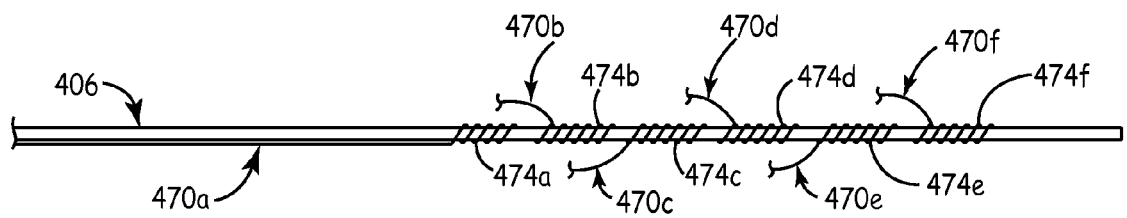
FIG. 15C is a side view of an alternative shaping wire in a straightened position.

While the shaping wire 406 has been described as carrying a single metal wire 470, and thus a single coil electrode 474, multiple wires/coil electrodes can be provided. For example, in a more preferred embodiment, depicted in FIG. 15C, six metal wires 470a-470f forming six coil electrodes 474a-474f are each secured to the distal segment 466 (depicted in a straightened state for ease of illustration) as previously described. The coil electrodes 474a-474f are preferably longitudinally spaced by approximately 1-2 mm. For ease of illustration, only one of the metal wires 470a is shown as extending proximally, it being understood that all of the metal wires 470a-470f extend proximally, and are connected to a power source and/or control box (not shown). The coil electrodes 474a-474f are sized such that when the shaping wire 406 assumes the helical shape, (e.g., FIG. 15B) each of the coil electrodes 474a-474f have a length less a full revolution defined by the distal segment 466. While the coil electrodes 474a-474f may have varying lengths, the coil electrodes 474a-474f are sized such that a combined length is slightly greater than one revolution (or of a length of the ablation section 422 (FIG. 13A)). With this configuration, a user can selectively ablate quadrants or portions of a complete circle (or other closed shape) by selectively energizing less than all of the coil electrodes 474a-474f. For example, a user may wish to ablate only muscle tissue (determined by electrogram analysis). By providing multiple, relatively short coil electrodes 474a-474f, this desired procedure is available. Once again, however, only a single coil electrode is necessary.

Returning to FIG. 13A, the guide wire 408 is of a type known in the art, and is preferably constructed of a rigid metal material. In this regard, the guide wire 408 includes a proximal section 480 and a distal section 482. Further, the guide wire 408 is sized to be slidably received within the second lumen 430 of the catheter body 402. With this relationship, the guide wire 408 is selectively moveable from a retracted position in which the distal section 482 is proximal the distal portion 420, and a deployed position in which the distal section 482 is distal the distal portion 420 (as shown in FIG. 13A). Finally, the distal section 482 can be formed to include a J-shaped or floppy tip to facilitate placement within a vein. As described below with reference to an alternative embodiment, the guide wire 408 is not a necessary element, and can be replaced with an alternative locating device.

Finally, the sensing electrode pairs 410a, 410b are preferably band electrodes capable of providing feed back information indicative of electrical activity. As described below, the sensing electrode pairs 410a, 410b are useful for evaluating the "completeness" of an ablation pattern formed by the catheter assembly 400. To this end, the sensing electrode pairs 410a, 410b are strategically located along the distal portion 420 relative to the ablation section 422. It will be noted that the distal portion 420 is preferably helically-shaped, having a decreased diameter proximal the ablation section 422, and an increased diameter distal the ablation section 422. With this in mind, the first sensing electrode pair 410a is preferably located proximal the ablation section 422 for evaluating electrical activity "within" the loop pattern defined by the ablation section 422. Conversely, the second sensing electrode pair 410b is distal the ablation section 422 for evaluating electrical activity "outside" the loop. With alternative embodiments, one or both of the sensing electrode pairs 410a, 410b can be eliminated; or additional sensing electrodes provided. Even further, additional sensors, such as a thermocouple, can be included along the distal portion 420.

Figure 16A:
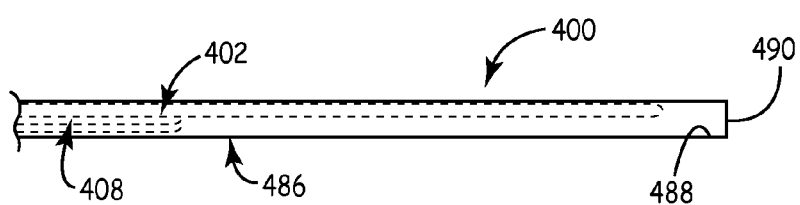
FIGS. 16A and 16B are side views of an alternative catheter assembly in accordance with the present invention.
Figure 16B:
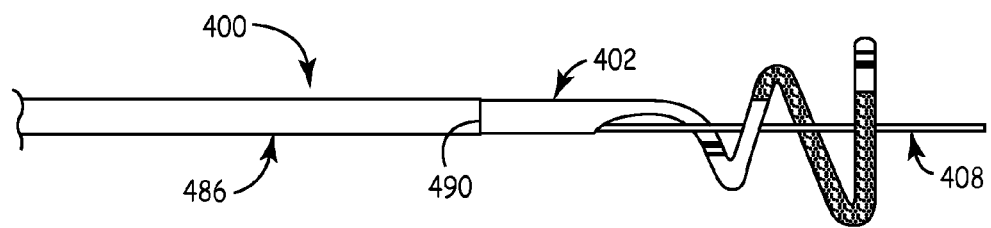

The catheter assembly 400 of FIG. 13A is deployed to a desired area of a heart as described below, preferably in a straightened or uncoiled state. To facilitate this arrangement, and in a more preferred embodiment, the catheter assembly 400 further includes a guide catheter or sheath 486 as shown in FIGS. 16A and 16B. For ease of illustration, only a distal region of the catheter assembly 400 is shown in FIGS. 16A and 16B. The guide catheter 486 forms a lumen 488 sized to slidably maintain the catheter body 402 (including the shaping wire 406 and the guide wire 408), and terminates at an open tip 490. With this configuration, the catheter assembly 400 is selectively maneuverable between the retracted position of FIG. 16A in which entireties of the catheter body 402, the shaping wire 406, and the guide wire 408 are proximal the tip 490, and the deployed position of FIG. 16B in which portions of the various components 402, 406, 408 are distal the tip 490. As described in greater detail below, then, the catheter assembly 400 is initially directed to a desired area in the retracted position. Subsequently, the catheter body 402, the shaping wire 406 and the guide wire 408 are directed to the deployed position of FIG. 16B.

FIG. 17A-17D illustrate use of the catheter assembly 400 within the heart 50, and in particular the left atrium (LA). Prior to deployment of the catheter assembly 400, the left atrium LA anatomy is preferably evaluated using an available 3-D imaging device, such as a fluoroscope, CT scanner, MRI or ultrasound, to determine the geometry and orientation of the various pulmonary veins (PV). The fluid source 404 (FIG. 13A) is activated to provide a continuous flow of conductive liquid, (e.g., isotonic saline solution) to the first lumen 428 (FIG. 13A), and in particular the ablation section 422 (FIG. 13A). For example, a continuous flow rate in the range of 1-4 ml/min is established to purge air from the first lumen 428.

Figure 17A:
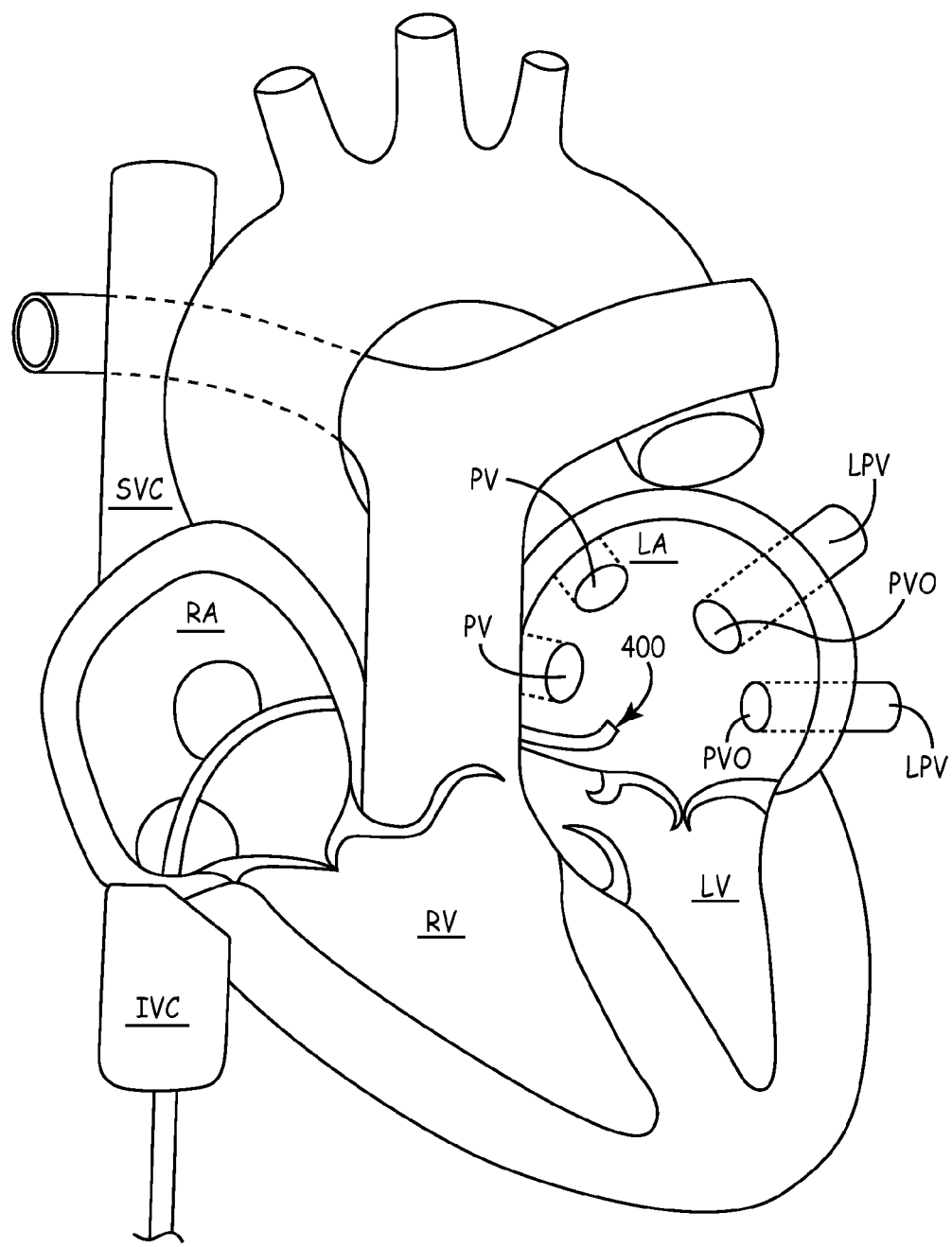
FIGS. 17A-17D illustrate use of the catheter assembly of FIG. 13A within a heart.
Figure 17B:
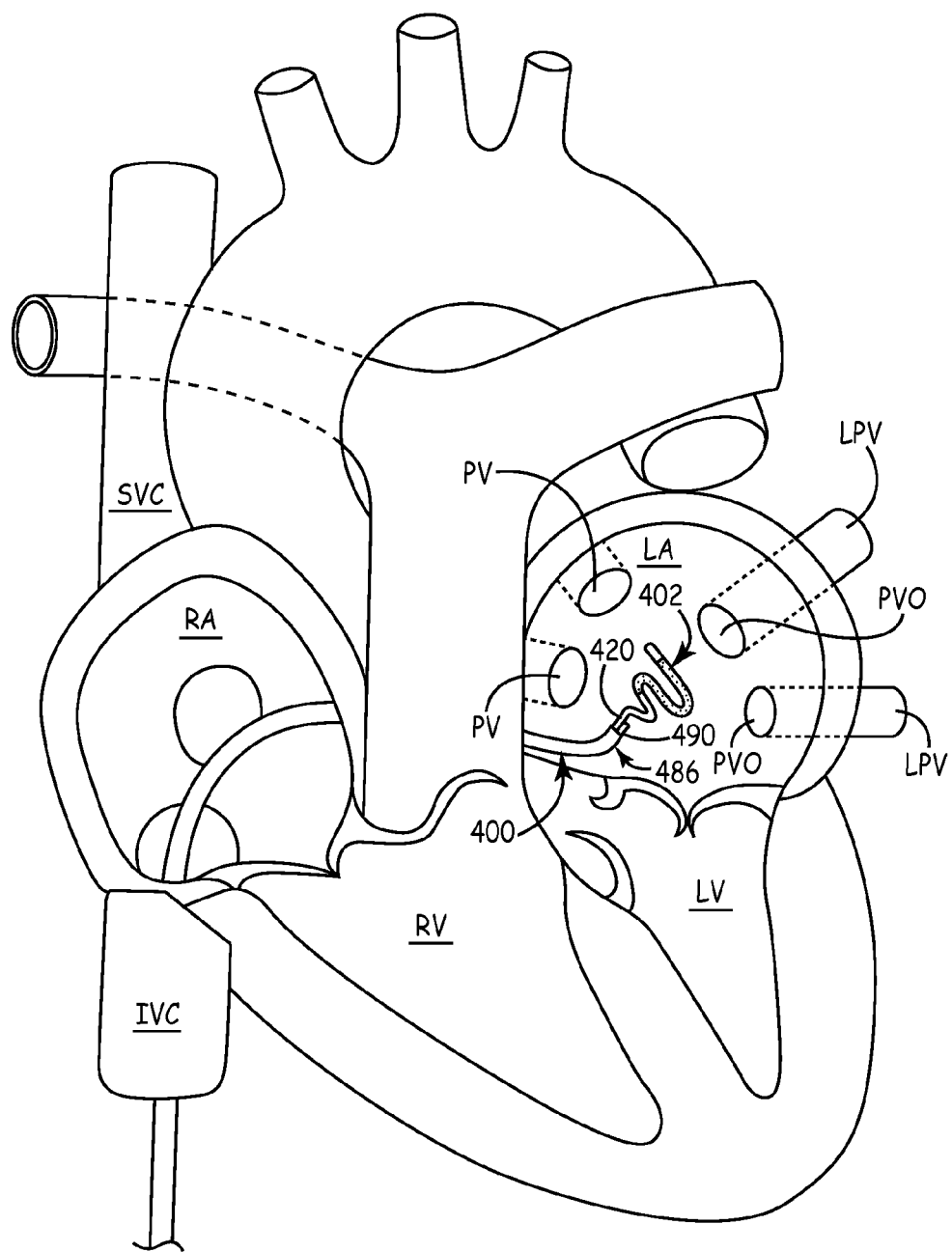

Following the preparatory steps, and with reference to FIG. 17A, electrical isolation of a left pulmonary vein (LPV) begins by directing the catheter assembly 400 of FIG. 16A in a retracted position through the inferior vena cava (IVC), into the right atrium (RA) through a puncture in the interatrial septum (not shown) and into the left atrium LA. Alternatively, the introduction of the catheter assembly 400 into the right atrium RA is also suggested by passage of the catheter body 402 into the right atrium RA through the superior vena cava (SVC). The tip 490 of the guide catheter 486 is positioned slightly spaced from the pulmonary vein ostium PVO associated with the left pulmonary vein (LPV) to be isolated. The catheter body 402 is then deployed as shown in FIG. 17B. More particularly, the distal portion 420 is extended distal the tip 490 of the guide catheter 486. In this regard, the distal segment 466 (FIG. 13A) of the shaping wire 406 (FIG. 13A) is within the distal portion 420 of the catheter body 402 such that the distal portion 420 forms the helical shape shown in FIG. 17B.

Figure 17C:
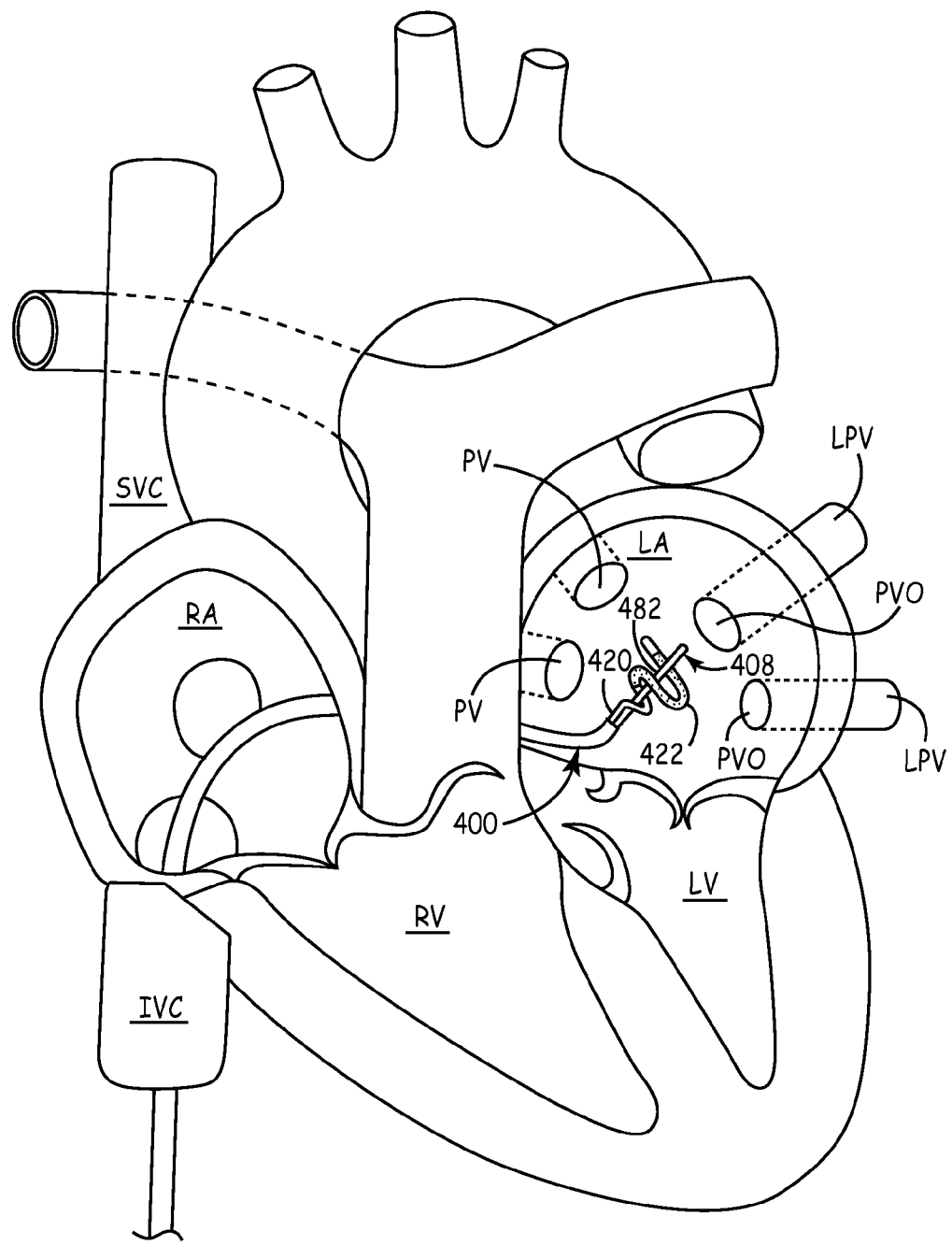

Following deployment of the catheter body 402, the guide wire 408 is then deployed as illustrated in FIG. 17C. By preferably performing deployment of the catheter assembly 400 in this order, the opportunity for damage to the catheter body 402 is minimized Once deployed, the distal section 482 of the guide wire 408 is substantially concentric with, and extends distally beyond, the helix formed at the distal portion 420.

Once deployed, the guide wire 408 is utilized to locate the left pulmonary vein LPV to be treated. In this regard, a fluoroscope is preferably employed to provide visual confirmation that the guide wire 408 is positioned within the left pulmonary vein LPV to be isolated.

Figure 17D:
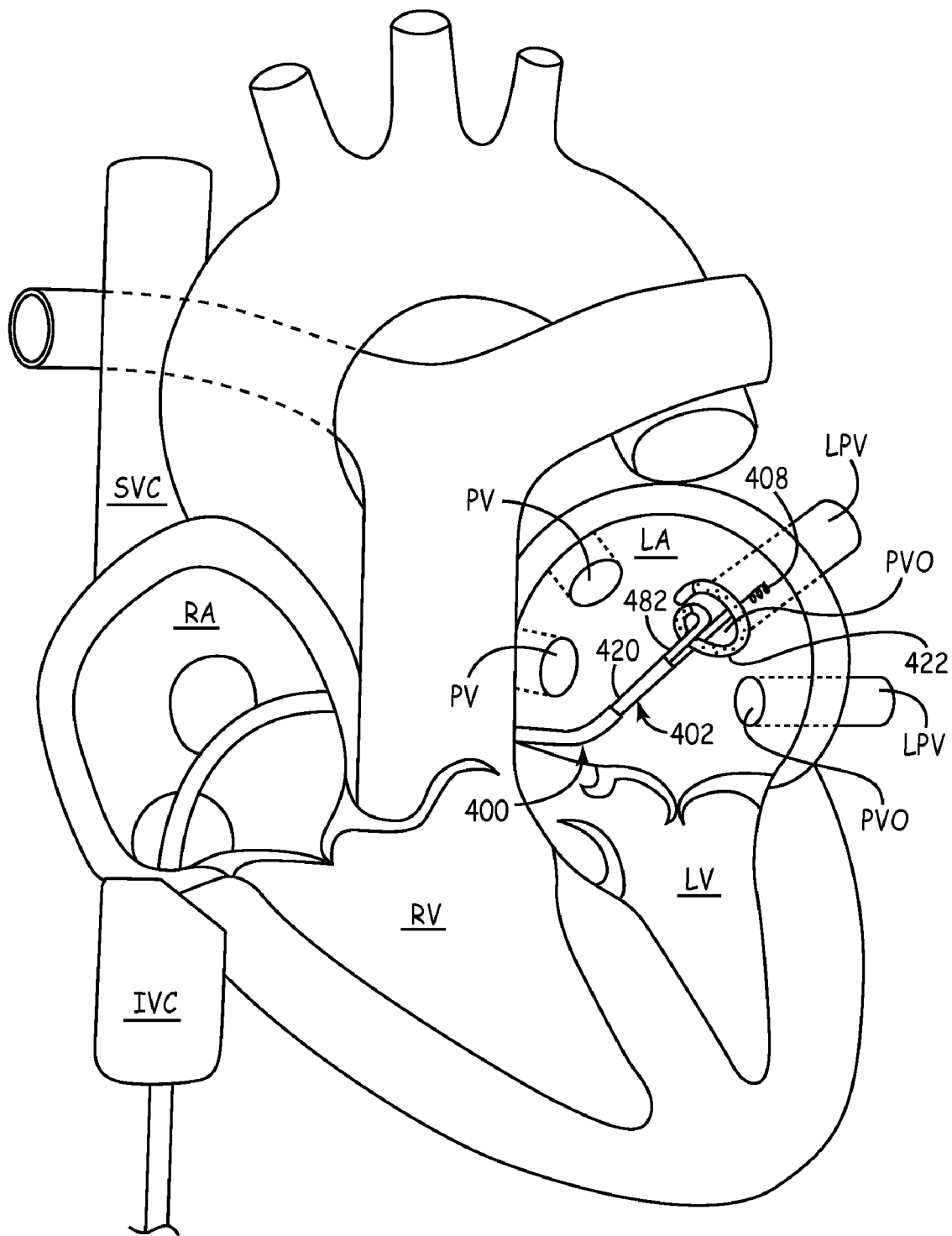

The catheter body 402 is advanced over the guide wire 408 and into contact with the left atrium LA tissue wall/material surrounding the pulmonary vein ostium PVO as shown in FIG. 17D. In particular, the distal portion 420 is pressed against the tissue wall such that the helix formed in or by the distal portion 420 compresses onto itself and the loop formed by the ablation section 422 is in complete contact with the chamber wall about the pulmonary vein ostium PVO. To this end, fluoroscopic visualization is preferably utilized to confirm relatively continuous contact between the ablation section 422 and the chamber wall. In addition, bipolar electrograms can be recorded from the electrode pairs 410*a*, 410*b* to assess LA endocardial wall contact.

The fluid flow rate from the fluid source (not shown) to the ablation section 422 is then increased to approximately 4-10 ml/min. After waiting for a short period to ensure increased fluid flow to, and irrigation through, the ablation section 422, the coil electrode 472 (FIG. 16A) is energized, for example with RF energy. This energy is transferred via the fluid irrigated along the ablation section 422 to the tissue contacted by the ablation section 422. The conductive fluid establishes a conductive path from the coil electrode 472 to the contacted tissue, thereby ablating the targeted tissue. As previously described, a porosity associated with the ablation section 422 is such that the conductive fluid irrigates or "weeps" or "sweats" to the exterior surface 444 (FIG. 13D) of the ablation section 422. This weeping attribute serves to cool the coil electrode 472 and, because the fluid contacts the targeted tissue, minimizes the opportunity for thrombosis formation. In one preferred embodiment, the coil electrode 472 is energized for two minutes at 40-50 watts, although other ablation energies and times are equally acceptable. The endpoint of energy delivery can be determined by the reduction in electrogram amplitude at the discretion of the physician.

Figure 18A:
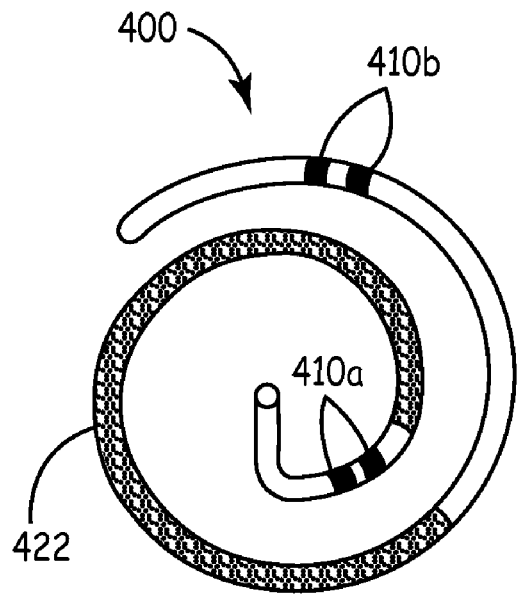
FIG. 18A is an end view of the catheter assembly of FIG. 13A in an axially compressed position.
Figure 18B:
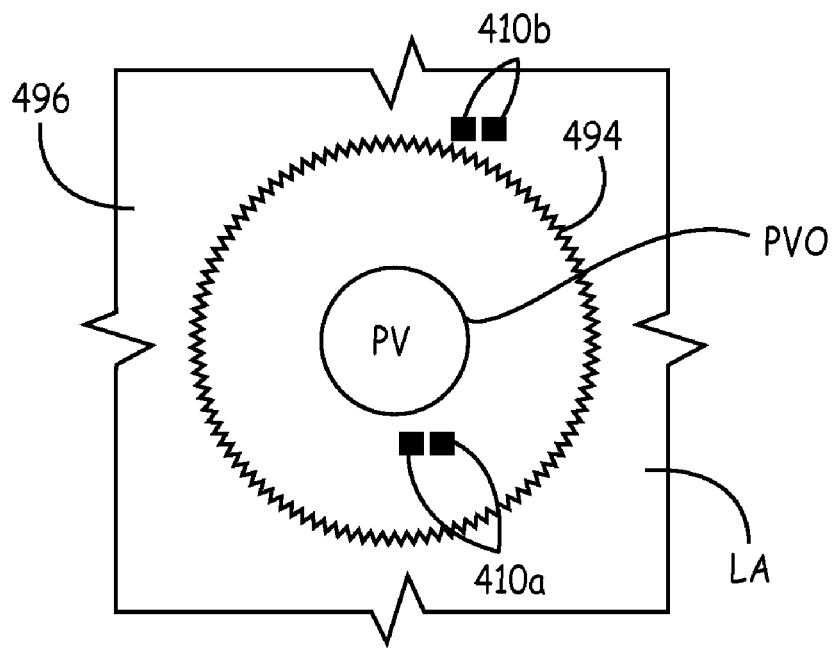
FIG. 18B is a simplified view of an ablation pattern formed with the catheter assembly of FIG. 13A.

Following application of the ablation energy, the catheter assembly 400 is preferably operated to determine whether a closed, electrically isolating ablation pattern has been established in the chamber wall, about or outside of the ostium PVO. More particularly, and as shown in FIGS. 18A and 18B, the sensing electrode pairs 410*a*, 410*b* are simultaneously interrogated to evaluated isolation of the PV ostium PVO from the left atrium LA wall. As a point of reference, FIG. 18A provides an end view of the distal portion 420 compressed against a chamber wall (not shown), including the ablation section 422 and the sensing electrode pairs 410*a*, 410*b*. Conversely, FIG. 18B depicts an ablation pattern 494 formed on a tissue wall 496, as well as locations of the sensing electrode pairs 410*a*, 410*b* relative to the ablation pattern 494 when the distal portion 420 (not shown in FIG. 18B) is compressed against the tissue wall 496. With these orientations in mind, the first sensing electrode pair 410*a* is located within the ablation pattern 494, whereas the second sensing electrode pair 410*b* is located outside of the ablation pattern 494. This configuration is further exemplified by reference to FIG. 18A in which the first sensing electrode pair 410*a* is located within loop defined by the ablation section 422, whereas the second sensing electrode pair 410*b* is outside of the loop. Following application of the ablation energy, the sensing electrode pairs 410*a*, 410*b* are operated to observe and sense electrical activity inside and outside of the ablation pattern 494. If it is determined that electrical activity continues to traverse the ablation pattern 494, an ablation energy can again be applied to the coil electrode 472 (FIG. 13A) to further ablate the tissue wall about the pulmonary vein ostium PVO. Once sufficient ablation has been achieved, the catheter body 402 and the guide wire 408 are retracted from the pulmonary vein ostium PVO. Subsequently, additional ablation patterns can be formed about other ones or all of the pulmonary vein ostia PVOs.

Figure 19:
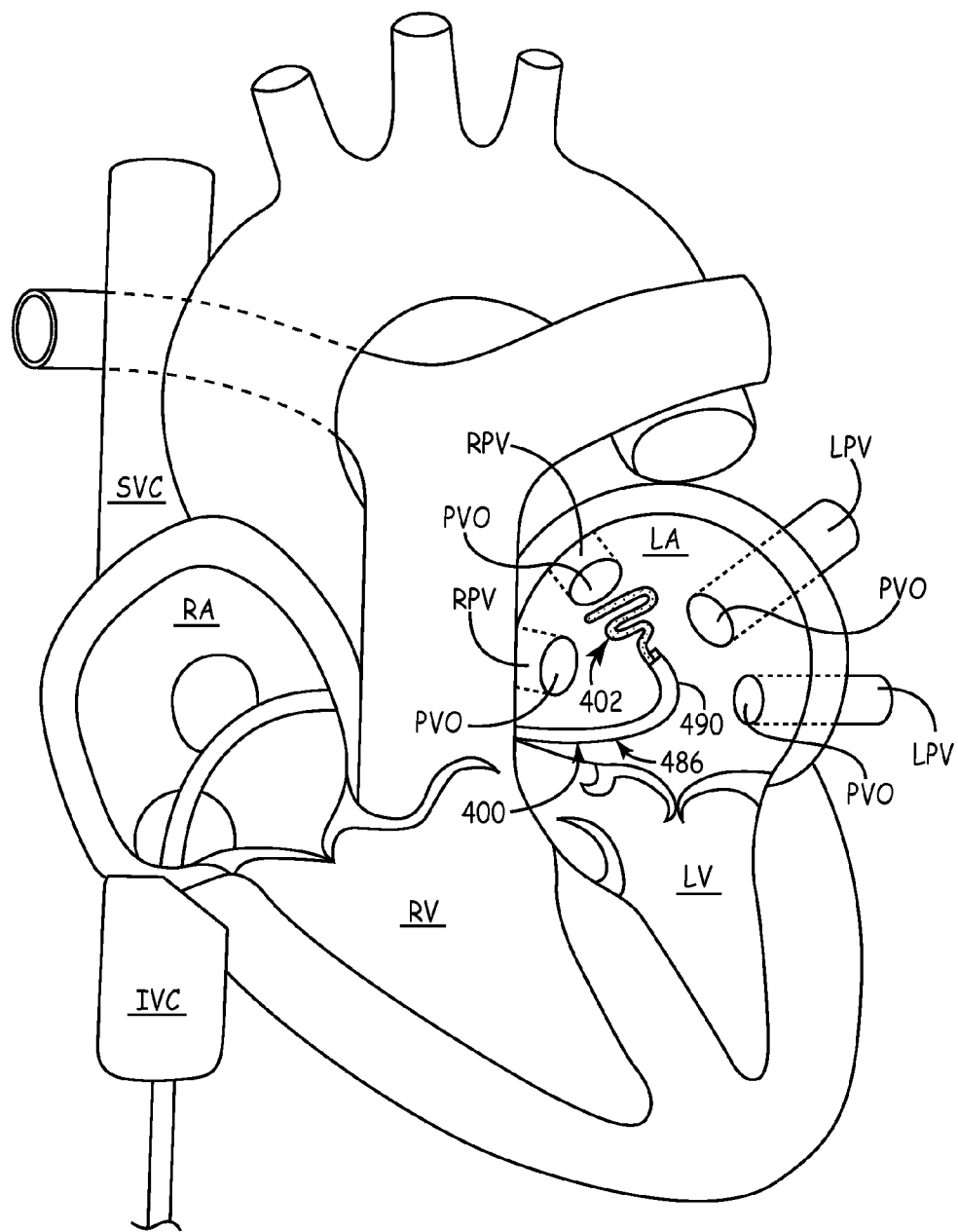
FIG. 19 illustrates use of an alternative catheter assembly within a heart.

As should be evident from the views of FIG. 17A-17D, proper positioning of the catheter assembly 400 relative to the left pulmonary veins LPVs is straightforward in that the catheter assembly 400 is essentially axially aligned with the left pulmonary veins LPVs upon passage into the left atrium LA. However, the right pulmonary veins RPVs are normally obliquely orientated relative to the catheter assembly 400 upon guidance into the left atrium LA. Thus, in one preferred embodiment, and as shown in FIG. 19, the catheter assembly 400 is preferably provided with a steering capability so that the right pulmonary veins RPVs are more easily accessed. For example, the guide catheter 486 can be configured such that the tip 490 is deflectable relative to remainder of the guide catheter 486, and therefore maneuverable by a user to the position shown in FIG. 19. Controls and structures useful in providing this steering capability are well-known in the art, and can include a stiffening wire or pulling wire extending along the guide catheter 486. Alternatively and/or in addition, the catheter body 402 may be provided with a steering device to facilitate selective deflection of the distal portion 420 relative to a remainder of the catheter body 402.

The preferred implementation of the shaping wire 406 (FIG. 16A) to dictate the axially compressible, helical shape of the distal portion 420 of the catheter body 402 provides several advantages. First, because the distal portion 420, and in particular the ablation section 422, need not have a rigid characteristic necessary to maintain the helical shape, a compliant, microporous material can be used for the ablation section 422, such as high density, expanded PTFE. The microporous material facilitates uniform perfusion of conductive fluid that cools the ablation section 422, thereby minimizing the opportunity for thrombus formation. In addition, a wide variety of differently shaped and sized shaping wires 406 can be made available to a user, who can then select the size and shape most appropriate for achieving desired ablation. In other words, upon evaluating the pulmonary vein and associated ostium, the user can select an appropriate shaping wire that in turn dictates an optimal size and shape of the distal portion 420 and the ablation section 422. In this regard, not only can an overall size of the ostium (e.g., larger or smaller) be properly accounted for, but also the associated shape. For example, as shown in FIG. 20A, a simplified, side-sectional view of a pulmonary vein PV is shown, including the chamber wall tissue T surrounding and forming the pulmonary vein ostium PVO. As is evident from the illustration, the chamber wall tissue T is relatively planar adjacent the pulmonary vein ostium PVO. As such, the selected shaping wire 500 of FIG. 20B includes a coil segment 502 that axially compresses to a relatively planar loop or series of loops. During use, then, and as shown in FIG. 20C, the relatively planar, axially compressed configuration of the shaping wire 500 readily conforms with the relatively planar configuration of the chamber wall tissue T, so that an optimal ablation pattern is formed on the chamber wall tissue T outside of the pulmonary vein ostium PVO.

Alternatively, as shown in FIG. 21A, the pulmonary vein ostium PVO and associated chamber wall tissue T can have a non-planar shape. More particularly, pulmonary vein ostia are often formed to have a "saddle" shape. When so identified, a user will select a correspondingly-shaped shaping wire, such as the shaping wire 504 depicted in FIG. 21B. The shaping wire 504 includes a coiled segment 506 that, when axially compressed, assumes a non-planar shape. During use, and when axially compressed against the chamber wall tissue T, the coiled segment 506 assumes a "saddle" shape corresponding generally with the chamber wall tissue outside of (or surrounding) the pulmonary vein ostium PVO, as depicted in FIG. 21C. In practice, by providing a number of interchangeable, but uniquely sized and shaped shaping wires, a user can quickly ablate and electrically isolate all of the pulmonary vein ostia PVOs without removing the catheter body 402 from the left atrium LA.

Figure 22:
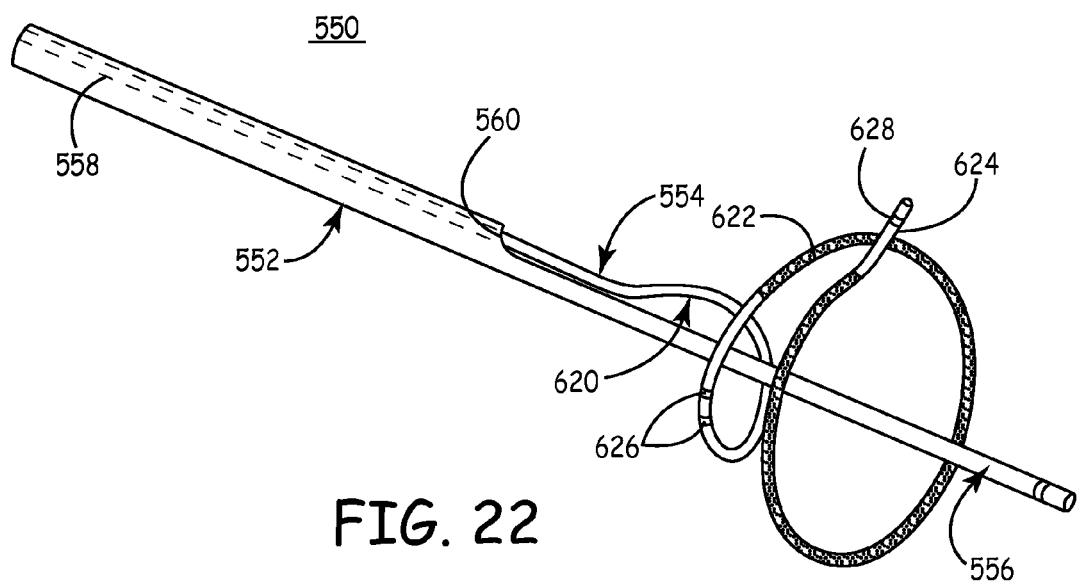
FIG. 22 is a simplified, perspective view of an alternative embodiment catheter assembly in accordance with the present invention.

Another alternative, more preferred embodiment of a catheter assembly 550 is shown in FIG. 22. For ease of illustration, only a distal region of the catheter assembly 550 is depicted. The catheter assembly 550 is similar to the catheter assembly 400 (FIGS. 13A-13E) previously described, and includes a delivery catheter 552 and an ablation catheter 554. The delivery catheter 552 includes a distal locator 556 and forms a delivery lumen 558 (shown partially in FIG. 22) terminating at an opening 560 proximal the delivery locator 556. The ablation catheter 552 is slidably disposed within the delivery lumen 558 such that the ablation catheter 552 is selectively deployable and retractable relative to the delivery catheter 552 via the opening 560.

The delivery catheter 552 is shown in greater detail in FIG. 23. For ease of illustration, the ablation catheter 554 (FIG. 22) has been omitted from the view of FIG. 23. The delivery catheter 552 includes a proximal region 570, an intermediate region 572, and the distal locator 556. The intermediate region 572 extends from the proximal region 570 and terminates in the opening 560. The distal locator 556, in turn, extends from the intermediate region 572 distal the opening 560. As described in greater detail below, the delivery catheter 552 is preferably steerable both proximal and distal the opening 560.

In light of the preferred steerable attribute of the delivery catheter 552, the proximal region 570 includes a Y-connector 574 coupled to a handpiece 576 and a guide piece 578. The handpiece 576 is of a type known in the art and provides control devices 580, the operation of which effectuates desired bending of the delivery catheter 552 via pull wires (not shown) described in greater detail below. The guide piece 578 is fluidly connected to the delivery lumen 558 (FIG. 22) and preferably is a hemostatic valve forming a first port 582 and a second port 584. The first port 582 is available for receiving and directing a separate body, such as the ablation catheter 554 (FIG. 22) or a dilator (not shown), to the delivery lumen 558. Further, the second port 584 is also fluidly connected to the delivery lumen 558, and is available for directing fluid thereto. For example, the second port 584 can be fluidly connected to a stop cock valve (not shown) that in turn facilitates flushing of a liquid, such as saline, through the delivery lumen 558 while preventing back flow of other liquids, such as blood.

Figure 24D:
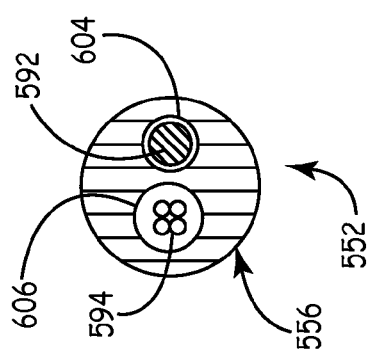
FIG. 24D is a cross-sectional view of the delivery catheter of FIG. 23 along the line 24D-24D.
Figure 24B:
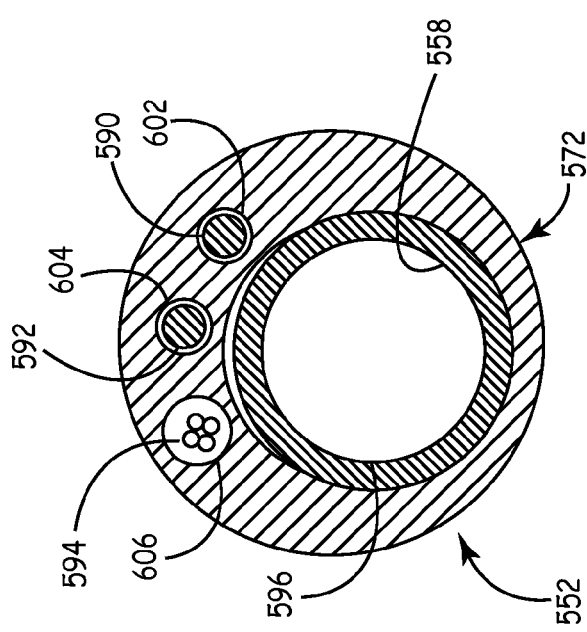
FIG. 24B is a cross-sectional view of the delivery catheter of FIG. 23 along the line 24B-24B.
Figure 24A:
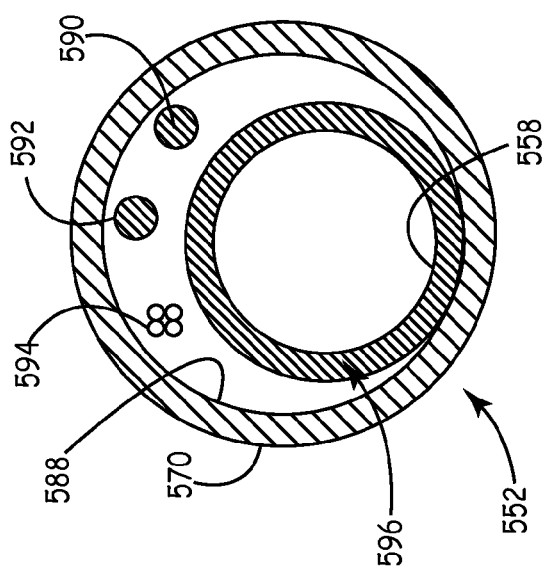
FIG. 24A is a cross-sectional view of the delivery catheter of FIG. 23 along the line 24A-24A.

With further reference to FIG. 24A, the proximal region 570 forms the delivery lumen 558 within which the ablation catheter 554 (FIG. 22) is slidably disposed. In addition, the proximal region 570 forms a passage 588 surrounding the delivery lumen 558 and maintaining, as depicted in FIG. 24A, a first pull wire 590, a second pull wire 592, and a cluster of electrode wires 594. In one preferred embodiment, the delivery lumen 558 is defined by a tube 596 disposed within the passage 588. Alternatively, the proximal region 570 can be configured to integrally form the delivery lumen 558. The first pull wire 590 extends from the handpiece 576 to the intermediate region 572 for effectuating steering or bending of the delivery catheter 552 proximal the opening 560 (FIG. 23). The second pull wire 592 extends from the handpiece 576 to the distal locator 556 for effectuating steering or bending of the delivery catheter 552 distal the opening 560. Finally, the cluster of electrode wires 594 are electrically connected to an auxiliary energy source (not shown) for energizing various electrodes associated with the delivery catheter 552.

The proximal region 570 is preferably formed of a reinforced, braided material such as a tubular shaft constructed of "Ultem," polyamide, or other high temperature polymer covered with a reinforcing braid wire or high strength filament and jacketed by a flexible polymer such as nylon, polyurethane or "PEBAX"™. With this preferred material, the proximal region 570 exhibits enhanced torqueability, such that a user can more easily steer or guide the delivery catheter 552 to a target site.

The intermediate region 572 forms the opening 560 and preferably maintains an electrode 600. With additional reference to FIG. 24B, the intermediate region 572 defines first, second, and third lumens 602-606, in addition to the delivery lumen 558. Once again, the delivery lumen 558 is preferably defined by the tube 596 otherwise carried within the intermediate region 572. Alternatively, the delivery lumen 558 can be integrally formed by the intermediate region 572. The delivery lumen 558 is available to slidably maintain the ablation catheter 554 (FIG. 22) or other body, and terminates at the opening 560. The first pull wire 590 extends through the first lumen 602 and is secured to the intermediate region 572 adjacent the opening 560. The second pull wire 592 extends through the second lumen 604. Finally, the cluster of electrode wires 594 are maintained within the third lumen 606.

The electrode 600 is preferably a band electrode electrically connected to one or more of the cluster of electrode wires 594. With this configuration, the electrode 600 serves as a mapping electrode. Notably, however, the electrode 600 is not a necessary element for use of the delivery catheter 552.

The intermediate region 572 is preferably formed of a material different from that of the proximal region 570. More particularly, unlike the preferably reinforced, torqueable composition of the proximal region 570, the intermediate region 572 is preferably comprised of a softer material such as nylon, polyurethane or "PEBAX"™. With this configuration, the intermediate region 572 is highly amenable to bending via tensioning of the first pull wire 590. To this end, a length of the intermediate region 572 (i.e., longitudinal distance proximal the opening 560) dictates the focal point at which bending of the intermediate region 572 occurs, as well as an available bend radius. In a preferred embodiment, the intermediate region 572 has a longitudinal length in the range of 5-25 cm, more preferably 15 cm.

The opening 560 is shown more clearly in FIG. 24C, and preferably includes rounded or curved edges 608. This preferred configuration minimizes possible tissue damage as the delivery catheter 552 is passed through bodily lumens, for example veins. Alternatively, however, the opening 560 may assume a wide variety of other forms. As described below, a rounded-tip dilator (not shown) is preferably extended into and/or through the opening 560 to further minimize the opportunity for tissue damage during delivery through bodily lumens.

The distal locator 556 extends distally beyond the opening 560 and preferably includes electrode pairs 610a and 610b. Further, the distal locator 556 preferably terminates at a tip 612 that, in one preferred embodiment, incorporates a thermocouple and serves as an electrode pair with an electrode 614. With additional reference to FIG. 24D, the distal locator 556 defines the second lumen 604, maintaining the second pull wire 592, and the third lumen 606, maintaining the cluster of electrode wires 594. The second pull wire 592 is attached to the distal locator 556 adjacent the tip 612. The cluster of electrode wires 594 are connected to the pairs of electrodes 610a and 610b, as well as the tip 612 and the electrode 614. With this configuration, the electrode pairs 610a and 610b, as well as the tip 612 and the electrode 614, are available for mapping and/or ablation functions.

The distal locator 556 is preferably formed from a soft material similar to the intermediate region 572, preferably nylon, polyurethane or "PEBAX"™. With this configuration, the distal locator 556 is bendable or steerable via tensioning of the second pull wire 592. In a preferred embodiment, the distal locator 556 has a length in the range of 5-20 cm, more preferably 15 cm; and a diameter in the range of 5-7 French, more preferably 6 French.

Returning to FIG. 22, the ablation catheter 554 includes a distal portion 620 forming an ablation section 622. In one preferred embodiment, the ablation catheter 554 is highly similar to the catheter body 402 (FIGS. 13A-13C) previously described, such that the ablation section 622 is formed from a microporous material that is fluidly connected to a fluid source (not shown) by a lumen (not shown). Further a shaping wire (not shown) similar to that previously described is slidably disposed within the ablation catheter 554 for selectively forming the distal portion 620, and in particular the ablation section 622, to the helical or loop configuration, and an electrode(s) is associated with the ablation section 622. Alternatively, the ablation catheter 554 can be formed in accordance with any other of the embodiments disclosed herein.

Figure 25:
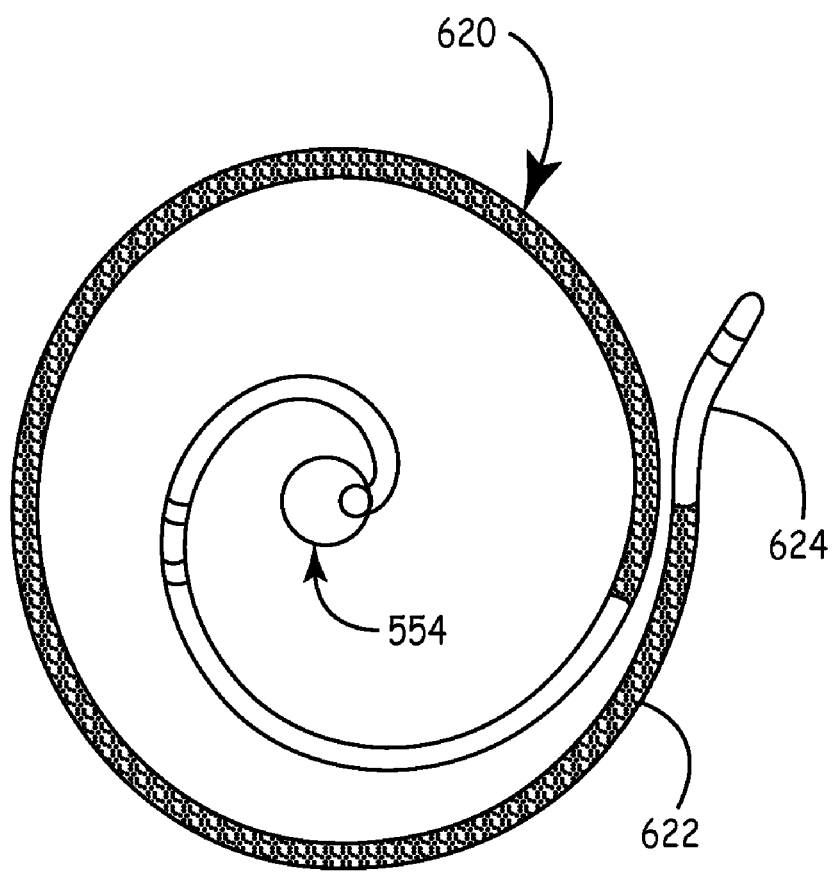
FIG. 25 is an end view of the catheter assembly of FIG. 22.

To facilitate deployment of the ablation catheter 554, a distal end 624 of the distal portion 620 extends radially outwardly relative to a curvature defined by the ablation section 622. This relationship is shown most clearly in FIG. 25. The angle of deflection defined by the distal end 624 relative to the ablation section 622 is preferably in the range of approximately 5-45°, more preferably 10°. As described in greater detail below, as the distal portion 620 is initially deployed relative to the distal locator 556 (FIG. 23) of the delivery catheter 552 (FIG. 23), the offset or deflected orientation of the distal end 624 assists in guiding the distal portion 620 about the distal locator 556.

Returning to FIG. 22, in a preferred embodiment the ablation catheter 554 further includes mapping electrodes 626, 628, proximal and distal the ablation section 622, respectively. As with previous embodiments, the electrodes 626, 628 are available to assist a user in evaluating a target site prior to and following ablation.

The delivery catheter 552 can further include an additional anchoring device (not shown), such as the balloon 136 (FIG. 6) or the wire cage 166 (FIG. 7) previously described.

During use, the delivery catheter 552 is first directed toward the target site (e.g., pulmonary vein ostium). In one preferred embodiment, prior to placement in the patient, the ablation catheter 554 is replaced with a rounded-tip dilator (not shown) known in the art that extends through the delivery lumen 558 and partially out of the opening 560. By providing the dilator, the delivery catheter 552 can be fed through bodily lumens, such as veins, without damaging the tissue walls at the opening 560. Once the intermediate region 572 and the distal locator 556 of the delivery catheter 552 have been guided to the general area of interest (e.g., the left atrium LA), the rounded-tip dilator is removed from the delivery lumen 558, and the ablation catheter 554 inserted therein. The distal portion 620 of the ablation catheter 554 is then deployed through the opening 560. In particular, as the distal portion 620 is directed distally through the opening 560, the ablation catheter 554 is rotated such that the distal end 624 passes around the distal locator 556. The preferred deflected or tangential orientation of the distal end 624 relative to a curvature of a remainder of the distal portion 620 facilitates guiding of the distal end 624 around the distal locator 556. Continued rotation of the ablation catheter 554 positions the distal locator 556 within the circle or spiral defined by the distal portion 620.

With the ablation catheter 554 deployed to the position depicted in FIG. 22, the distal locator 556 is then maneuvered to locate the orifice in question, for example one of the pulmonary vein ostia. In this regard, a user can steer the delivery catheter 552 both proximal and distal the opening 560. For example, the first pull wire 590 (FIG. 25A) can be manipulated or tensioned to bend the delivery catheter 552 at the intermediate region 572 (proximal the opening 560). This first bend serves to "aim" or direct the distal locator 556 generally toward the orifice (or ostium) of interest. As the distal locator 556 is then maneuvered or directed toward the ostium, the distal locator 556 itself can steered via tensioning of the second pull wire 592 (FIG. 24A) so as to facilitate exact, desired positioning of the distal locator 556 within the ostium.

Once the distal locator 556 has been positioned within the ostium in question, the ablation catheter 554 is advanced, with the distal locator 556 effectively "guiding" the distal portion 620, and in particular the ablation section 622, to the target site. In other words, the distal portion 620 "rides" along the distal locator 556 and is thereby properly positioned about the pulmonary vein ostium. Once positioned, the ablation catheter 554 is available to form a continuous ablation pattern on the chamber wall outside of/around the pulmonary vein ostium as previously described. If other of the pulmonary vein ostia require electrical isolation, the distal locator 556 can readily be aligned with the desired ostium by steering or bending of the delivery catheter 552 both proximal and distal the opening 560 as previously described.

Figure 26:
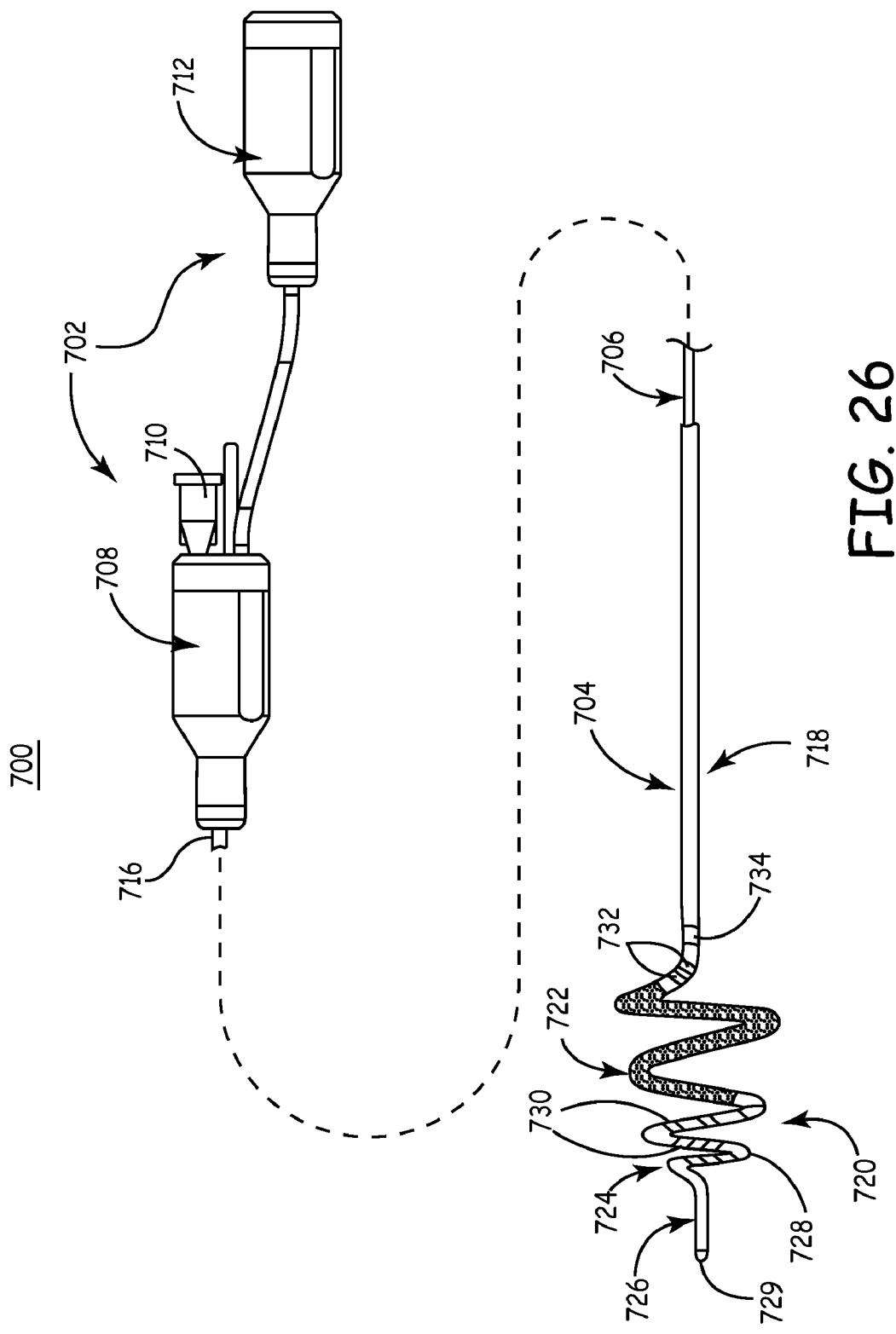
FIG. 26 is a side view of another alternative catheter assembly in accordance with the present invention.

Yet another alternative, even more preferred, embodiment of a catheter assembly 700 is shown in FIG. 26. In a preferred embodiment, the catheter assembly 700 includes input components 702, a catheter body 704, and a shaping wire 706 (shown partially in FIG. 26). In general terms, the input components 702 are connected to the catheter body 704, and control functioning of the catheter assembly 700. As with several previous embodiments, the shaping wire 706 is slidably disposed within a lumen (not shown) of the catheter body 704 to selectively form the catheter body to a desired shape.

The input components can assume a wide variety of forms relating to desired functioning of the catheter assembly 700. For example, in one preferred embodiment, the input components 702 include a hand piece 708, a fluid input port 710 and an ablative energy source 712 (only a portion of which is depicted in FIG. 26). As previously described, the catheter assembly 700 is preferably configured to ablate tissue by energizing fluid irrigated from a portion of the catheter body 704. With this in mind, then, the hand piece 708 provides fluid flow to the catheter body 704 via the fluid input port 710. For example, a saline or other fluid source can be connected to the fluid input port 710. Similarly, the ablative energy source 712 includes an electrical connector (shown in FIG. 26) electrically connecting an energy source (not shown) to corresponding components of the catheter assembly 700 (such as internally disposed coil electrode(s) not otherwise illustrated) via the hand piece 708. In this regard, electrical connectors are well known in the art.

Alternatively, and as described below, where the catheter assembly 700 is designed to make use of a differing ablation energy technique, one or both of the fluid input port 710 and/or the electrical connector 712 can be eliminated, modified or replaced with an appropriate component. For example, the catheter assembly 700 can be configured to ablate tissue via energized band or coil electrodes, ultrasound, RF energy, microwave energy, laser, cryogenic energy, thermal energy, etc., as is known in the art.

The catheter body 704 includes a proximal portion 716, an intermediate portion 718 and a distal portion 720. As with previous embodiments, the intermediate portion 718 extends from the proximal portion 716 and defines a longitudinal axis. The distal portion 720, in turn, extends from the intermediate portion 718, and includes an ablation section 722 and a tip 724. The tip 724 extends distally from the ablation section 722, and, in one preferred embodiment, terminates in a leader section 726.

The shape of the distal portion 720 is an important feature of the catheter body 704. In particular, at least a segment of the distal portion 720 defines a distally decreasing radius helix. In this regard, the ablation section 722 generally forms at least one loop that is preferably transverse to the longitudinal axis defined by the intermediate portion 718. With the one preferred embodiment of FIG. 26, the ablation section 722 forms a plurality of loops that define a distally decreasing radius helix. This configuration has surprisingly been found to greatly enhance positioning and ablation about a pulmonary vein ostium (not shown). The ablation section 722 most preferably defines a plurality of loops curving approximately 540°. Alternatively, any other degree of circumferential extent is acceptable, ranging from 90°-720°. It has surprisingly been found that curving the ablation section approximately 540° ensures a complete, closed lesion pattern with minimal power requirements. Further, the frontal diameter defined by the ablation section 722 is sized to be larger than a pulmonary vein ostium. For example, in one preferred embodiment, a maximum outer diameter defined by the ablation section 722 is approximately 35 mm. Alternatively, other maximum outer diameters corresponding with pulmonary vein ostiums are acceptable. Preferably, however, the maximum frontal outer diameter defined by the ablation section 722 is in the range of 10 mm-35 mm.

The tip 724 includes a proximal section 728 that continues the distally decreasing radius helix otherwise defined by the ablation section 722. That is to say, a relatively uniform decreasing radius helix is defined by the ablation section 722 and the proximal section 728 of the tip 724. However, the proximal section 728 of the tip 724 is preferably not capable of ablating tissue during an ablative procedure at the ablation section 722, as described below. The proximal section 728 of FIG. 26 defines a maximum frontal outer diameter approximating a diameter of a pulmonary vein, +/−10 mm. With this configuration, the proximal section 728 is sized for placement within a pulmonary vein (not shown).

Finally, the leader section 726 extends distally from the proximal section 728 and is preferably relatively linear. To this end, the leader section 726 can be coaxially aligned with, or angled with respect to, a central axis defined by the intermediate portion 718. Stated otherwise, the relatively linear leader section 726 is preferably angled with respect to, alternatively aligned with, a central axis defined by the helix of the ablation section 722/proximal section 728. Regardless, by employing a relatively linear or straight design, the leader section 726 more readily locates a pulmonary vein, and is easily maneuvered within a pulmonary vein. Further, the relatively linear design is easily identified on an appropriate viewing device, such as a fluoroscope, such that the leader section 726 serves as an indicator of venous branching.

In addition to the varying shapes defined by the ablation section 722 and the tip 724, other differing features are preferably provided. For example, in a most preferred embodiment, the catheter body 704 is highly similar to the catheter body 402 (FIGS. 13A-13C) previously described, such that the ablation section 722 is formed from a microporous material, preferably expanded PTFE, that is fluidly connected to the fluid input port 710 by a lumen (not shown). Further, the shaping wire 706, similar to that previously described, is slidably disposed within the catheter body 704 for selectively forming the distal portion 720 to the shape illustrated in FIG. 26. In one preferred embodiment, and as previously described, the shaping wire 706 positions a coil electrode(s) at the ablation section 722. Alternatively, the coil electrode(s) can be independently maintained within the ablation section 722 apart from the shaping wire 706. Regardless, this one preferred configuration, the ablation section 722 is porous, whereas the tip 724 is impermeable to fluid flow. Even more preferably, the tip 724, and in particular the leader section 726, is formed of a soft, atrumatic material such as low durometer polyurethane. Thus, the tip 724, and in particular the leader section 726, has a lower durometer than a remainder of the catheter body 704, and will not cause trauma to contacted tissue (e.g., pulmonary vein). To further soften the leader section 726, the distal-most section of the shaping wire 706 (otherwise disposed within and "shaping" the leader section 726) is preferably taper ground to a smaller diameter than a remainder of the wire 706.

An additional preferred feature of the catheter assembly 700 is the inclusion of an electrode 729 on the leader section 726; spaced electrodes 730 (referenced generally in FIG. 26) along the proximal section 728 (i.e., distal the ablation section 722 and proximal the leader section 726); electrodes 732 adjacent, but proximal, the ablation section 722; and an electrode 734 along the intermediate portion 718. In a preferred embodiment, each of the electrodes 729-734 is a band electrode capable of sensing electrical activity, as known in the art. As such, each of the electrodes 729-734 is electrically connected to a device (not shown) otherwise associated with the catheter assembly 700 for analyzing signals generated by the electrodes 729-734, and is preferably an ECG reference electrode. Thus, the electrodes 729-734 serve as reference electrodes, available for confirming complete ablation as described below. Alternatively, or in addition, one or more of the electrodes 729-734, and in particular the electrodes 730, serve as pacing electrodes. Even further, one or more of the electrodes 729-734 is preferably formed from a radio opaque material (e.g., platinum-iridium) or other material viewable using available devices, such as a fluoroscope.

Figure 27:
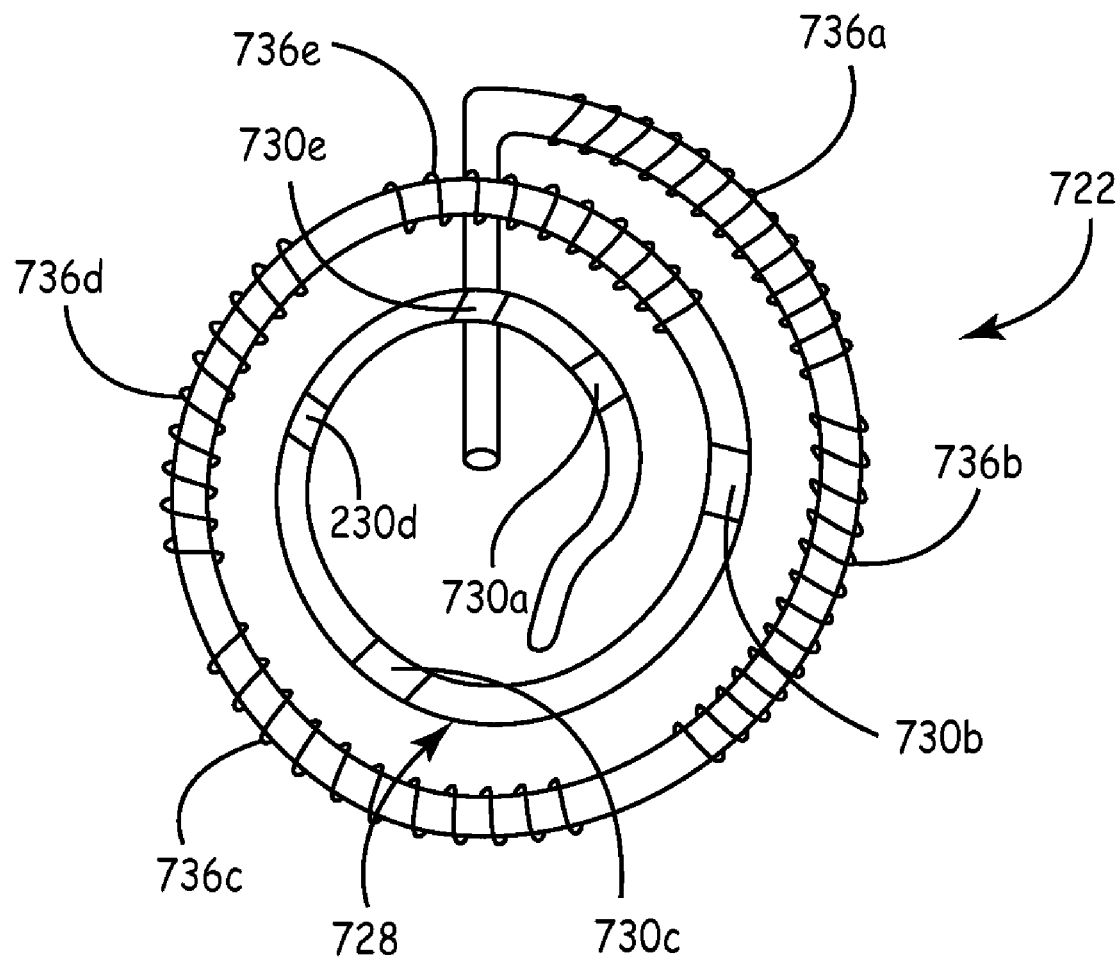
FIG. 27 is an enlarged, front elevational view of a portion of the catheter assembly of FIG. 26.

In a most preferred embodiment, the electrodes 730 along the proximal section 728 of the tip 724 are located at specific radial locations of the formed helix. The location of each of the electrodes 730 correlates with a radial location of respective ones of the preferred coil electrodes (not shown) relative to the helix of the ablation section 722. This relationship is best illustrated by the diagrammatic view of FIG. 27 in which a frontal representation of the decreasing radius helix otherwise defined by the ablation section 722 and proximal section 728 is provided. FIG. 27 includes, by way of example, five coil electrodes 736a-e disposed along the ablation section 722, and five of the reference electrodes 730a-e disposed along the proximal section 728. The coil electrodes 736a-e are preferably platinum-iridium, although a wide variety of other conductive materials are equally acceptable. Each of the reference electrodes 730a-e are radially aligned with a respective one of the coil electrodes 736a-e. Of course, any other number of coil electrodes 736 and reference electrodes 730 is equally acceptable, and more than one reference electrode 730 can be provided along the helix of the proximal section 728 and correlated with one of the coil electrodes 736. Regardless, as described in greater detail below, the spatially spaced and correlated nature of the coil electrodes 736 and the reference electrodes 730 facilitates selective ablation of specific portions of tissue (i.e., extra-ostial), as opposed to complete, "closed" ablation pattern.

Returning to FIG. 26, as is clear from the above, though the tip 724 extends directly from the ablation section 722, several differences exist. More particularly, and in the most preferred embodiment, the ablation section 722 and the tip 724 have a number of differing features, including shape, material, porosity, and durometer. Alternatively, the catheter body 704 can be configured such that the ablation section 722 and the tip 724 differ only in terms of shape, material, porosity, or durometer. Thus, for example, the catheter body 704 need not be configured to form the ablation section 722 with a microporous material. Instead, any of the other configurations previously disclosed herein can be incorporated. Along these same lines, the ablation section 722 can be configured to accommodate a variety of different ablative energy sources other than energize irrigated fluid. In a preferred embodiment, the ablation section 722 delivers an RF energy, and is a single electrical element or multiple elements each defining a portion of the circumference of the ablation section 722, each in the range of 10°-540°, more preferably each in the range of 45°-180°.

Figure 28:
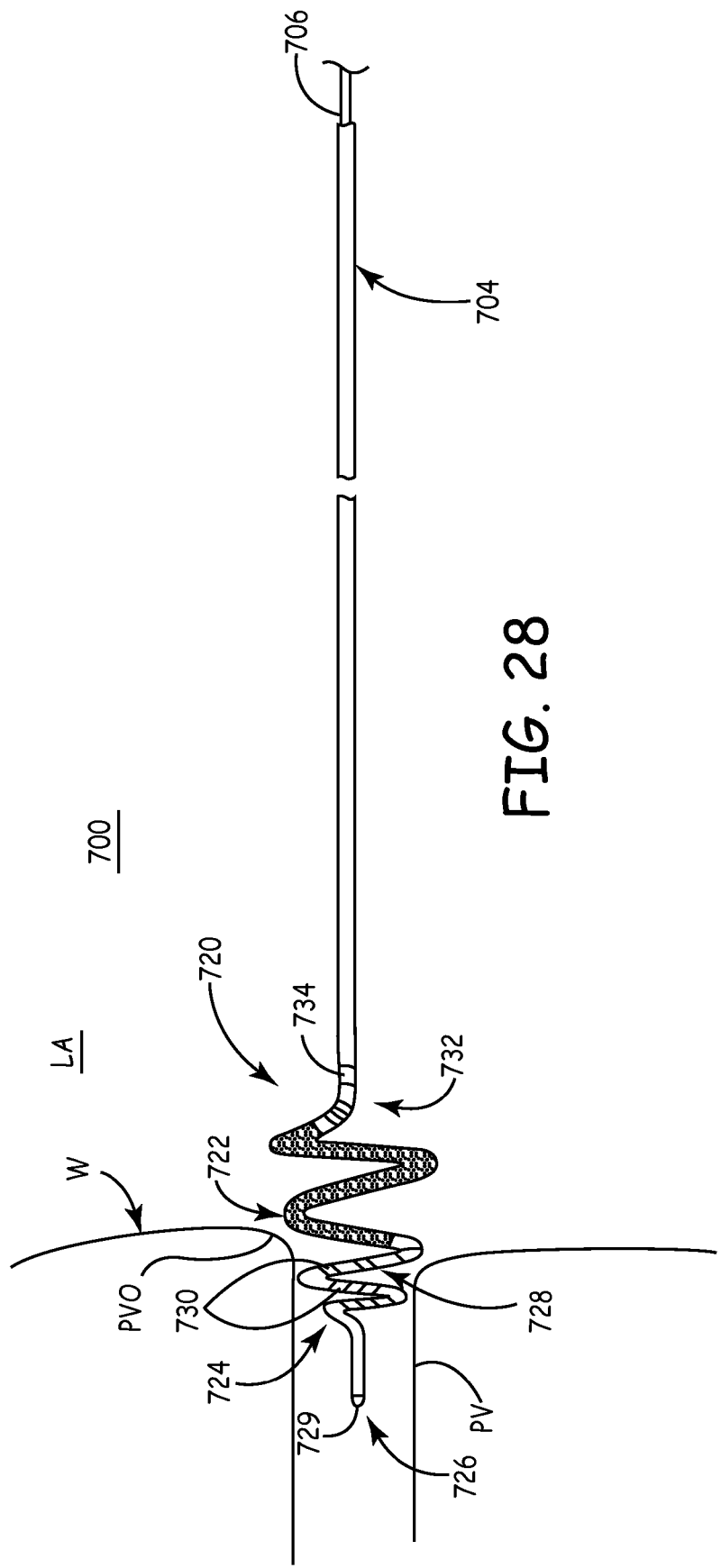
FIG. 28 illustrates use of the catheter assembly of FIG. 26 within a heart, the heart being represented diagrammatically.

Use of the catheter assembly 700 is highly similar to that previously described with respect to FIGS. 17A-17D. With further reference to FIG. 28, the distal portion 720 is, following previously described preparatory and deployment steps, positioned within the left atrium (LA). As a point of reference, FIG. 28 generally illustrates a portion of the left atrium LA and includes an atrium wall (W) and a pulmonary vein (PV). The pulmonary vein PV forms a pulmonary vein ostium (PVO) at the wall W. With this general description in mind, the tip 724 is employed to locate the pulmonary vein PV. The relatively linear leader section 726 is easily positioned within the pulmonary vein PV. Once the pulmonary vein has been located, the distal portion 720 is advanced until the ablation section 722 contacts the tissue wall W about the pulmonary vein ostium PVO. In this regard, the tip 724 readily slides along and within the pulmonary vein PV. The tip 724 is preferably formed of an atraumatic material such that contact between the tip 724 and the pulmonary vein PV does not damage the pulmonary vein PV tissue. Further, the preferred distally decreasing radius helix formed by the proximal section 728 of the tip 724 contacts the pulmonary vein PV wall, effectively seating the distal portion 720 within the pulmonary vein PV. Once seated, the ablation section 722 is essentially centered about the pulmonary vein ostium PVO. Subsequently, as the ablation section 722 is compressed (not illustrated in FIG. 28) against the wall W, a complete ablation perimeter is consistently defined about (proximal) the pulmonary vein ostium PVO (or extra-ostial).

Once properly positioned, extra-ostial ablation via the ablation section 722 is initiated. For example, with the one most preferred embodiment and as previously described, an appropriate fluid is irrigated through the ablation section 722, and is then energized via the coil electrode(s) (not shown), for example with RF energy. This energy is transferred, via the fluid irrigated along the ablation section 722, to the tissue contacted by the ablation section 722. The conductive fluid establishes a conductive path from the coil electrode(s) to the contacted tissue, thereby ablating the targeted tissue. Depending upon operator preference and indications of electrical activity recorded from the electrodes 730, it is possible to selectively ablate only specific portions of the extra-ostial perimeter by applying energy only to specific ones of the coil electrodes. In some instances, the atrial tissue fibers extend into the pulmonary vein PV along only a portion of the pulmonary vein ostium PVO circumference. The operator may desire to only ablate at this specific location, as opposed to forming a complete, closed ablation pattern. The catheter assembly 700 of the present invention promotes this procedure. In particular, and with additional reference to FIG. 27, the various reference electrodes 730a-e can be interrogated to determined where electrical activity is occurring relative to a circumference of the pulmonary vein ostium PVO. The corresponding coil electrode(s) 736a-e are then energized to effectuate partial, or quadrant ablation.

Following application of the ablation energy, the catheter assembly 700 is preferably operated to determine whether a closed, electrically isolating ablation pattern has been established in the chamber wall W, about or outside of the pulmonary vein ostium PVO. More particularly, one or more of the electrodes 729-734 are interrogated to evaluate electrical isolation of the pulmonary vein PV from the atrium wall W. The electrodes 729 along the tip 724 provide information relating electrical activity within the pulmonary vein PV, whereas the electrodes 732, 734 provide information relating to electrical activity within the left atrium LA. Thus, where the electrodes 729-734 are ECG reference electrodes, a comparison can be made between the electrical activity within the pulmonary vein PV (via the electrodes 730) and the electrical activity with the left atrium LA (via the electrodes 732, 734) or electrical activity sensed from a catheter placed in the coronary sinus. If it is determined that electrical activity within the pulmonary vein PV is similar or otherwise related to electrical activity at the left atrium LA, further ablation of the tissue wall W is required. Ablation energy can again be applied to further ablate the tissue wall W about the pulmonary vein ostium PVO. Once sufficient ablation has been achieved, the distal section 720 is retracted from the pulmonary vein PV. Subsequently, additional ablation patterns can be formed about other ones or all of the pulmonary vein ostia PVOs.

Figure 29A:
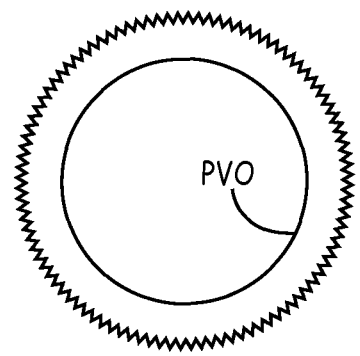
FIG. 29A-29C are simplified views of ablation patterns formed by the catheter assembly of FIG. 26.
Figure 29B:
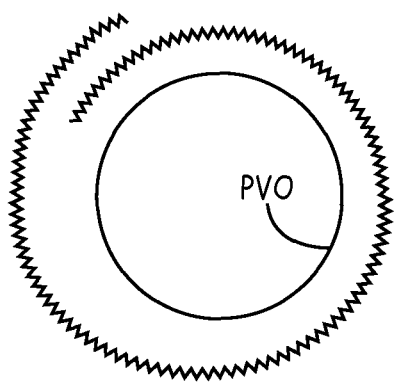
Figure 29C:
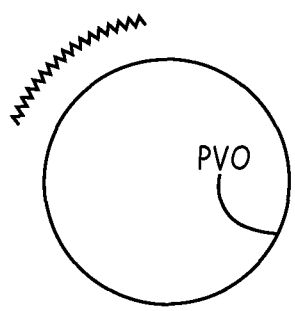

To best illustrate the ablation pattern capabilities of the catheter assembly 700, reference is made to the diagrammatic ablation illustrations of FIGS. 29A-C. In FIG. 29A, a full, circumferential, extra-ostial ablation pattern has been formed. In theory, where the individual loops of the ablation section 722 (FIG. 26) are aligned upon compression, the relatively continuous circle ablation pattern is formed. Conversely, the ablation pattern of FIG. 29B is generally spiral-shaped, a result of the individual loops of the ablation section 722 not being perfectly aligned. However, the radial spacing between individual turns of the spiral ablation pattern is so small such that the ablative effect extends across adjacent turns. As a result, an extra-ostial ablation pattern is again achieved. Finally, FIG. 29C illustrates a partial or quadrant ablation pattern as previously described, electrically isolating muscular tissue M extending into the pulmonary vein ostium PVO.

As previously described, the catheter assembly 700 can assume a wide variety of forms beyond the specific embodiment of FIG. 26. For example, the catheter assembly 700 can be configured to provide the distally decreasing helical shape of the ablation section 722 and the tip 724 via a component other than the shaping wire 706. Alternatively and/or in addition, a delivery catheter or sheath can be provided. Even further, the catheter assembly 700 can be provided with one or more pull wires as previously described to effect directional deflection.

Figure 30:
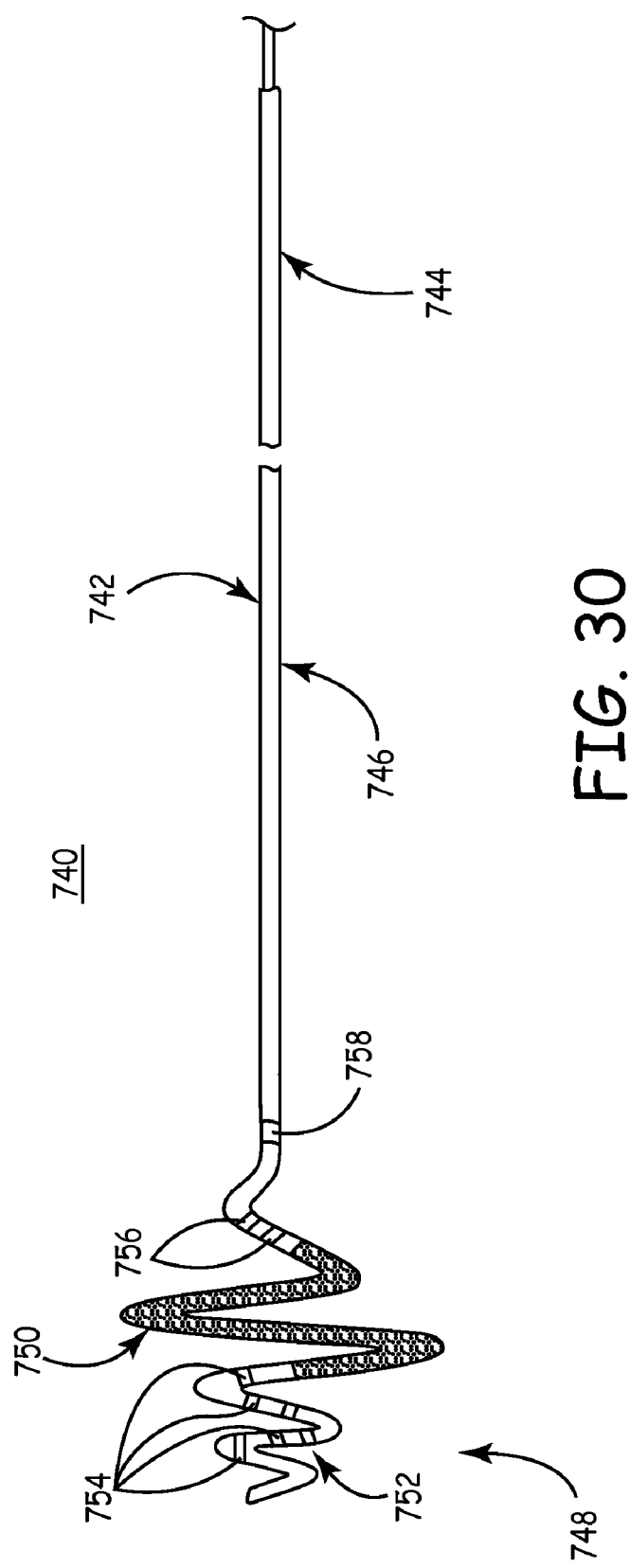
FIG. 30 is a side view of a portion of another alternative catheter assembly in accordance with the present invention.

Yet another alternative embodiment catheter assembly 740 is shown in FIG. 30. For ease of illustration, only a distal region of the catheter assembly 740 is depicted. The catheter assembly 740 is similar to the catheter assembly 700 (FIG. 26) previously described, and includes a catheter body 742. The catheter body 742 includes a proximal portion 744, an intermediate portion 746 and a distal portion 748. The proximal portion 744 is connected to an ablative energy source (not shown), such as that previously described. The intermediate portion 746 extends from the proximal portion 744 and defines a longitudinal axis. Finally, the distal portion 748 extends from the intermediate portion 746 and forms an ablation section 750 and a tip 752.

The ablation section 750 forms a loop substantially transverse to the longitudinal axis. In the embodiment of FIG. 30, the loop formed by the ablation section 750 is greater than a single revolution, preferably curving approximately 360°-540° but is not a radius decreasing helix. The tip 752 extends distally from the ablation section 750 and preferably forms a slightly distally decreasing radius helix. With this configuration, an outer diameter defined by the ablation section 750 is greater than an outer dimension of a pulmonary vein ostium (not shown), whereas a maximum outer diameter defined by the tip 752 approximates a diameter of a pulmonary vein (not shown). Though not illustrated, the tip 752 can form a distal leader, similar to the leader section 726 (FIG. 26) previously described.

As with the catheter assembly 700 (FIG. 26) previously described, the ablation section 750 and the tip 752 define differing shapes. In addition, and in accordance with a most preferred embodiment, the ablation section 750 is formed by microporous material as previously described, whereas the tip 752 is fluid impermeable. Thus, the catheter body 742, and in particular the ablation section 750, is configured to ablate tissue by irrigating energized conductive fluid, whereas ablation will not occur along the tip 752. Also, as with the catheter assembly 700 previously described, the catheter body 742 preferably includes electrodes 754 positioned along the tip 752; electrodes 756 positioned adjacent, but proximal, the ablation section 750; and an electrode 758 positioned along the intermediate portion 746.

In a preferred embodiment, a shaping wire 760 (shown partially in FIG. 30) is provided to selectively form the distal portion 748 to the shape illustrated in FIG. 30, similar to previously described embodiments. Though not illustrated, one or more coil electrodes are positioned within or along the ablation section 750 at various radial positions. Once again, the coil electrodes energize fluid irrigated through the ablation section 750 during use, and their radial location is preferably correlated with radial locations of respective ones of the electrodes 754 along the tip 752. Alternatively, and as previously described, a wide variety of other configurations can be employed to form the distal portion 748 to the shape shown in FIG. 30 and/or to provide ablative energy.

Figure 31:
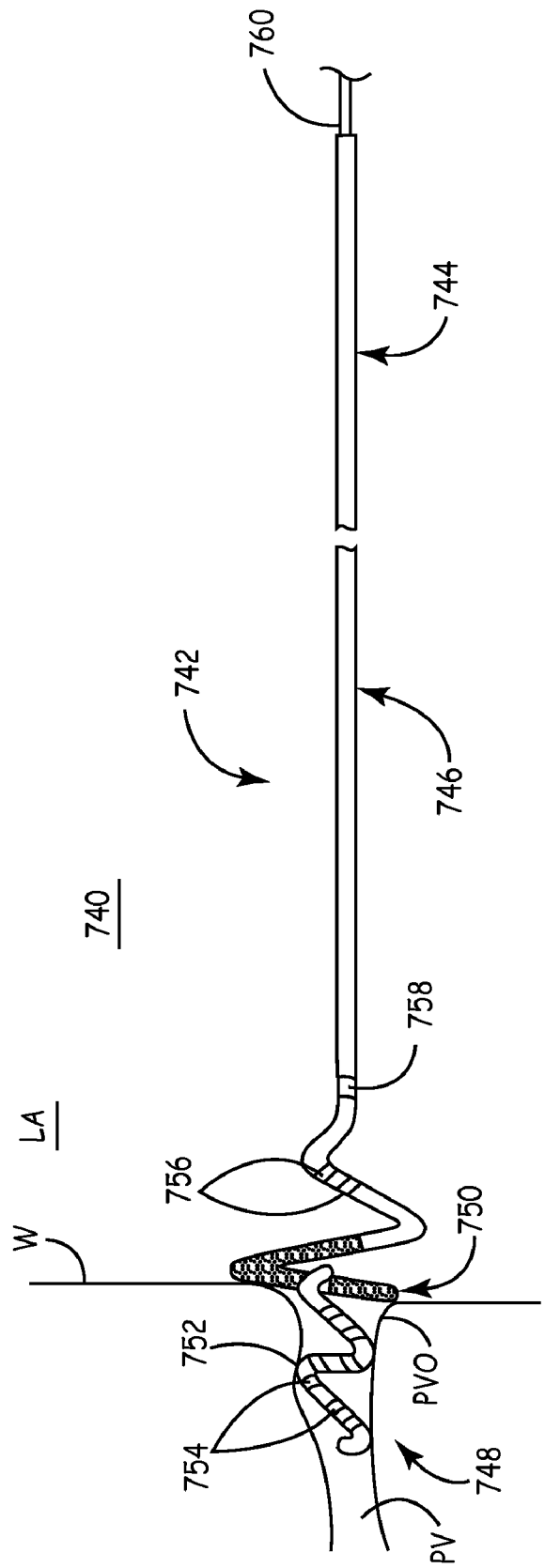
FIG. 31 illustrates use of the catheter assembly of FIG. 30 within a heart.

During use, and with reference to FIG. 31, following various preparatory steps, the distal portion 748 is deployed within the left atrium LA as previously described. As a point of reference, FIG. 31 depicts the catheter body 740, and in particular the ablation section 750, compressed against the chamber wall W. With this in mind, the tip 752 is first used to locate the pulmonary vein PV. Once again, the distally decreasing radius helix form of the tip 752 promotes placement within the pulmonary vein PV with minimal trauma to the pulmonary vein PV tissue. Once located, the distal portion 748, and in particular, the tip 752 is advanced within the pulmonary vein PV until the ablation section 750 contacts the tissue wall W. In this regard, the tip 752 essentially seats within the pulmonary vein PV, such that the ablation section 750 is substantially centered about the pulmonary vein ostium PVO and seats against the wall W in an extra-ostial position.

Once properly positioned, an ablative energy is applied to the tissue wall W via the ablation section 750. Following application of the ablation energy, the electrodes 754-758 are operated to sense electrical activity inside and outside of the pulmonary vein, as previously described. If it is determined that electrical activity continues to traverse the ablated lesion or selected portion(s) of the circumference, an ablation energy can again be applied to further ablate the tissue wall W about the entire pulmonary vein ostium PVO or only about selected portions of the pulmonary vein ostium as previously described.

Figure 32:
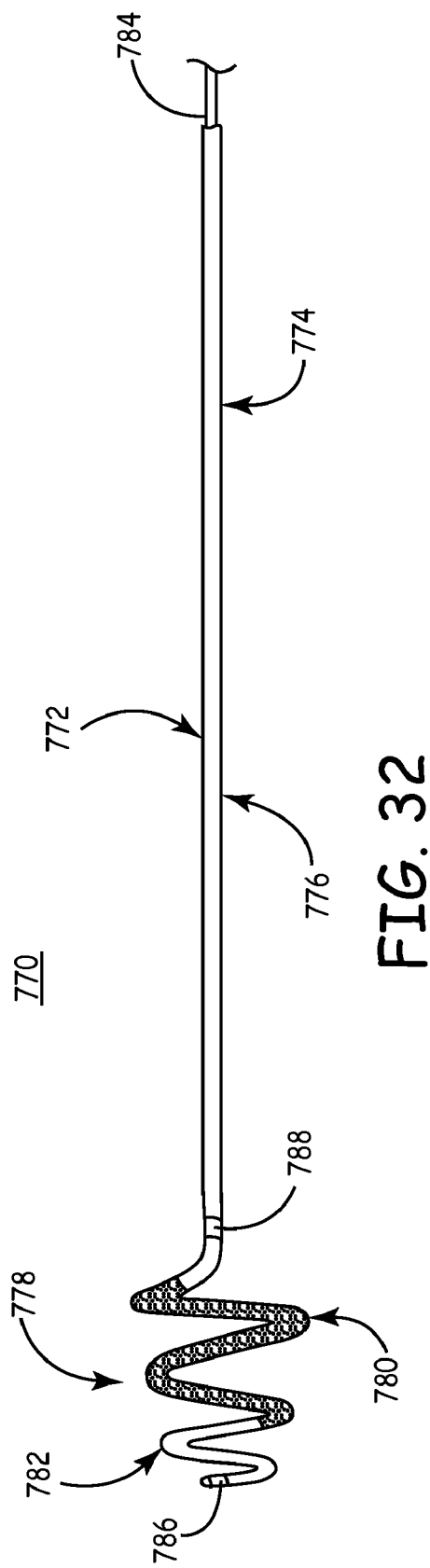
FIG. 32 is a side view of a portion of another alternative catheter assembly in accordance with the present invention.

Yet another alternative embodiment catheter assembly 770 is depicted in FIG. 32. For ease of illustration, only a distal region of the catheter assembly 770 is shown. The catheter assembly 770 is similar to the catheter assemblies 700 (FIG. 26) and 740 (FIG. 30) previously described, and includes a catheter body 772 having a proximal portion 774, an intermediate portion 776, and a distal portion 778. The proximal portion 774 is connected to an ablative energy source (not shown). The intermediate portion 776 extends from the proximal portion 774 and defines a longitudinal axis. Finally, the distal portion extends from the intermediate portion 778 and includes an ablation section 780 and a tip 782.

The tip 782 extends distally from the ablation section 780. Further, the ablation section 780 and the tip 782 combine to define a distally decreasing radius helix for the distal portion 778. Thus, unlike the catheter bodies 704, 742 previously described, the ablation section 780 and the tip 782 define a continuous shape. However, the ablation section 780 and the tip 782 have other varying features. For example, in the preferred embodiment, the ablation section 780 is formed of a microporous material, preferably expanded PTFE, previously described; whereas the tip 782 is formed of a fluid impermeable material. Further, the tip 782 is formed of an atraumatic material such as low durometer elastomer or thermoplastic and/or utilizing a smaller diameter shaping wire 784, and is thus softer than the ablation section 780.

As with previous embodiments, the catheter assembly 770 preferably incorporates a shaping wire 784 to selectively dictate the distally decreasing helical shape of the distal section 778. Once again, the shaping wire 784 preferably carries one or more coil electrodes (not shown) positioned within the ablation section 780. The coil electrodes serve to energize, via an ablative energy source (not shown), fluid irrigated through the ablation section 780. Alternatively, the distally decreasing helical shape of the distal portion 778 can be achieved with something other than the shaping wire 784, for example thermally formed thermoplastics or mechanically manipulated torque and puller wires that create a helical shape. Further, an ablation technique other than energized conductive fluid irrigated through the ablation section 780 can be incorporated into the catheter body 772. Regardless, the catheter body 772 preferably carries an electrode 786 along the tip 782 and an electrode 788 along the intermediate portion 776.

During use, the distal portion 778 is deployed similar to the embodiments previously described with respect to FIGS. 27 and 31. Once again, the tip 782 is uniquely configured to optimally locate and seat within a pulmonary vein (not shown). This relationship essentially ensures that the ablation section 780, once compressed against the tissue wall is centered about the pulmonary vein ostium (not shown), more particularly, in an extra-ostial location. Finally, the electrodes 786, 788 provide a means for evaluating electrical activity both inside and outside of the pulmonary vein.

The catheter assembly of the present invention provides a highly viable tool for electrically isolating a vessel, such as a pulmonary vein or coronary sinus, from a chamber, such as the left atrium. With respect to one preferred embodiment in which the distal portion of the catheter body forms a distally decreasing radius helix, the ablation section is readily and consistently positioned about a pulmonary vein ostium. In this regard, by forming the distal portion to include both an ablation section and a distally extending tip, the pulmonary vein in question is easily located. Further, the tip is preferably formed to seat within the pulmonary vein, thereby providing a user with a tactile confirmation of proper positioning. Finally, reference electrodes are preferably provided both inside and outside of the pulmonary vein to confirm electrical isolation thereof following ablation.

Although the present invention has been described with reference to preferred embodiments, workers skilled in the art will recognize that changes may be made in form and detail without departing from the spirit and scope of the invention. For example, the preferred embodiment has described electrical isolation of a pulmonary vein from the left atrium for treatment of atrial fibrillation. Alternatively, the method and apparatus of the present invention may be utilized in the treatment of other cardiac arrhythmias, such as isolating the coronary sinus from the right atrium, the superior vena cava, or isolating the outflow tract (or pulmonary valve) from the right ventricle. Further, with respect to the preferred embodiments described with reference to FIGS. 26-32, certain features can be altered or eliminated while still providing a viable device. For example, the ablation section and tip need not be made of differing materials. Further, a variety of ablative energy sources are available, including ultrasound, RF energy, microwave energy, laser, cryogenic energy, thermal energy, etc. Further, while a shaping wire has preferably been employed, the catheter body itself can be made of a shape memory material able to achieve the desired shape. In addition, the shaping wire may be taper ground to reduce its diameter near the distal end thereof (corresponding to the tip or leader section of the catheter body), thereby reducing the stiffness of the catheter body tip upon final assembly. Even further, the catheter body can be provided with various pull wires, the maneuvering of which selectively forms the distal portion to the desired shape. Finally, other features associated with different embodiments can be incorporated into the catheter assembly of FIGS. 26-32. Even further, other features not specifically disclosed can be employed. For example, the catheter assembly may include a rapid exchange feature for quick placement over, and removal from, a guidewire.

What is claimed is:

1. A catheter assembly, comprising:
a catheter body including a proximal portion, an intermediate portion extending from the proximal portion and a distal portion extending from the intermediate portion; the distal portion forming a distally decreasing radius helix including an ablation section having a predetermined frontal diameter, the ablation section including a plurality of independently operable ablative elements; and
an ablative energy source coupled to the ablation section to activate the ablative elements;
wherein upon activation by the energy source, one or more of the plurality of ablative elements ablates a desired lesion pattern;
wherein the catheter body forms a lumen extending from the proximal portion to the distal portion, and further wherein the ablation section is formed of a microporous polymer, and further wherein the catheter assembly further comprises a fluid source for supplying a liquid to the lumen such that upon activation of the ablative energy source, an energy is applied to fluid irrigated to an exterior surface of the ablation section.

2. The catheter assembly of claim 1, wherein the distal portion of the catheter body further includes a tip extending distally from the ablation section; the tip including a substantially linear distal leader segment.

3. The catheter assembly of claim 2, wherein the tip is softer than a remainder of the catheter body.

4. The catheter assembly of claim 2, wherein the distal leader segment of the tip is softer than a remainder of the tip.

5. The catheter assembly of claim 2, further comprising a plurality of electrodes spaced along the tip and coupled thereto, wherein the plurality of electrodes serve as reference electrodes to confirm complete ablation.

6. The catheter assembly of claim 2, further comprising a plurality of electrodes spaced along the tip and coupled thereto, wherein the plurality of electrodes serve as reference electrodes to select specific portions of tissue for ablation.

7. The catheter assembly of claim 2, wherein the desired lesion pattern effects a partial or quadrant ablation about an extra-ostial perimeter.

8. A method for forming an ablation pattern to electrically isolate a pulmonary vein for treatment of cardiac arrhythmia, comprising:
positioning a part of a distal portion of an ablation catheter within an ostium of the pulmonary vein, the distal portion forming a distally decreasing radius helix and including an ablation section, the ablation section including a plurality of independently operable ablative elements;
supplying a liquid to a lumen extending from the proximal portion to the distal portion of the catheter body;
irrigating an exterior surface of the ablation section with said liquid; and
applying energy from one or more of the plurality of ablative elements to the irrigated exterior surface to ablate a desired lesion pattern.

9. The method of claim 8, wherein the desired lesion pattern effects a partial or quadrant ablation about an extra-ostial perimeter.

10. The method of claim 8, wherein said ablation catheter further includes reference electrodes and further including the step of measuring electrical activity with the reference electrodes.

11. The method of claim 10, wherein the reference electrodes include a first set of electrodes positioned distal to the ablation section.

12. The method of claim 11, wherein the reference electrodes further include a second set of electrodes positioned proximal to the ablation section.

* * * * *